(12) United States Patent
Hall et al.

(10) Patent No.: US 6,261,304 B1
(45) Date of Patent: Jul. 17, 2001

(54) DELIVERY METHODS FOR LEFT VENTRICULAR CONDUIT

(75) Inventors: Todd A. Hall, Goshen; Greg R. Furnish; Simon M. Furnish, both of Louisville, all of KY (US); Scott J. Wolf, Minneapolis, MN (US); Peter J. Wilk, New York, NY (US); David Y. Phelps, Louisville, KY (US)

(73) Assignee: Percardia, Inc., Merrimack, NH (US)

( * ) Notice: Subject to any disclaimer, the term of this patent is extended or adjusted under 35 U.S.C. 154(b) by 0 days.

(21) Appl. No.: 09/368,868

(22) Filed: Aug. 4, 1999

Related U.S. Application Data

(63) Continuation-in-part of application No. 09/150,181, filed on Sep. 10, 1998.

(51) Int. Cl.$^7$ ..................................................... A61M 29/00
(52) U.S. Cl. ........................... 606/194; 606/108; 604/264
(58) Field of Search ..................................... 606/194, 108, 606/198, 191, 192; 600/434, 585; 604/96.01, 264, 164.13, 528, 530

(56) References Cited

U.S. PATENT DOCUMENTS 3,419,010  12/1968  Williamson .
4,836,204   6/1989  Landymore et al. .

(List continued on next page.)

FOREIGN PATENT DOCUMENTS 0 834 287  4/1998  (EP) .
0 900 547  3/1999  (EP) .
0 900 548  3/1999  (EP) .

(List continued on next page.)

OTHER PUBLICATIONS

Massimo, M.D. et al., "Myocardial Revascularization by a New Method of Carrying Blood Directly from the Left Ventricular Cavity into the Coronary Circulation," *Journal Of Thoracic Surgeons*, Aug. 1997, vol. 34, No. 2, pp. 257–264.

(List continued on next page.)

Primary Examiner—Pedro Philogene
(74) Attorney, Agent, or Firm—Finnegan, Henderson, Farabow, Garrett & Dunner, L.L.P.

(57) ABSTRACT

Described herein are various methods and apparatuses for delivering stents or conduits and other devices into the myocardium of a patient. One preferred stent delivery system provides access to the insertion site in the myocardium by advancing a delivery catheter through a blockage in a coronary artery, or around the blockage through a coronary vein or through a channel or tunnel formed around the blockage. In one embodiment, once the distal end of the delivery catheter is adjacent the myocardium, an angled bend is created in the catheter by actuating expandable steering guides mounted to the catheter which cooperate with the walls of the blood vessel to cause the catheter to turn. Then, a guidewire is advanced through the delivery catheter and into the myocardium. In another embodiment, a tip-deflecting pull wire extends from the distal end of the delivery catheter which may be actuated to turn towards and then inserted into the myocardium. In another embodiment, an exit port facing the insertion site is provided within the catheter or a balloon mounted on the catheter so that a guidewire may be directed through a lumen and out the exit port into the myocardium. Once the guidewire punctures into the myocardium, the guidewire is anchored using barbs, balloons or other actuatable members to secure the guidewire to the myocardium. Subsequently, using a push-pull mechanism, stents and other medical devices can be advanced over the guidewire into the myocardium.

29 Claims, 76 Drawing Sheets

U.S. PATENT DOCUMENTS

| | | | |
|---|---|---|---|
| 4,861,336 | 8/1989 | Helzel. | |
| 4,932,413 * | 6/1990 | Shockey et al. | 606/194 |
| 5,000,734 | 3/1991 | Boussignac et al. . | |
| 5,035,702 | 7/1991 | Taheri . | |
| 5,258,008 | 11/1993 | Wilk . | |
| 5,287,861 | 2/1994 | Wilk . | |
| 5,290,295 * | 3/1994 | Querals et al. | 606/108 |
| 5,330,486 | 7/1994 | Wilk . | |
| 5,386,818 | 2/1995 | Schneebaum et al. . | |
| 5,409,004 * | 4/1995 | Sloan | 604/96.01 |
| 5,409,019 | 4/1995 | Wilk . | |
| 5,429,144 | 7/1995 | Wilk . | |
| 5,431,168 | 7/1995 | Webster, Jr. . | |
| 5,470,320 | 11/1995 | Tifenbrun et al. . | |
| 5,500,012 | 3/1996 | Brucker et al. . | |
| 5,542,938 * | 8/1996 | Avellanet et al. | 606/194 |
| 5,655,548 | 8/1997 | Nelson et al. . | |
| 5,662,124 | 9/1997 | Wilk . | |
| 5,683,447 | 11/1997 | Bush et al. . | |
| 5,722,972 | 3/1998 | Power et al. . | |
| 5,733,267 | 3/1998 | Del Toro . | |
| 5,755,682 | 5/1998 | Knudson et al. . | |
| 5,758,663 | 6/1998 | Wilk et al. . | |
| 5,797,920 | 8/1998 | Kim . | |
| 5,800,450 | 9/1998 | Lary et al. . | |
| 5,810,836 | 9/1998 | Hussein et al. . | |
| 5,824,071 | 10/1998 | Nelson et al. . | |
| 5,830,222 | 11/1998 | Makower . | |
| 5,878,751 | 3/1999 | Hussein et al. . | |
| 5,885,258 | 3/1999 | Sachdeva et al. . | |
| 5,885,259 | 3/1999 | Berg . | |
| 5,885,276 | 3/1999 | Ammar et al. . | |
| 5,891,154 | 4/1999 | Loeffler . | |
| 5,908,028 | 6/1999 | Wilk . | |
| 5,908,029 | 6/1999 | Knudson et al. . | |
| 5,944,019 | 8/1999 | Knudson et al. . | |
| 5,948,191 | 9/1999 | Solovay . | |
| 5,971,993 | 10/1999 | Hussein et al. . | |
| 5,980,503 * | 11/1999 | Chin | 604/96.01 |
| 5,984,956 | 11/1999 | Tweden et al. . | |
| 6,011,988 * | 1/2000 | Lynch et al. | 600/434 |
| 6,021,340 * | 2/2000 | Randolph et al. | 600/585 |
| 6,022,342 * | 2/2000 | Mukherjee | 604/528 |
| 6,027,473 | 2/2000 | Ponzi . | |
| 6,029,672 | 2/2000 | Vanney et al. . | |
| 6,036,677 | 3/2000 | Javier, Jr. et al. . | |
| 6,053,924 | 4/2000 | Hussein . | |
| 6,053,942 | 4/2000 | Eno et al. . | |
| 6,068,638 | 5/2000 | Makower . | |
| 6,071,292 | 6/2000 | Makower et al. . | |
| 6,076,529 | 6/2000 | Vanney et al. . | |
| 6,080,163 | 6/2000 | Hussein et al. . | |
| 6,093,166 | 7/2000 | Knudson et al. . | |
| 6,102,941 | 8/2000 | Tweden et al. . | |
| 6,123,682 | 9/2000 | Knudson et al. . | |
| 6,126,649 | 10/2000 | Van Tassel et al. . | |
| 6,126,654 | 10/2000 | Giba et al. . | |
| 6,132,451 | 10/2000 | Payne et al. . | |
| 6,139,541 | 10/2000 | Vanney et al. . | |

FOREIGN PATENT DOCUMENTS

| | | |
|---|---|---|
| 0 900 549 | 3/1999 | (EP) . |
| 0 900 574 | 3/1999 | (EP) . |
| 0 904 795 | 3/1999 | (EP) . |
| 0 976 363 | 2/2000 | (EP) . |
| 1 036 547 | 9/2000 | (EP) . |
| 2316322 | 10/1998 | (GB) . |
| 93/15791 | 8/1993 | (WO) . |
| 97/13463 | 4/1997 | (WO) . |
| 97/13471 | 4/1997 | (WO) . |
| 97/27893 | 8/1997 | (WO) . |
| 97/27897 | 8/1997 | (WO) . |
| 97/27898 | 8/1997 | (WO) . |
| 98/06356 | 2/1998 | (WO) . |
| 98/08456 | 3/1998 | (WO) . |
| 98/10714 | 3/1998 | (WO) . |
| 98/16161 | 4/1998 | (WO) . |
| 98/19614 | 5/1998 | (WO) . |
| 98/39038 | 9/1998 | (WO) . |
| 98/46115 | 10/1998 | (WO) . |
| 98/46119 | 10/1998 | (WO) . |
| 98/57591 | 12/1998 | (WO) . |
| 98/57592 | 12/1998 | (WO) . |
| 99/08624 | 2/1999 | (WO) . |
| 99/17683 | 4/1999 | (WO) . |
| 99/21490 | 5/1999 | (WO) . |
| 99/25273 | 5/1999 | (WO) . |
| 99/29251 | 6/1999 | (WO) . |
| 99/35979 | 7/1999 | (WO) . |
| 99/3600 | 7/1999 | (WO) . |
| 99/36001 | 7/1999 | (WO) . |
| 99/38459 | 8/1999 | (WO) . |
| 99/40868 | 8/1999 | (WO) . |
| 99/44524 | 9/1999 | (WO) . |
| 99/48545 | 9/1999 | (WO) . |
| 99/49793 | 10/1999 | (WO) . |
| 99/49910 | 10/1999 | (WO) . |
| 99/51162 | 10/1999 | (WO) . |
| 99/53863 | 10/1999 | (WO) . |
| 99/60941 | 12/1999 | (WO) . |
| 99/62430 | 12/1999 | (WO) . |
| 00/09195 | 2/2000 | (WO) . |
| 00/12029 | 3/2000 | (WO) . |
| 00/15146 | 3/2000 | (WO) . |
| 00/15147 | 3/2000 | (WO) . |
| 00/15148 | 3/2000 | (WO) . |
| 00/15149 | 3/2000 | (WO) . |
| 00/15275 | 3/2000 | (WO) . |
| 00/18462 | 4/2000 | (WO) . |
| 00/19920 | 4/2000 | (WO) . |
| 00/21436 | 4/2000 | (WO) . |
| 00/21461 | 4/2000 | (WO) . |
| 00/21463 | 4/2000 | (WO) . |
| 00/2449 | 5/2000 | (WO) . |
| 00/33725 | 6/2000 | (WO) . |
| 00/41632 | 7/2000 | (WO) . |
| 00/41633 | 7/2000 | (WO) . |
| 00/45711 | 8/2000 | (WO) . |
| 00/45886 | 8/2000 | (WO) . |
| 00/54661 | 9/2000 | (WO) . |
| 00/56387 | 9/2000 | (WO) . |

OTHER PUBLICATIONS

Lary, M.D. et al., "Myocardial Revascularization Experiments Using the Epicardium," *Archives of Surgery,* Jan. 1969, vol. 98, No. 1, pp. 69–72.

Munro, M.D. et al., "The possibility of myocardial revascularization by creation of a left ventriculocoronary artery fistula," *Journal of Thoracic and Cardiovascular Surgery,* Jul. 1969, vol. 58, No. 1, pp. 25–32.

Kuzela, M.D. et al., "Experimental evaluation fo direct transventricular revascularization," *The Journal of Thoracic and Cardiovascular Surgery,* Jun. 1969, vol. 57, No. 6, pp. 770–773.

Tweden et al., "Ventriculocoronary Artery Bypass (VCAB), a Novel Approach to Myocardial Revascularization," #2000–4653, Feb. 2000.

* cited by examiner

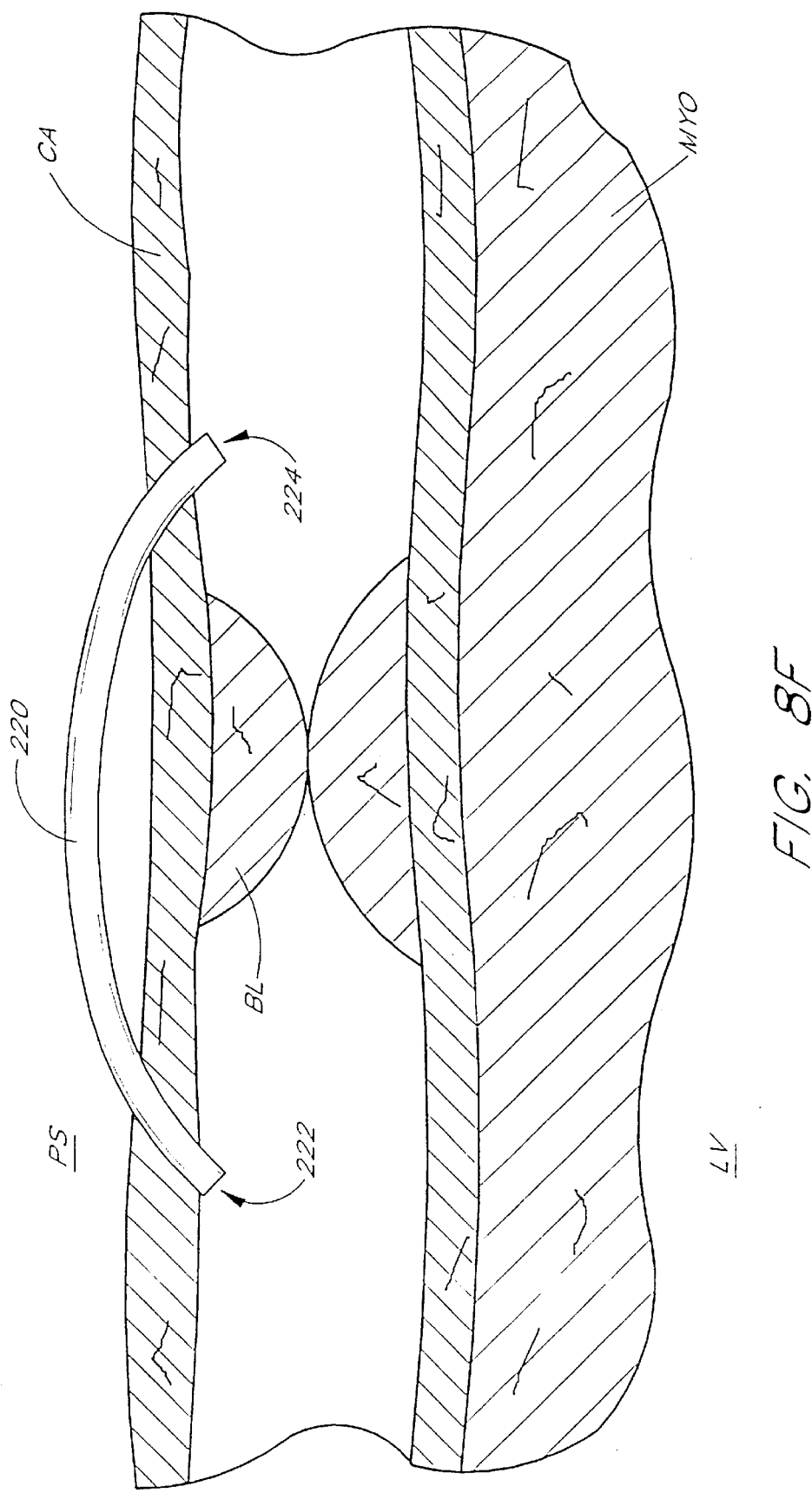

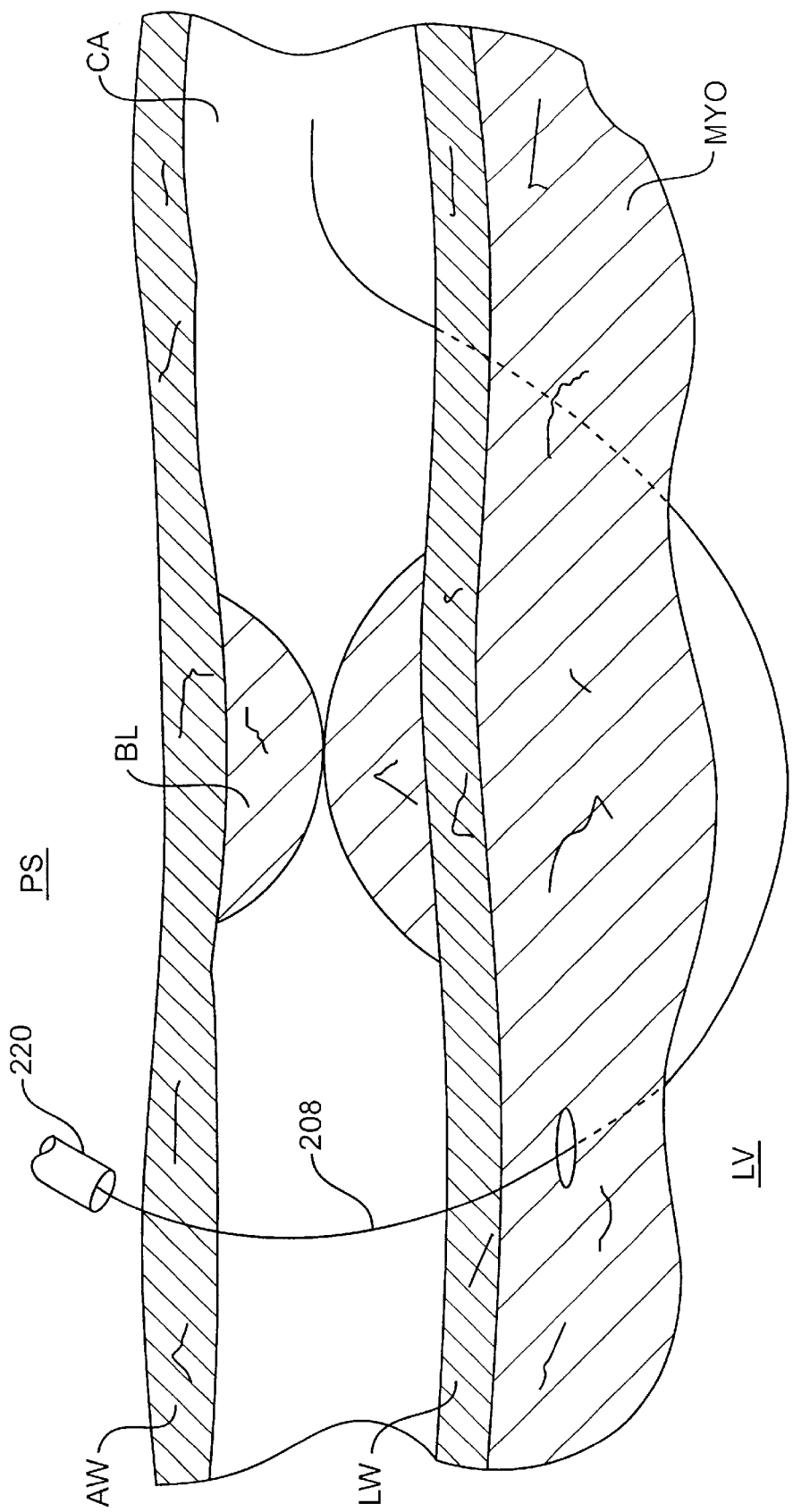

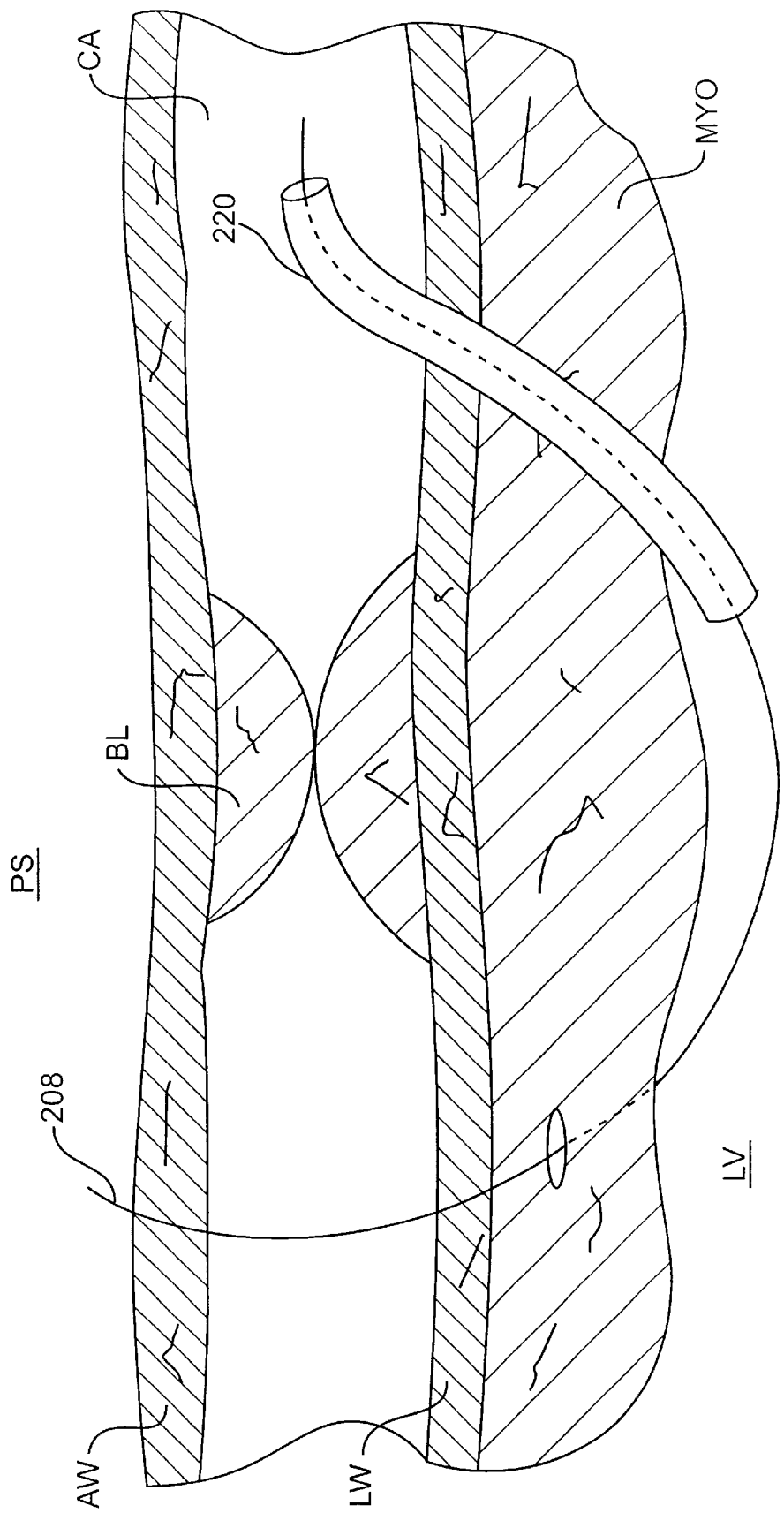

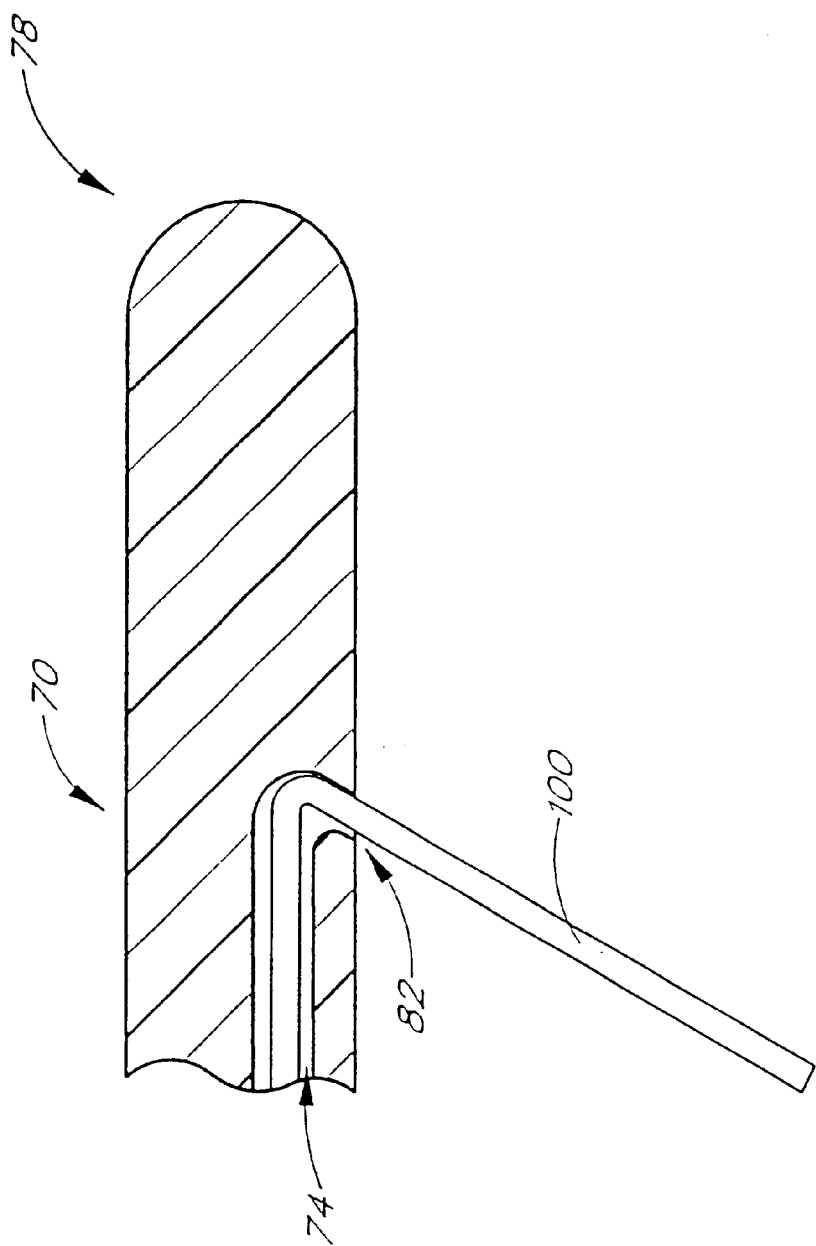

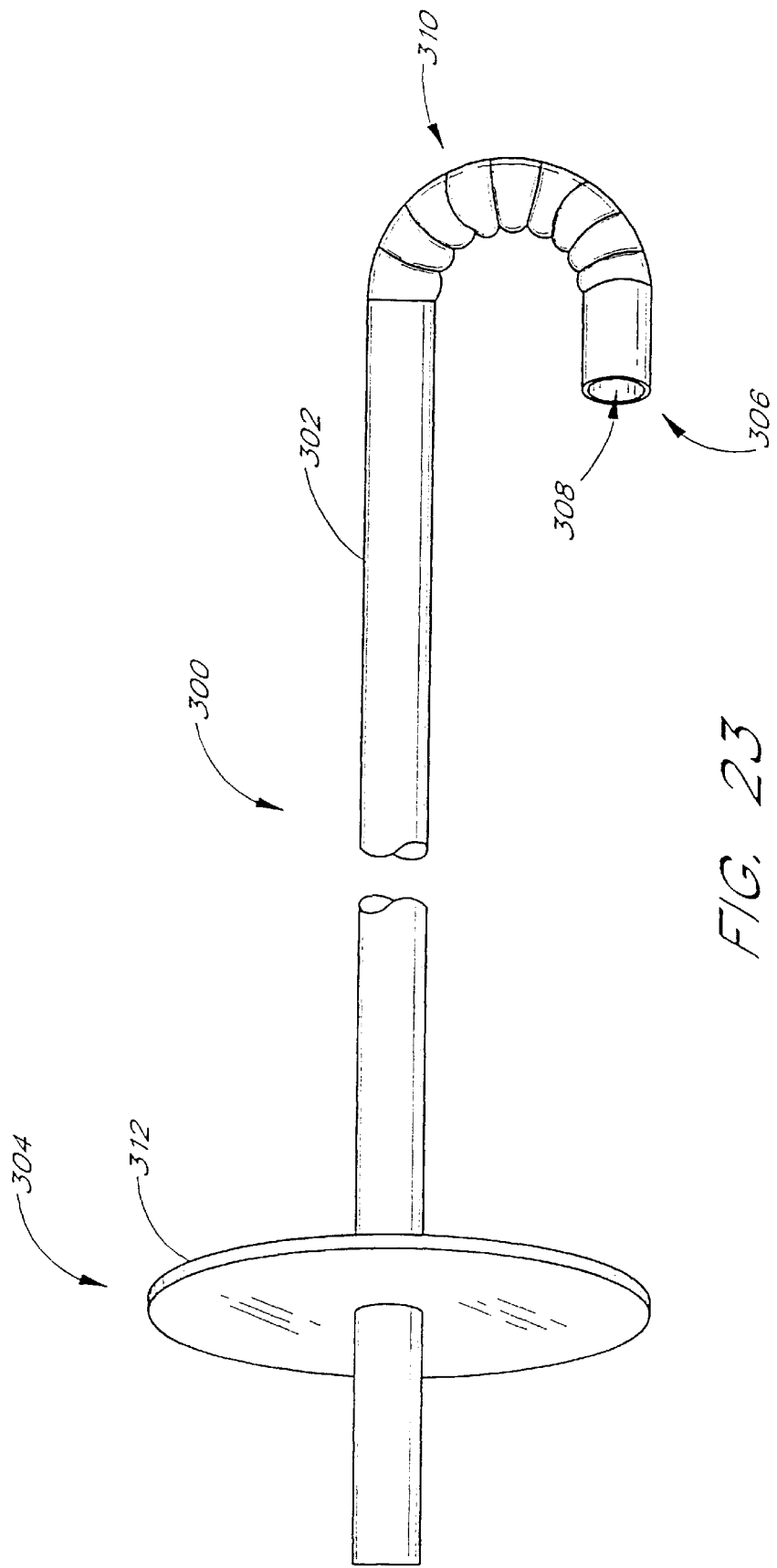

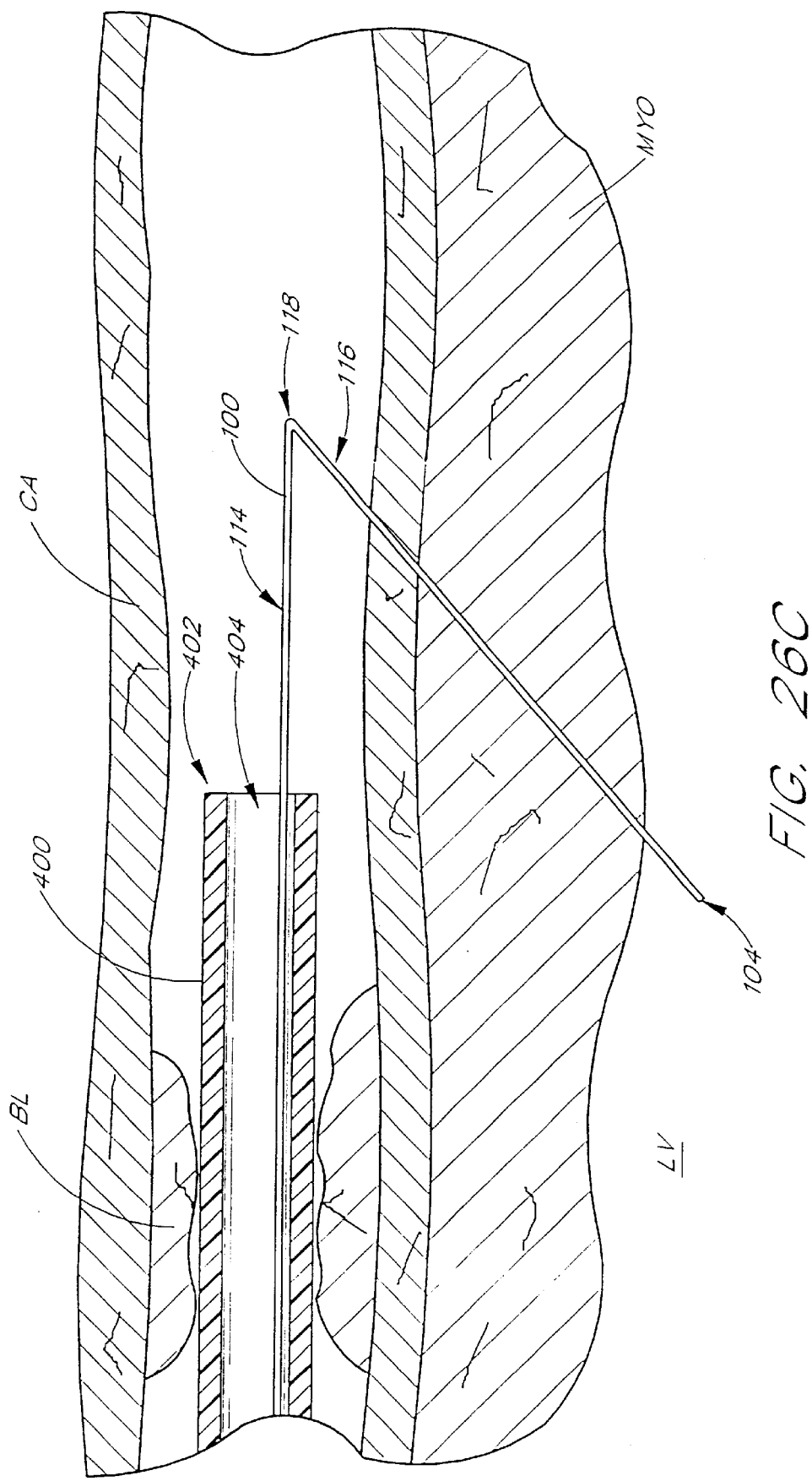

DELIVERY METHODS FOR LEFT VENTRICULAR CONDUIT

CROSS-REFERENCE TO RELATED APPLICATION

This application is a continuation-in-part of application Ser. No. 09/150,181, filed Sep. 10, 1998, the entirety of which is hereby incorporated by reference.

BACKGROUND OF THE INVENTION

1. Field of the Invention

The present invention relates to the delivery of a stent or conduit and other devices into the myocardium of a patient, and more particularly, to a stent or conduit delivery system to provide a bypass through the myocardium from the left ventricle into a coronary artery.

2. Description of the Related Art

Coronary arteries as well as other vessels frequently become clogged with plaque that at the very least impairs the efficiency of the heart's pumping action and can lead to heart attack and death. One conventional treatment for clogged coronary or other arteries is a bypass operation wherein one or more venous segments are inserted between the aorta and the coronary artery. The inserted venous segments or transplants act as a bypass of the clogged portion of the coronary artery and thus provide for a free or unobstructed flow of blood to the heart.

Such coronary artery bypass surgery, however, is expensive, time-consuming and traumatic to the patient. Hospital stays subsequent to the surgery and convalescence are prolonged.

A new coronary artery bypass technique is disclosed in U.S. Pat. No. 5,429,144. That technique utilizes a stent made of a biocompatible material and comprises steps of moving the stent in a collapsed configuration through a blood vessel of a patient's vascular system to the patient's heart, inserting the stent in the patient's myocardium, and upon disposition of the stent in the myocardium, expanding the stent from the collapsed configuration to a substantially tubular expanded configuration so that a blood flow path is formed at least partially through the myocardium.

One problem with the coronary artery bypass method providing a stent through the myocardium of the heart is how to get the stent into the myocardium. U.S. Pat. No. 5,429,144 describes a percutaneous approach wherein the stent is brought to the myocardium through the patient's vasculature on the distal end of a catheter, and advanced into the myocardium over a guidewire. One particular challenge is how to make an angled bend in the guidewire to puncture through the wall of the vessel and into the myocardium. This challenge is exacerbated when it is desired to penetrate the guidewire through the myocardium at an obtuse angle relative to the direction that the guidewire is advanced through the vasculature.

Another problem with this approach is that catheters delivering the guidewire, stent or other devices to be provided into the myocardium are conventionally guided to the puncture point through the blockage in the coronary artery. However, when the blockage is too large, a delivery catheter cannot access the desired insertion site.

In addition, it is often difficult to advance devices into the myocardium because of the traction and force necessary to push through the myocardium. This problem arises not only for delivery of the stent, but also for the delivery of dilation catheters used to expand the cross-section of the passageway through the myocardium, and other devices.

Accordingly, what is needed is a method and apparatus for delivering guidewires, stents and other devices into the myocardium. In particular, what is needed is a delivery system that can deliver these devices at an angled bend for transverse insertion into the myocardium. Moreover, what is needed is a delivery method and apparatus for advancing a delivery catheter to a puncture site in a coronary vessel when the blockage in the vessel is too large to permit passage of a catheter therethrough. What is also needed is a method and apparatus for advancement of a stent, dilation catheter or other device into and through the myocardium.

SUMMARY OF THE INVENTION

Briefly stated, the present invention addresses the above needs by providing various methods and apparatuses for delivering stents or conduits and other devices into the heart wall or myocardium of a patient. One preferred stent delivery system provides access to the insertion site in the myocardium by advancing a delivery catheter through a blockage in a coronary artery, or around the blockage through a coronary vein or through a channel or tunnel formed around the blockage. In one embodiment, once the distal end of the delivery catheter is adjacent the myocardium, an angled bend is created in the catheter by actuating expandable steering guides mounted to the catheter which cooperate with the walls of the blood vessel to cause the catheter to turn. Then, a guidewire is advanced through the delivery catheter and into the myocardium. In another embodiment, a tip-deflecting pull wire extends from the distal end of the delivery catheter which may be actuated to turn towards and then inserted into the myocardium. In another embodiment, an exit port facing the insertion site is provided within the catheter or a balloon mounted on the catheter so that a guidewire may be directed through a lumen and out the exit port into the myocardium. Once the guidewire punctures into the myocardium, the guidewire is anchored using barbs, balloons or other actuatable members to secure the guidewire to the myocardium. Subsequently, using a push-pull mechanism, stents and other medical devices can be advanced over the guidewire into the myocardium.

In one aspect of the present invention, a guidewire is delivered into the patient such that the proximal end of the guidewire extends out of the patient, while the distal end of the guidewire is positioned adjacent the heart wall. The distal end of the guidewire is inserted into the heart wall, and the guidewire is then anchored to the heart wall. An introducer catheter carrying a medical device is advanced over the guidewire to deliver the device into the heart wall.

In another aspect of the present invention, a method for delivering a conduit into a heart wall to bypass a blockage formed in a coronary artery is provided. A channel is created from a position proximal to the blockage in the coronary artery to a position distal to the blockage in the coronary artery. A guidewire is advanced through the channel until a distal end of the guidewire is adjacent the heart wall. The guidewire is inserted into the heart wall, and a conduit is advanced over the guidewire into the heart wall.

In another aspect of the present invention, a bypass around a blockage in a blood vessel is formed by delivering a guidewire along a pathway from a location in the blood vessel proximal to the blockage to a location in the blood vessel distal to the blockage. A channel is created along the pathway formed by the guidewire. This pathway may preferably be created either through the heart wall or through the pericardial space. The channel may be dilated and shunted along the pathway defined by the guidewire.

In another aspect of the present invention, a method is provided for creating a bypass around a blockage in a coronary artery, adjacent a heart wall. A needle is inserted into a patient into the heart wall, the needle having a lumen extending therethrough. The needle is advanced through the heart wall and into the coronary artery distal to the blockage. A guidewire is advanced through the lumen in the needle, the guidewire once advanced extending through the coronary artery proximal to the blockage, through the heart wall, and into the coronary artery distal to the blockage. The needle is removed from the patient while leaving the guidewire in place. A shunt is advanced over the guidewire, the shunt once advanced having a distal end in the coronary artery distal to the blockage.

In another aspect of the present invention, a method is provided for creating a bypass through the heart wall of a patient to bypass a blockage formed in a coronary artery. A first tunnel is created through the heart wall having a proximal end and a distal end. The proximal end of the tunnel opens into the coronary artery proximal to the blockage. The distal end of the tunnel is positioned within the heart wall. A second tunnel is created through the heart wall, the second tunnel having a first branch extending from the distal end of the first tunnel and opening into the coronary artery at a position distal to the blockage. A second branch of the second tunnel extends from the distal end of the first channel and opens into a heart chamber. A conduit is disposed in the second tunnel to provide a passageway therethrough.

In another aspect of the present invention, a delivery catheter is provided. This delivery catheter comprises an elongate tubular body having a proximal end and a distal end and a lumen extending therethrough. A first steering member is mounted on the distal end of the tubular body, and a second steering member is mounted on the distal end of the tubular body at a position distal to that of the anchoring member.

In another aspect of the present invention, a method for turning a distal end of a catheter within a body lumen is provided. The catheter comprises an elongate tubular body having a proximal end and a distal end. An anchoring member mounted to the distal end is actuated to secure the catheter against the body lumen. A steering member is mounted to the distal end of the of the guidewire at a position distal to that of the anchoring member. When actuated, the steering member cooperates with the body lumen to turn the distal end of the catheter.

In another aspect of the present invention, a method is provided for delivering a medical device to a delivery site within a patient. This method comprises providing a delivery catheter having a proximal end and a distal end and a lumen extending therethrough into a body lumen of the patient. The delivery catheter is secured within the body lumen. The distal end of the catheter is turned by actuating a steering member mounted on the distal end of the catheter which pushes off against a wall of the body lumen. The medical device is advanced through the lumen of the delivery catheter and out the distal end.

In another aspect of the present invention, a method for delivering a conduit into the heart wall of a patient is provided. A delivery catheter is advanced into the vasculature of the patient, the delivery catheter having a proximal end and a distal end and a lumen extending therethrough, until the distal end is adjacent the heart wall. A pull wire extending from the distal end of the delivery catheter is actuated to turn the pull wire toward the heart wall. The pull wire is advanced from the distal end of the delivery catheter into the heart wall. The conduit is delivered over the pull wire into the heart wall.

In another aspect of the present invention, a method for delivering a conduit into the heart wall of a patient is provided. A delivery catheter is advanced into the vasculature of the patient, the catheter having a proximal end and a distal end and a lumen extending from the proximal end to a side port near the distal end, until the side port faces the heart wall. A guidewire having a proximal end and a distal end is inserted into the lumen. The distal end of the guidewire is advanced through the lumen and out the side port. The guidewire advances into the heart wall, and the conduit is delivered over the guidewire into the heart wall.

In another aspect of the present invention, a method for delivering a conduit into the heart wall of a patient is provided. A delivery catheter is advanced into the vasculature of a patient, the catheter having a proximal end and a distal end, until the distal end is adjacent the heart wall. An anchoring member mounted on the distal end of the catheter is expanded to secure the delivery catheter within the vasculature. A guidewire having a proximal end and a distal end is inserted through a lumen in the expanded anchoring member, the lumen extending from a proximal end of the anchoring member to a side port facing the heart wall, so that the distal end of the guidewire exits through the side port. The guidewire advances into the heart wall and the conduit is advanced over the guidewire into the heart wall.

In another aspect of the present invention, a delivery catheter is provided. The catheter comprises an elongate body having a proximal end and a distal end. An expandable member is mounted on the distal end of the tubular body, the expandable member having a proximal end and a distal end and an exterior surface. A guide lumen extends from the proximal end of the balloon to a side port on the exterior surface of the expandable member for directing a medical device therethrough.

In another aspect of the present invention, a delivery catheter is provided comprising an elongate body having a proximal end and a distal end defining a generally longitudinally axis therebetween. A guidewire lumen extends at least partially between the proximal end and the distal end of the elongate body, having a proximal end and a distal end. An exit port at the distal end of the guidewire lumen creates a curve of between about 0 and 180 degrees relative to the longitudinal axis of the elongate body for directing a guidewire out of the lumen. In one embodiment, the exit port is a side port formed proximal to the distal end of the elongate body. In another embodiment, the exit port is at the distal end of the elongate body, and comprises a narrowing passageway between the guidewire lumen and the exit port.

In another aspect of the present invention, a method for treating an aneurysm is provided. A catheter having a proximal end and a distal end is advanced to the site of the aneurysm. An expandable member mounted on the distal end of the catheter is actuated to substantially enclose the aneurysm. An embolic element is inserted into the aneurysm.

In another aspect of the present invention, an assembly for delivering a medical device into the heart wall of a patient is provided. The assembly comprises an insertion tube having a proximal end and a distal end and a delivery channel extending therethrough. A tubular member is provided having a proximal end and a distal end and a lumen extending therethrough, the tubular member having a distal portion provided with an internal spring bias tending to form the distal portion into an arcuate configuration in the absence of an external straightening force on the distal portion. The tubular member is longitudinally slidable in the delivery channel. The distal portion may be alternately maintained in a relatively straightened configuration in the distal end of the channel and moved outside of the channel to assume the arcuate configuration. A guidewire is longitudinally slidable within the lumen of the tubular member.

In another aspect of the present invention, a method is provided for delivering a guidewire at an angle into a desired insertion site in the body. The method comprises delivering an insertion tube into the vasculature of a patient, the insertion tube having a delivery channel extending therethrough and once delivered having a proximal end located outside of the patient and a distal end located adjacent a desired insertion site. A delivery catheter is delivered through the delivery channel, the delivery catheter having a guidewire lumen extending therethrough. The delivery catheter once delivered has a proximal end outside of the patient and a distal end within the delivery channel. The distal end of the delivery catheter is ejected out of the delivery channel at the distal end of the insertion tube. The ejection of the delivery catheter from the delivery channel causes the distal end of the delivery catheter to turn toward the insertion site. A guidewire is advanced through the guidewire lumen into the insertion site.

In another aspect of the present invention, a method is provided for delivering a guidewire into the heart wall. A guidewire is inserted into a lumen of a delivery catheter, the guidewire having a proximal section and a distal section. The distal section of the guidewire is folded back over the proximal section while inside the delivery catheter lumen. The delivery catheter is delivered into a patient, the delivery catheter once delivered having a proximal end outside of the patient and a distal end adjacent a desired insertion site in the myocardium. The distal section of the guidewire is ejected out of the lumen of the delivery catheter at its distal end. The guidewire is pulled proximally such that the distal section punctures into the heart wall at an obtuse angle relative to the direction that the guidewire is ejected out of the lumen of the delivery catheter at its distal end.

In another aspect of the present invention, a method for delivering a guidewire into an insertion site in the body is provided. A delivery catheter having a proximal end and a distal end and a lumen extending therethrough is advanced into the body. The distal end of the delivery catheter once advanced is located adjacent the insertion site. The distal end of the delivery catheter is turned toward the insertion site. A guidewire is advanced through the lumen in the delivery catheter from the proximal end toward the distal end. The guidewire is guided out the distal end and into the insertion site through a narrowing passageway formed in the lumen.

In another aspect of the present invention, a method for delivering a medical device into a body tissue of a patient is provided. The method comprises inserting a guidewire having a proximal end and a distal end into the myocardium from a coronary blood vessel. The guidewire is anchored to the body tissue, and the medical device is pushed over the guidewire into the body tissue. The proximal end of the guidewire is correspondingly pulled proximally while the medical device is pushed distally in order to assist advancing the medical device through the body tissue.

In another aspect of the present invention, a delivery system for directing medical treatment at least partially into a heart wall is provided. The delivery system comprises a guidewire having a proximal end and a distal end, means for turning the distal end of the guidewire toward the heart wall, means for anchoring the guidewire to the heart wall, and a catheter carrying the medical treatment having a lumen extending therethrough for receiving the guidewire and advancing the catheter into the heart wall.

In another aspect of the present invention, a method for delivering a conduit into the heart wall of a patient to bypass a blockage formed in a coronary artery is provided. The method comprises advancing a catheter having a proximal end and a distal end and a lumen extending at least partially therethrough from the proximal end to a distal opening through the coronary artery of the patient until the distal opening is past the blockage. The catheter is turned so that the distal opening faces the heart wall. A wire having a proximal end and a distal end is extended through the distal opening such that the distal end punctures into the heart wall. The distal end of the wire is anchored to the heart wall. A dilation catheter is delivered over the wire, the catheter carrying a dilation balloon on a distal end thereof, until the balloon is within the heart wall. The dilation balloon is inflated to create an opening in the heart wall. The dilation balloon is then deflated and the dilation catheter removed from the wire. A conduit introducer catheter is delivered over the wire, the conduit introducer catheter carrying a conduit on a distal end thereof, until the conduit is located within the opening in the heart wall. The conduit is deployed within the opening in the myocardium.

In another aspect of the present invention, a method for delivering medical treatment into the heart wall of a patient is provided. A tubular wire is delivered into the patient, the wire having a lumen extending therethrough. The wire once delivered has a proximal end extending out of the patient and a distal end positioned adjacent the heart wall. Means for turning the distal end of the wire towards the heart wall are provided. Then, the distal end of the wire is inserted into the heart wall. Medical treatment is delivered through the lumen in the wire into the heart wall.

BRIEF DESCRIPTION OF THE DRAWINGS

FIGS. 8A–8F are schematic, partial cross-sectional views of a coronary artery with a blockage therein, showing a method for forming a bypass or access channel into the pericardial space around the blockage.

FIGS. 11A–11F are schematic, partial cross-sectional views of a coronary artery adjacent the left ventricle, showing a guidewire method for forming a left ventricular conduit.

FIG. 20C is a cross-sectional view of a delivery catheter having a side port for delivering a guidewire at a back angle.

FIG. 23 is a side view of a delivery catheter having a curved distal end.

FIGS. 26A–26C are schematic, partial cross-sectional views of a coronary artery adjacent a left ventricle, showing delivery of a folded guidewire into the myocardium.

DETAILED DESCRIPTION OF THE PREFERRED EMBODIMENTS

Figure 1A:
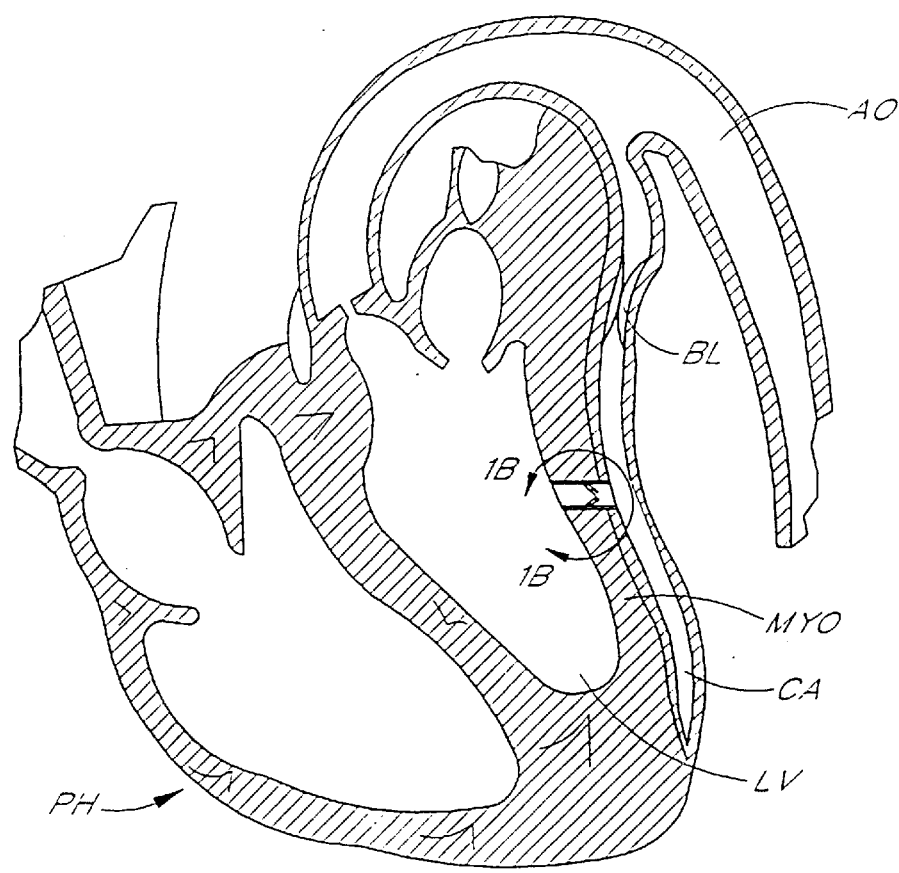
FIG. 1A is a schematic, cross-sectional view of a human heart, showing a stent in the myocardium of the heart for forming a bypass shunt between the left ventricle and a coronary artery.

The preferred embodiments described hereinbelow depict methods and apparatuses for delivering a stent or conduit into the myocardium to create a passageway between the left ventricle and coronary artery. It should be appreciated, however, that these embodiments may also be applied to the delivery of stents or conduits and other medical devices into other body tissues and vessels, and are particularly applicable for delivering devices at an angle relative to the axis of blood flow. In addition, the delivery methods and apparatuses described herein pertain to the placement of stents or conduits and other devices partially through the myocardium, as well as for drug delivery and similar applications.

The principles of the present invention are not limited to left ventricular conduits, and include conduits for communicating bodily fluids from any space within a patient to another space within a patient, including any mammal. Furthermore, such fluid communication through the conduits is not limited to any particular direction of flow and can be antegrade or retrograde with respect to the normal flow of fluid. Moreover, the conduits may communicate between a bodily space and a vessel or from one vessel to another vessel (such as an artery to a vein or vice versa). Moreover, the conduits can reside in a single bodily space so as to communicate fluids from one portion of the space to another. For example, the conduits can be used to achieve a bypass within a single vessel, such as communicating blood from a proximal portion of an occluded coronary artery to a more distal portion of that same coronary artery.

In addition, the conduits and related methods can preferably traverse various intermediate destinations and are not limited to any particular flow sequence. Preferred embodiments are disclosed, including direct transmyocardial communication from a left ventricle, through the myocardium and into the coronary artery. The term "transmyocardial" should not be narrowly construed in connection with the preferred fluid communication conduits, and other non-myocardial and even non-cardiac fluid communication are preferred as well. With respect to the walls of the heart (and more specifically the term "heart wall"), the preferred conduits and related methods are capable of fluid communication through all such walls including, without limitation, the pericardium, epicardium, myocardium, endocardium, septum, etc.

The bypass which is achieved with certain preferred embodiments and related methods is not limited to a complete bypass of bodily fluid flow, but can also include a partial bypass which advantageously supplements the normal bodily blood flow. Moreover, the occlusions which are bypassed may be of a partial or complete nature, and therefore the terminology "bypass" or "occlusion" should not be construed to be limited to a complete bypass or a complete occlusion but can include partial bypass and partial occlusion as described.

The preferred conduits and related methods disclosed herein can also provide complete passages or partial passages through bodily tissues. In this regard, the conduits can comprise stents, shunts, or the like, and therefore provide a passageway or opening for bodily fluid such as blood. Thus, although many of the preferred embodiments describe stents or shunts, it will be appreciated that other types of conduits may be used as well. Moreover, the conduits are not necessarily stented or lined with a device but can comprise mere tunnels or openings formed in the tissues of the patient.

The conduits of the present invention preferably comprise both integral or one-piece conduits as well as plural sections joined together to form a continuous conduit. The present conduits can be deployed in a variety of methods consistent with sound medical practice including vascular or surgical deliveries, including minimally invasive techniques, as described below. For example, various preferred embodiments of delivery rods and associated methods may be used. In one embodiment, the delivery rod is solid and trocar-like. It may be rigid or semi-rigid and capable of penetrating the tissues of the patient and thereby form the conduit, in whole or in part, for purposes of fluid communication. In other preferred embodiments, the delivery rods may be hollow so as to form the conduits themselves (e.g., the conduits are preferably self-implanting or self-inserting) or have a conduit mounted thereon (e.g., the delivery rod is preferably withdrawn leaving the conduit installed). Thus, the preferred conduit device and method for installation is preferably determined by appropriate patient indications in accordance with sound medical practices.

Figure 1B:
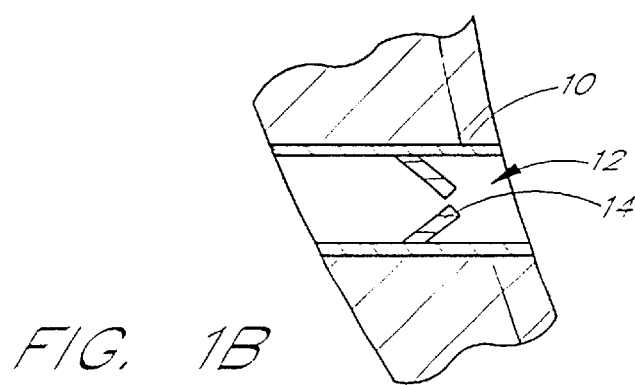
FIG. 1B is an enlarged view of the bypass shunt of FIG. 1A.

As illustrated in FIGS. 1A and 1B, a coronary artery bypass is accomplished by disposing a stent 10 in a heart wall or myocardium MYO of a patient's heart PH. The stent 10 preferably extends from the left ventricle LV of heart PH to a clogged coronary artery CA at a point downstream of a blockage BL to create a shunt 12 therethrough. Stent 10 is preferably made of a biocompatible material such as stainless steel or nitinol, although other materials such as Ti, Ti alloys, Ni alloys, Co alloys and biocompatible polymers may also be used. In one embodiment, stent 10 has a one way valve 14 to allow blood to flow from the left ventricle LV to the coronary artery CA. Although the stent 10 may elastically deform under the contractive pressure of the heart muscle during systole, the stent remains open to allow blood to pass from the patient's left ventricle LV into the coronary artery CA. During diastole, the blood pumped into coronary artery through shunt 12 is blocked by one-way valve 14 from returning to left ventricle LV. Further details are disclosed in U.S. Pat. No. 5,429,144, the entirety of which is hereby incorporated by reference. Various types of conduits or stents and medical devices and their methods of delivery, may also be used in accordance with the preferred embodiments described herein, such as described in copending applications entitled DESIGNS FOR LEFT VENTRICULAR CONDUIT, application Ser. No. 09/369,048, filed the same date herewith, LEFT VENTRICULAR CONDUITS WITH BLOOD VESSEL GRAFT, application Ser. No. 09/369,061, filed the same date herewith, VALVE DESIGNS FOR LEFT VENTRICULAR CONDUIT, application Ser. No. 09/368,393, filed the same date herewith, LEFT VENTRICULAR CONDUITS TO CORONARY ARTERIES AND METHODS FOR CORONARY BYPASS, Application Ser. No. 09/369,039, filed the same date herewith, and BLOOD FLOW CONDUIT DELIVERY SYSTEM AND METHOD OF USE, application Ser. No. 09/368,644, filed the same date herewith, and U.S. Pat. No. 5,662,124, all of which are hereby incorporated by reference in their entirety.

Figure 2:
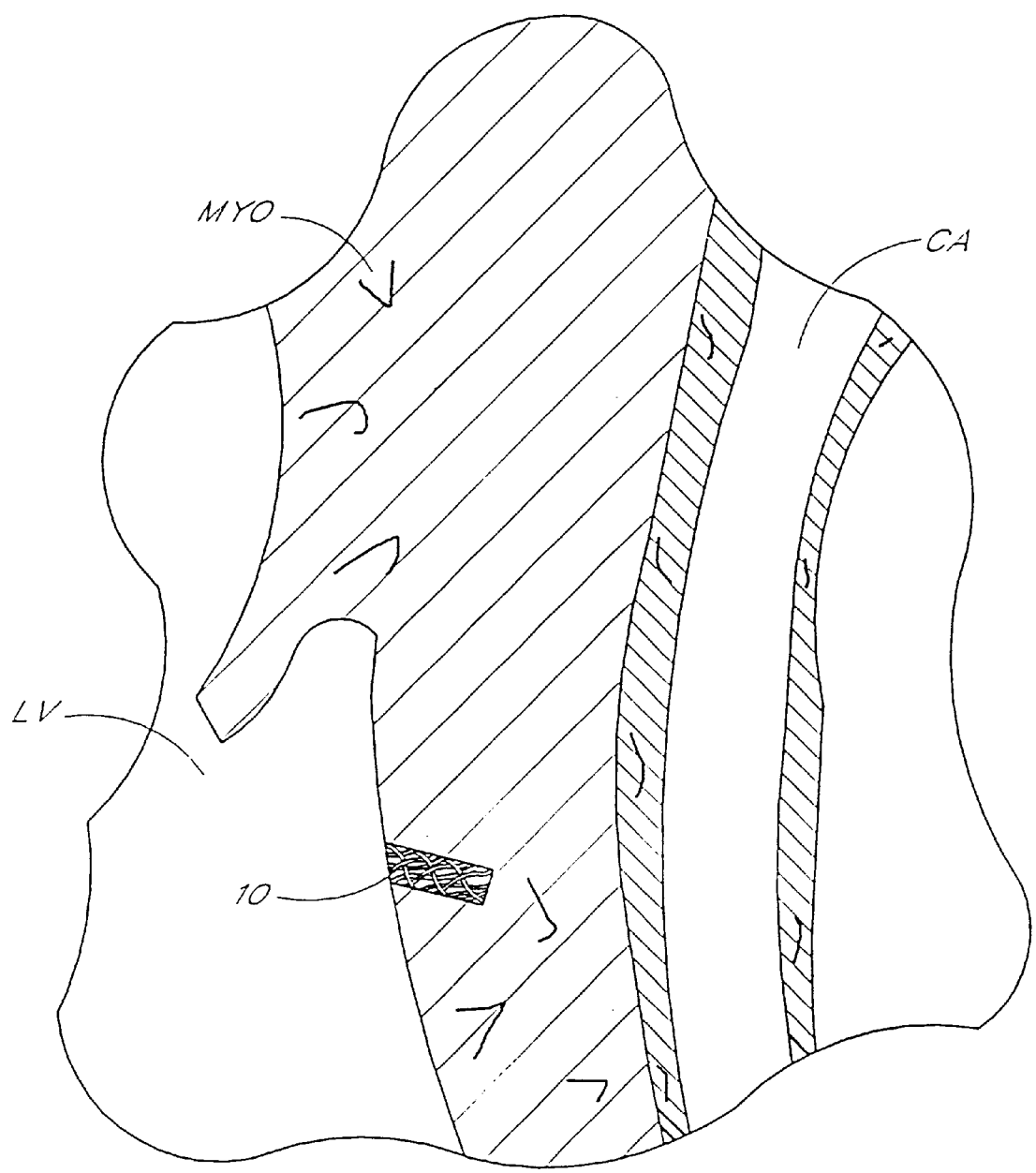
FIG. 2 is a schematic, partial cross-sectional view of a human heart, showing a stent extending partially into the myocardium from the left ventricle.

FIG. 2 illustrates another application for which it is desirable to dispose a stent into the myocardium of a patient In this application, a stent 10 is provided partially through the myocardium MYO from the left ventricle LV. The stent 10 guides blood directly into the myocardium MYO from the left ventricle to replenish oxygen-deprived heart muscle. Further details are disclosed in the above-referenced U.S. Pat. No. 5,429,144. Other applications providing a stent in the myocardium, extending either partially or entirely therethrough and accessed from either the coronary artery or the left ventricle, are also contemplated by the present invention.

To achieve some or all of the objects of the present invention, in particular creating a myocardial passageway between the left ventricle LV and the coronary artery CA for disposition of a stent therein, requires a delivery system capable of directing the necessary devices to and into the myocardium. As described in further detail below, the suitable delivery system: (1) provides access to the insertion site adjacent the myocardium; (2) creates an angled bend for transverse insertion of devices into the myocardium; and (3) directs devices into the myocardium for creation of the myocardial passageway.

I. Access To The Myocardium

The delivery system described herein preferably comprises one or more catheters or guidewires inserted percutaneously into the body, such as through the femoral artery and advanced in the patient's vasculature through the aorta AO, shown in FIG. 1A. It should be appreciated that the percutaneous approach is not essential to achieve many of the objects of the invention, and therefore, an open-chest or other approach may also be used. Furthermore, access to a treatment site using a saphenous vein graft (SVG) is also contemplated, as disclosed in assignee's copending application entitled VASCULAR GRAFT BYPASS, application Ser. No. 09/368,483, filed the same date herewith, the entirety of which is hereby incorporated by reference.

Figure 3A:
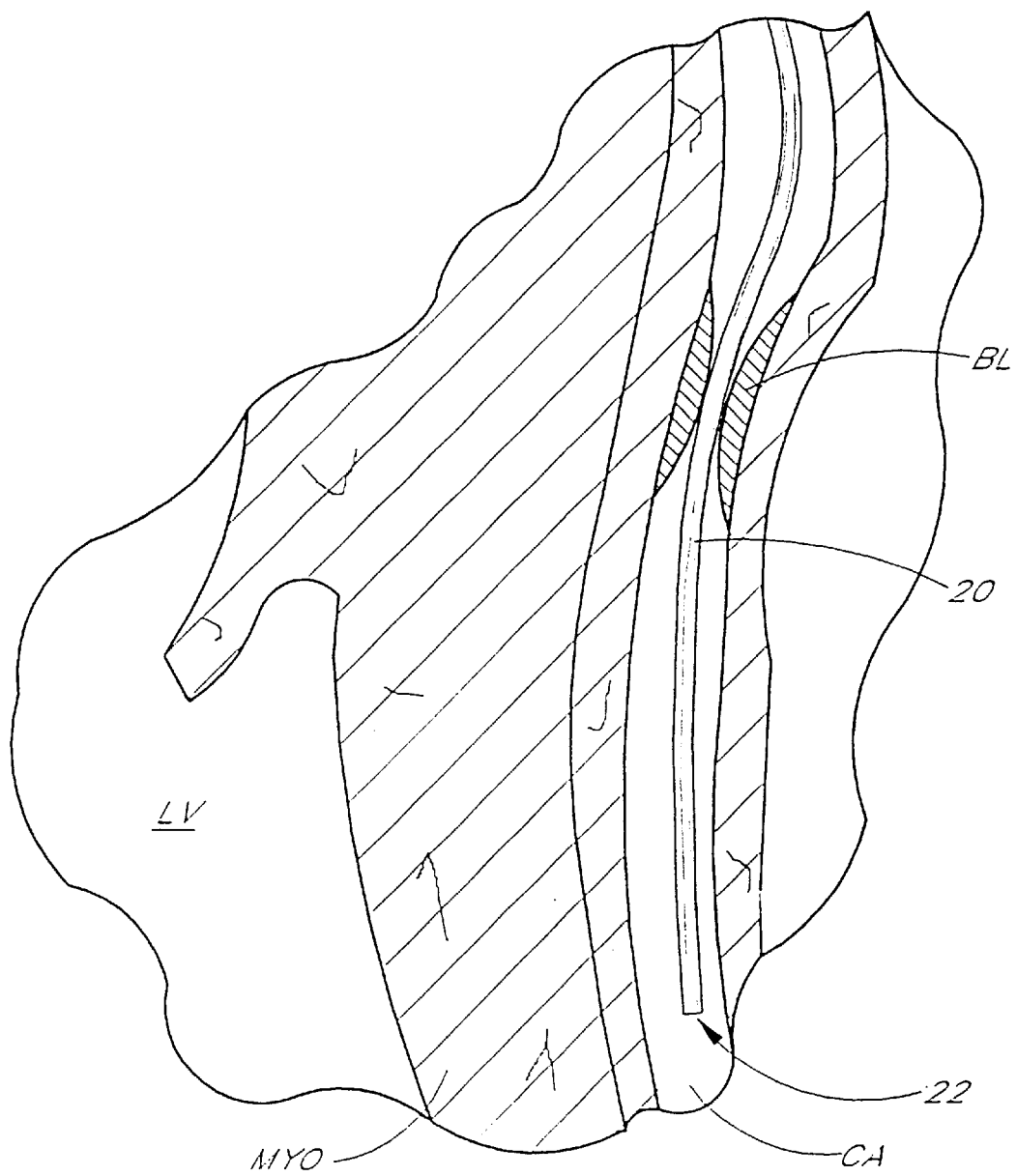
FIG. 3A is a schematic, partial cross-sectional view of a coronary artery adjacent the left ventricle, showing a delivery catheter being advanced through a blockage in the coronary artery.
Figure 3B:
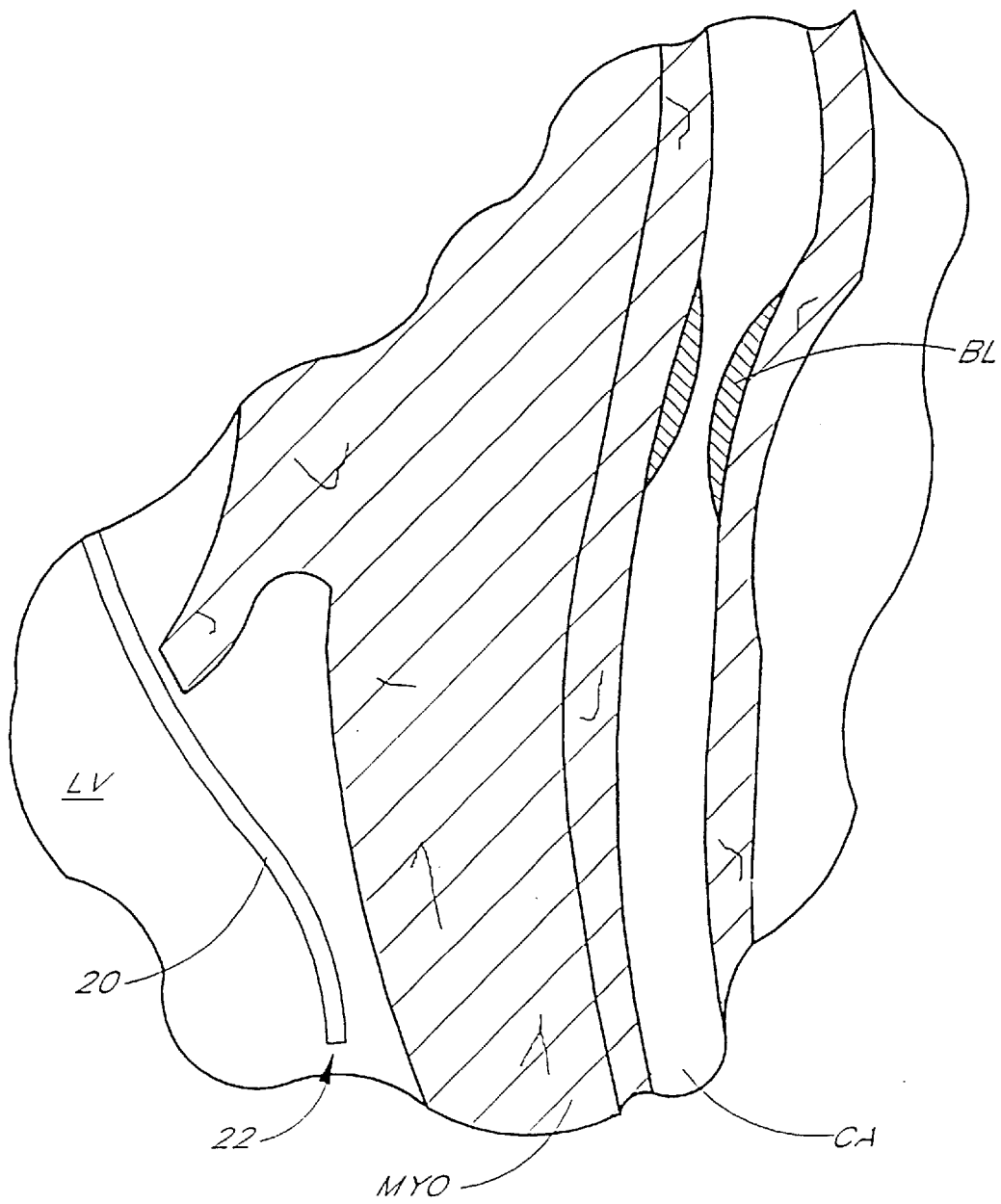
FIG. 3B is a schematic, partial cross-sectional view of a coronary artery adjacent the left ventricle, showing a delivery catheter being advanced into the left ventricle.

As shown in FIG. 3A, an exemplary delivery catheter or guidewire 20 which has been advanced percutaneously, for example, through the femoral artery and through aorta AO is advanced through the blockage BL in the coronary artery CA. The distal tip 22 of the catheter is delivered past the blockage so that it is positioned adjacent to a desired insertion point into the myocardium MYO. FIG. 3B shows an alternative access method wherein the catheter 20 is delivered to a position adjacent the myocardium through the left ventricle LV.

Figure 4A:
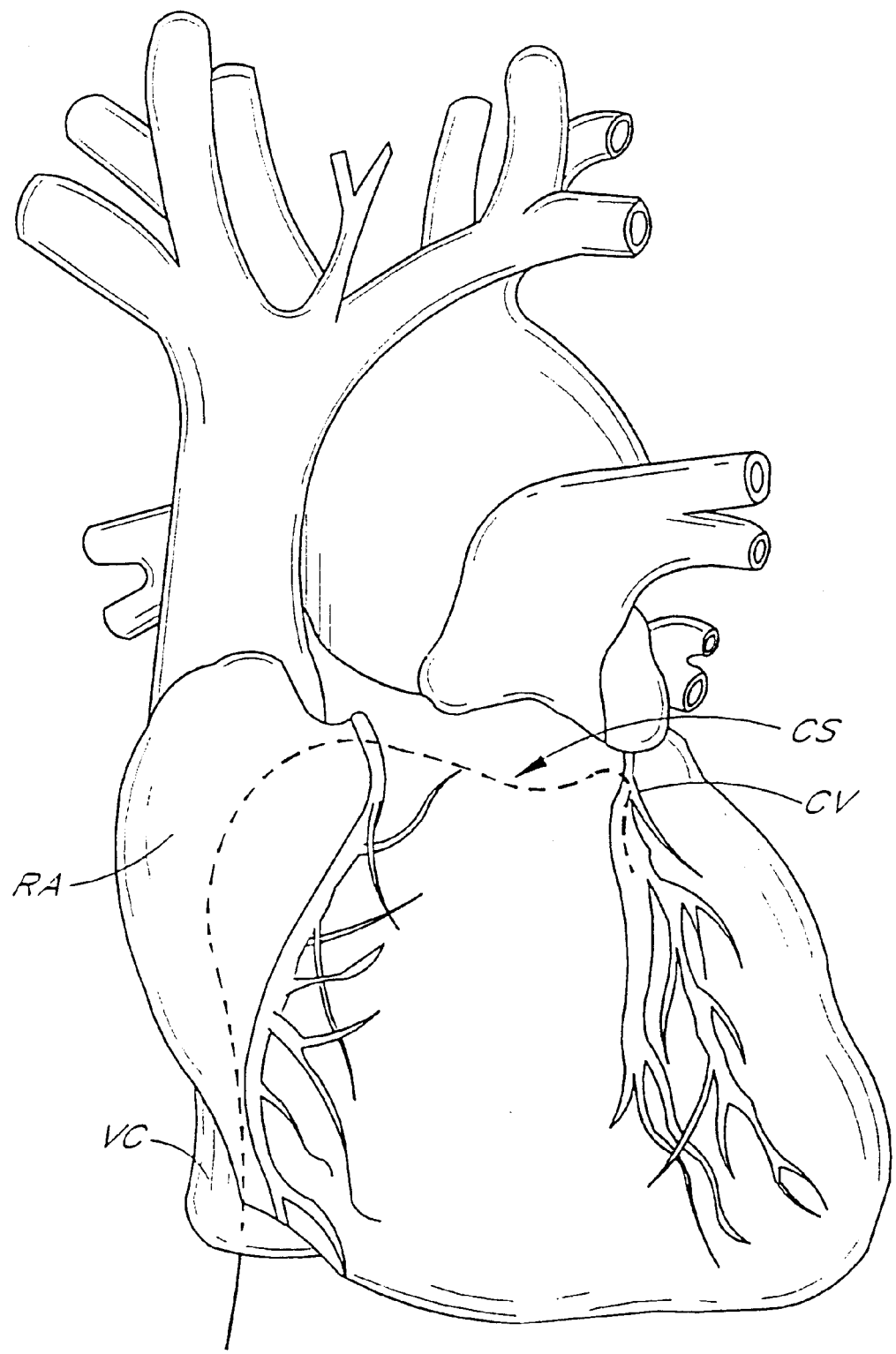
FIG. 4A is a schematic side view of a venous access route through a patient's heart.
Figure 4B:
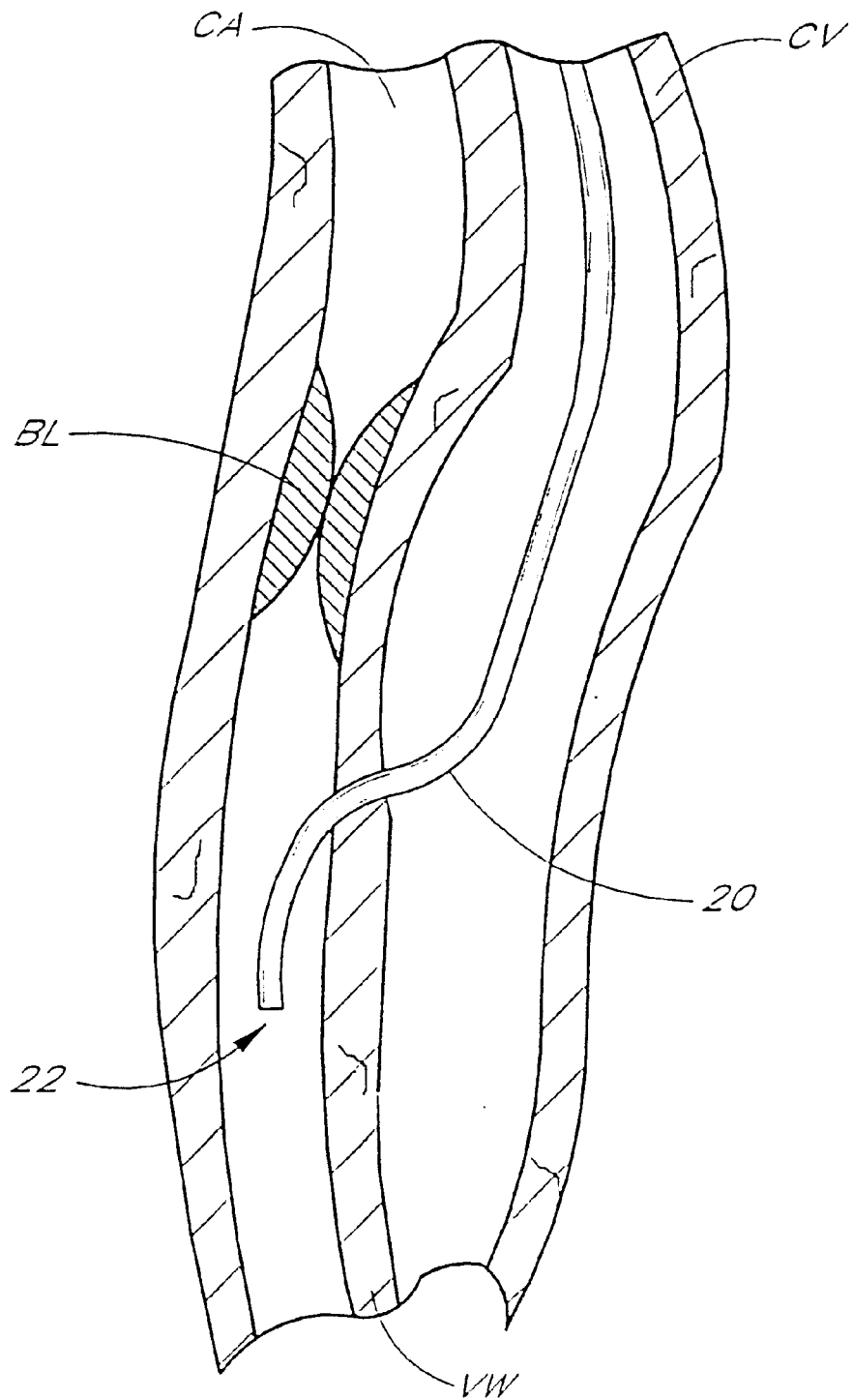
FIG. 4B is a schematic, partial cross-sectional view of the venous access route of FIG. 4A between a coronary vein and a coronary artery, showing a delivery catheter being advanced through the coronary vein into the coronary artery.

FIGS. 4A and 4B depict an alternative access route used when a blockage in the coronary artery is too large for the catheter to be passed therethrough. In this alternate embodiment, a delivery catheter 20 enters the body through an access point preferably in the femoral vein (not shown). The catheter is advanced up the vein to the vena cava VC and into the right atrium RA, as shown in FIG. 4A. Then, the catheter 20 is directed into the coronary sinus CS, and then to the coronary vein CV which runs adjacent to the coronary artery CA.

As shown in FIG. 4B, after the distal tip 22 of catheter 20 is past the blockage BL in the adjacent coronary vein, the delivery catheter 20 is inserted through the vessel wall VW separating the coronary vein CV from the coronary artery CA. Steering of catheter 20 between coronary vein CV and coronary artery CA may be accomplished using the methods and apparatus for turning catheters discussed in further detail below, or other suitable methods. As described in further detail below, the delivery catheter is turned toward the myocardium MYO either for insertion into the myocardium or for directing a guidewire to puncture therethrough. Access to the insertion point may also be accomplished by steering the delivery catheter through the coronary artery CA to a point proximal to the blockage, directing the catheter into the coronary vein to bypass the blockage, and reinserting the catheter from the coronary vein into the coronary artery past the blockage, as shown in FIG. 4B.

Figure 5:
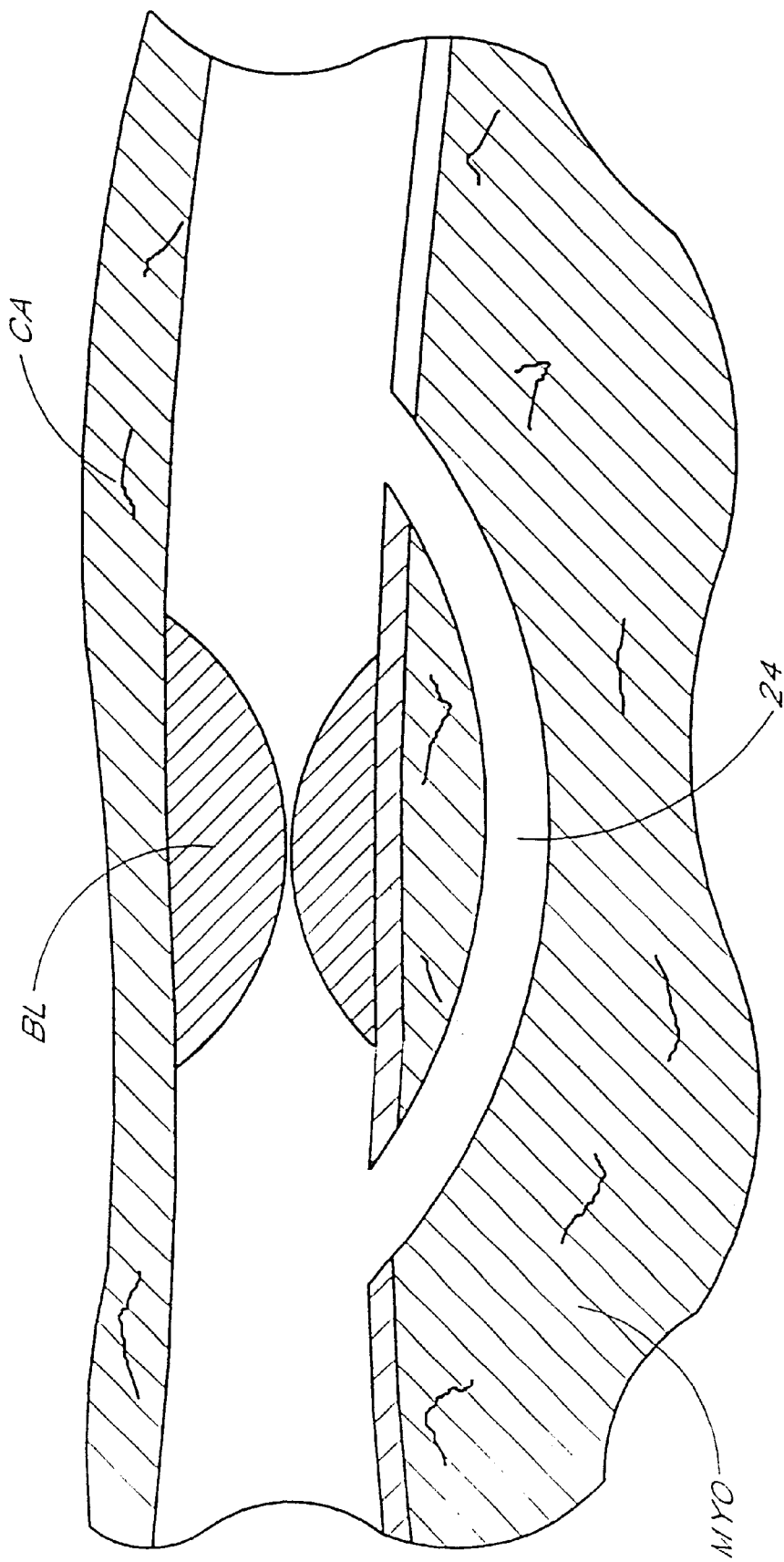
FIG. 5 is a schematic, partial cross-sectional view of a coronary artery adjacent the left ventricle, showing a tunnel formed through the myocardium to bypass a blockage in the coronary artery.
Figure 6:
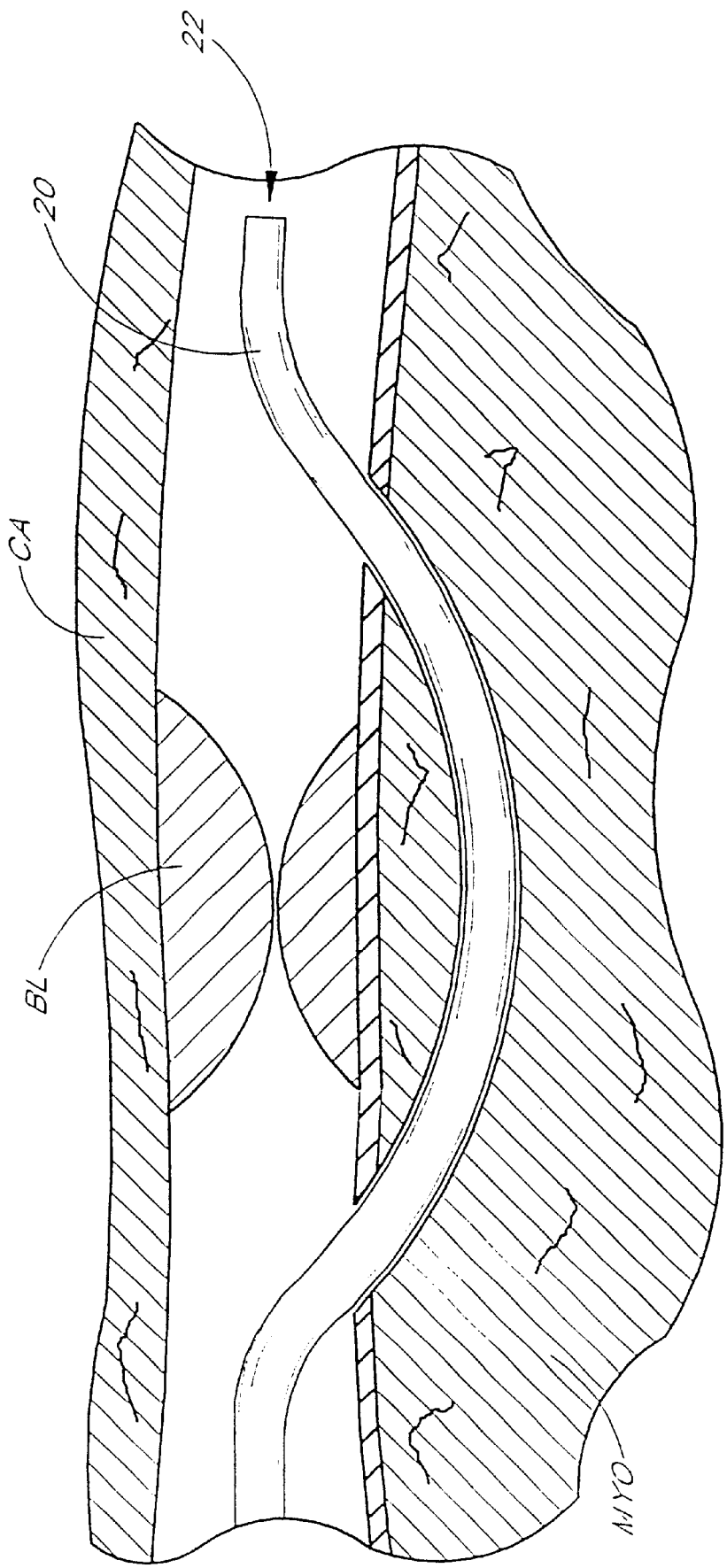
FIG. 6 is a schematic, partial cross-sectional view of a coronary artery adjacent the left ventricle, showing a delivery catheter being advanced through a tunnel formed through the myocardium.

An alternative method of accessing the myocardium MYO when the blockage BL is too large to pass a catheter therethrough employs creating a channel around the blockage. As illustrated in FIG. 5, a tunnel 24 is created from the coronary artery CA into the myocardium MYO at a point proximal to the blockage BL. The tunnel may be created using radiation, lasers, or a surgical drill, or any other suitable methods for creating a tunnel. The tunnel 24 extends underneath the blockage BL and connects with the coronary artery CA at a point distal to the blockage BL. As shown in FIG. 6, a delivery catheter 20 is advanced through the coronary artery CA, into the tunnel 24, and back into the coronary artery CA past the blockage BL. It will be appreciated that other methods for diverting a delivery catheter around a blockage may be used, such as directing the catheter through a shunt into the pericardial space outside the coronary artery, as described below. Furthermore, the tunnel 24 may be stented with a shunt to keep the tunnel 24 open, and to provide a bypass around the blockage, as described below.

While the tunnel 24 shown in FIG. 6 is described as providing access to a myocardial insertion point for a coronary bypass, it should also be appreciated that this tunneling technique may be useful for obliteration of the blockage BL. In particular, conventional methods for ablating a blockage only permit access to the blockage from one side. By employing the tunneling method shown in FIG. 6, however, a blockage BL can be treated not only from its proximal end, but also from its distal end simultaneously.

Figure 7A:
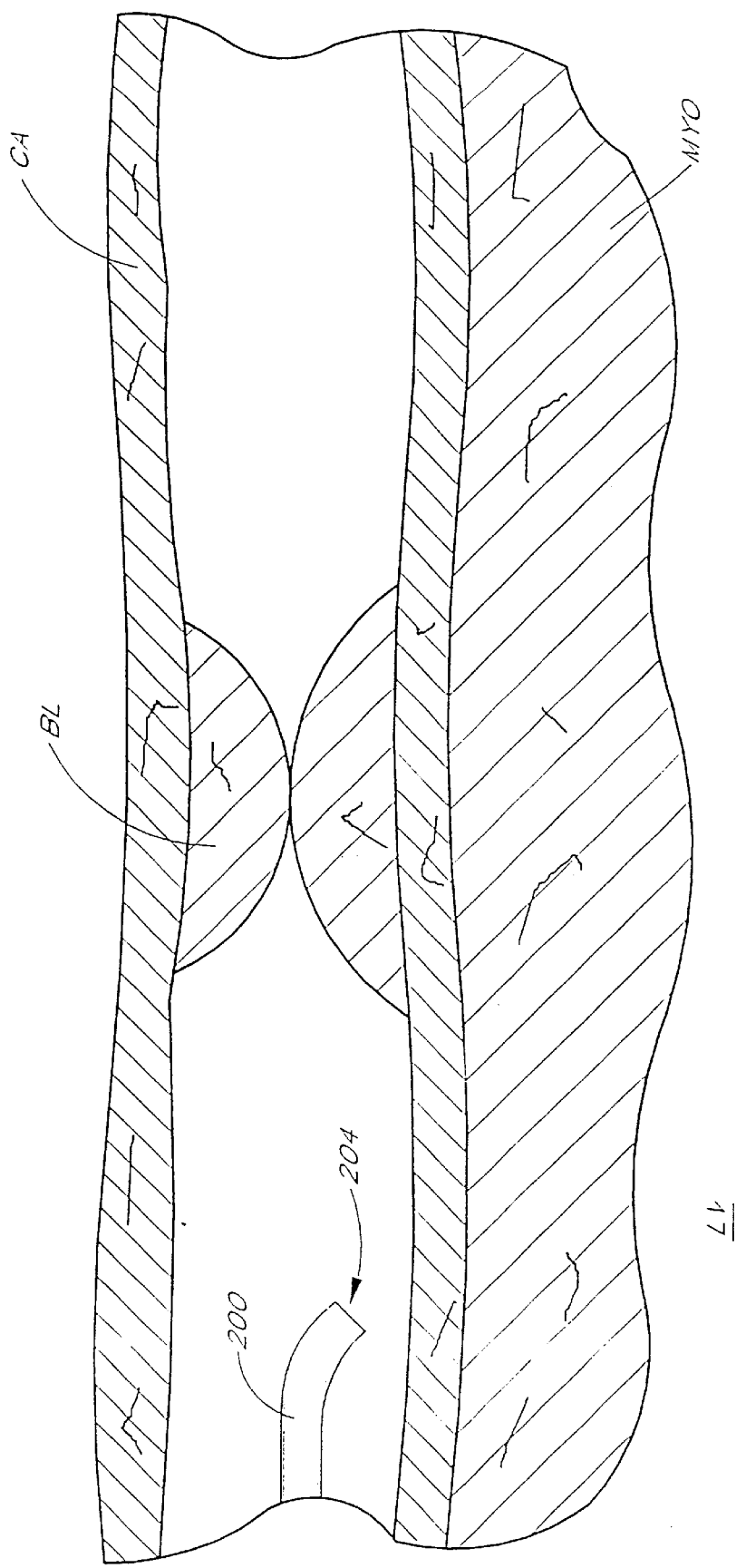
FIGS. 7A–7G are schematic, partial cross-sectional views of a coronary artery with a blockage therein, showing a guidewire method for forming a bypass or access channel through the myocardium around the blockage.
Figure 7B:
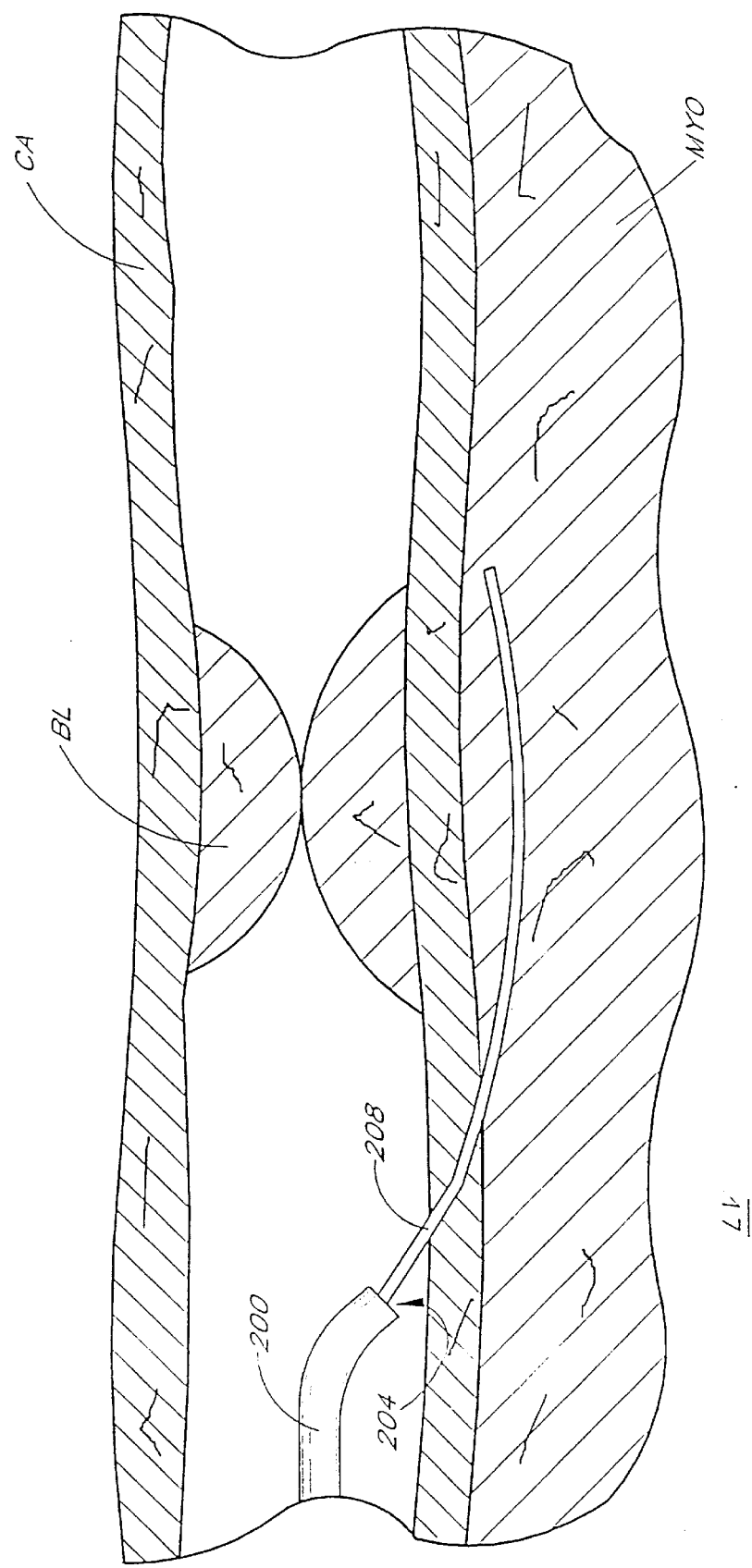
Figure 7C:
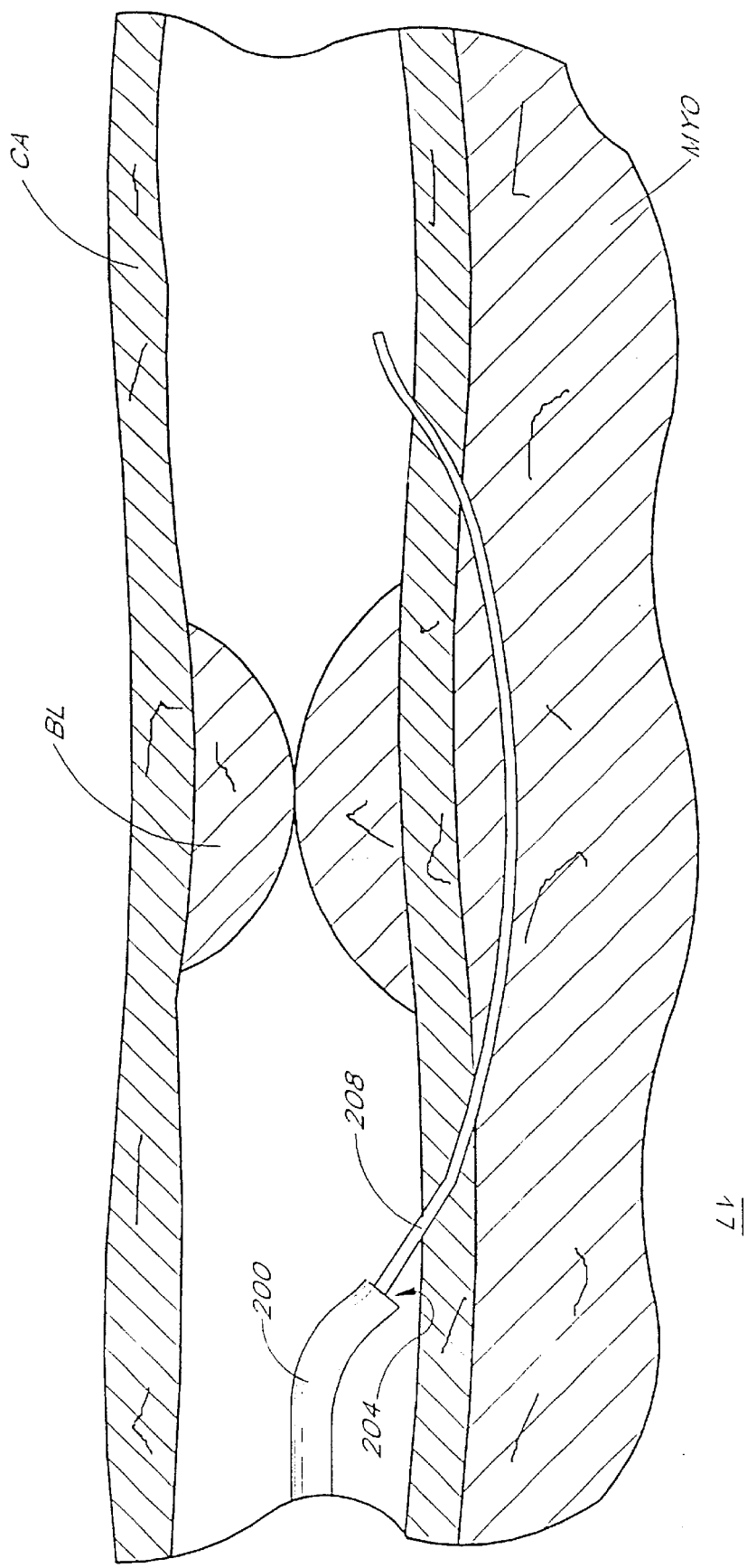

FIGS. 7A–7G illustrate a preferred guidewire method for forming a channel through the myocardium. As shown in FIG. 7A, in this method, a delivery catheter 200 is delivered into the coronary artery CA proximal to the blockage BL. The delivery catheter 200 has a proximal end 202 (not shown) and a distal end 204 and a lumen 206 (not shown) extending therethrough. Using any of the methods described below, or other suitable methods, the distal end 204 of the delivery catheter 200 is turned toward the myocardium MYO. Then, as shown in FIG. 7B, a guidewire 208 exits from the lumen 206 at the distal end 204 of the delivery catheter 200 into the myocardium. This guidewire 208 may be formed of a shape memory alloy material such as nitinol, having a preestablished curved shape that allows the guidewire to curve beneath the blockage BL and out of the myocardium MYO into the coronary artery CA distal to the blockage, as shown in FIG. 7C.

Figure 7D:
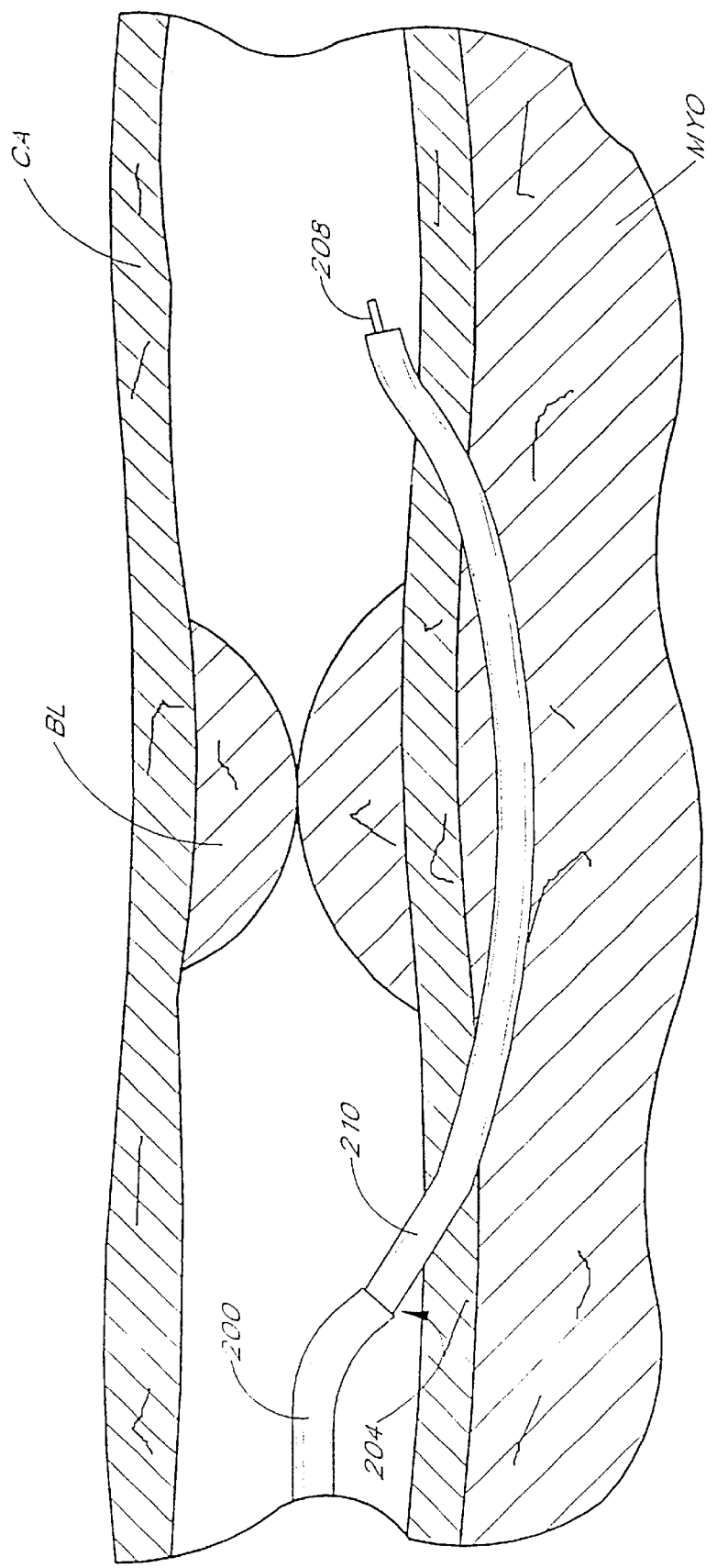
Figure 7E:
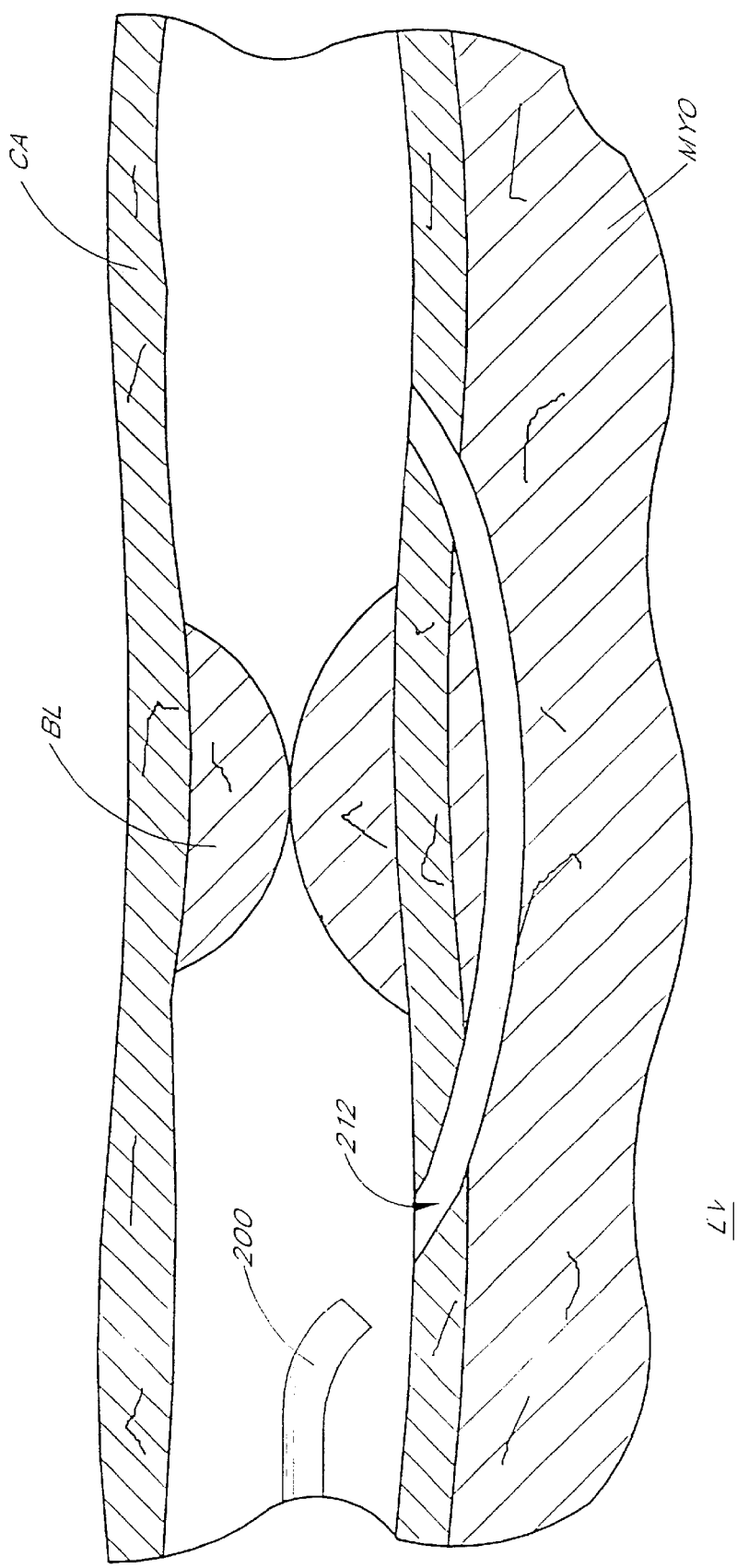

The myocardium MYO is then preferably dilated along the path formed by the guidewire 208 in the myocardium. FIG. 7D illustrates that the myocardium may be dilated by inserting a catheter 210 over the guidewire 208, the catheter 210 effectively forming a pathway through the myocardium. It will be appreciated that other methods for dilating the pathway, including balloons, radiation, drills and lasers, may also be used. Once dilated, a myocardial tract 212 extends from proximal the blockage to distal the blockage, as shown in FIG. 7E.

Figure 7F:
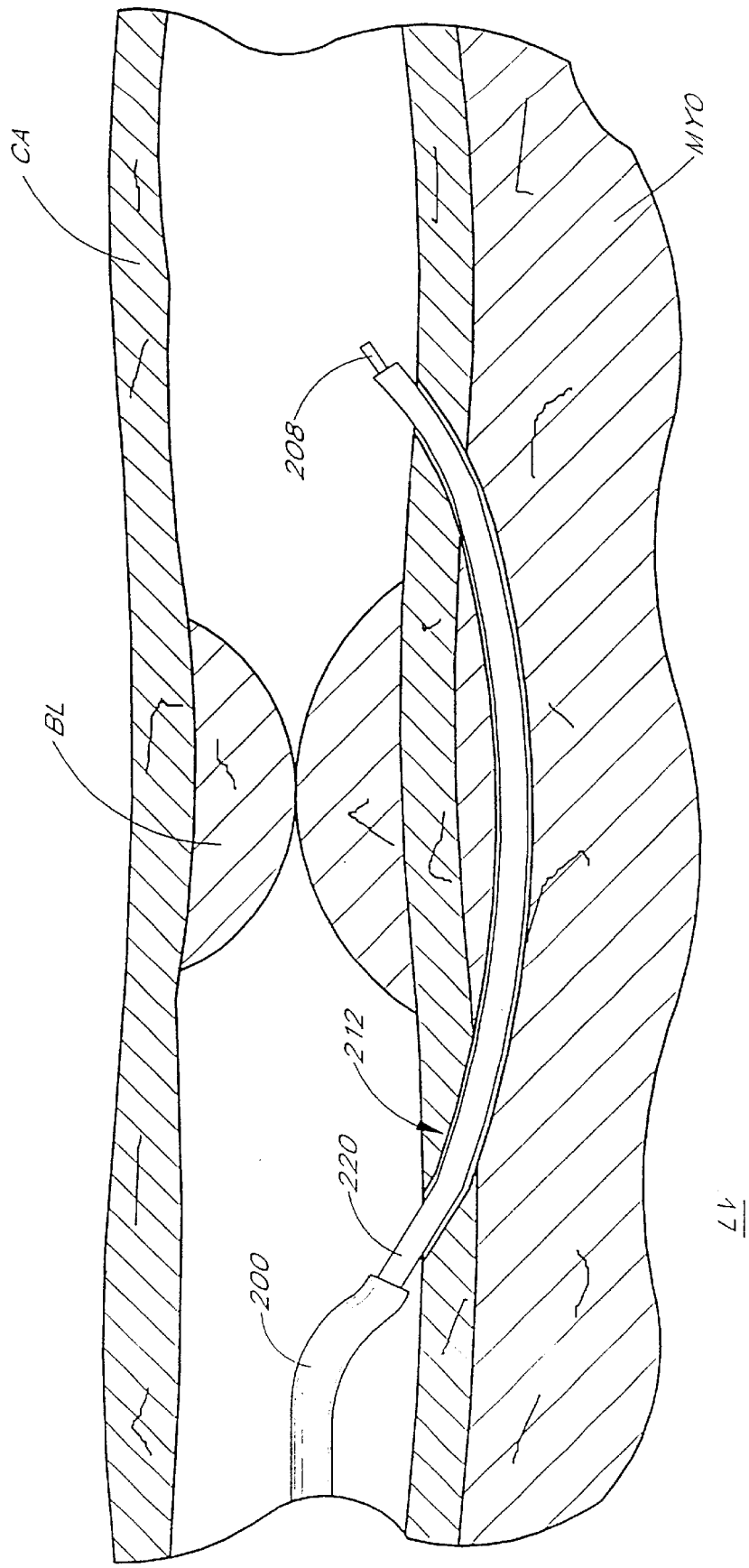
Figure 7G:
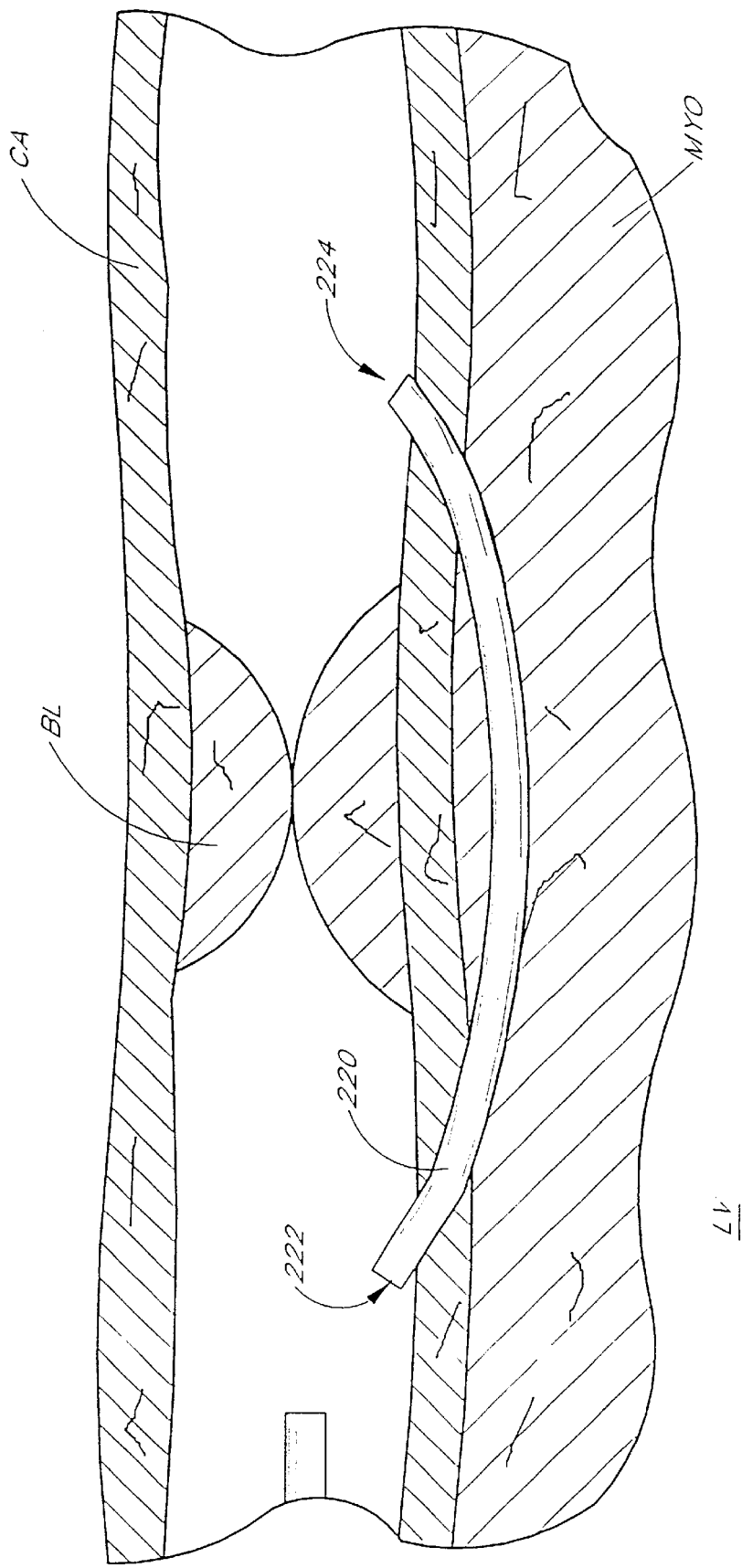

The myocardial tract 212 allows for access to the coronary artery distal to the blockage BL. FIG. 7F further illustrates that this tract 212 may also receive a shunt 220 to keep the tract open. As shown in FIG. 7F, the shunt 220 is preferably delivered through delivery catheter 200, and may be delivered over the guidewire 208. As shown in FIG. 7G, the shunt 220 has a proximal end 222 and a distal end 224 and a lumen 226 (not shown) extending therethrough. In one embodiment, as shown in FIG. 7G, once the shunt is delivered, the proximal end 222 and the distal end 224 both extend out into the flow path of the coronary artery CA. This enables easier guidance of stents and other medical devices through the shunt 220 because devices delivered through the coronary artery need not necessarily be turned into the myocardium MYO. Furthermore, the lumen 226 connecting the proximal end 222 to the distal end 224 may also serve as a blood flow path providing a bypass around the blockage BL.

Figure 8A:
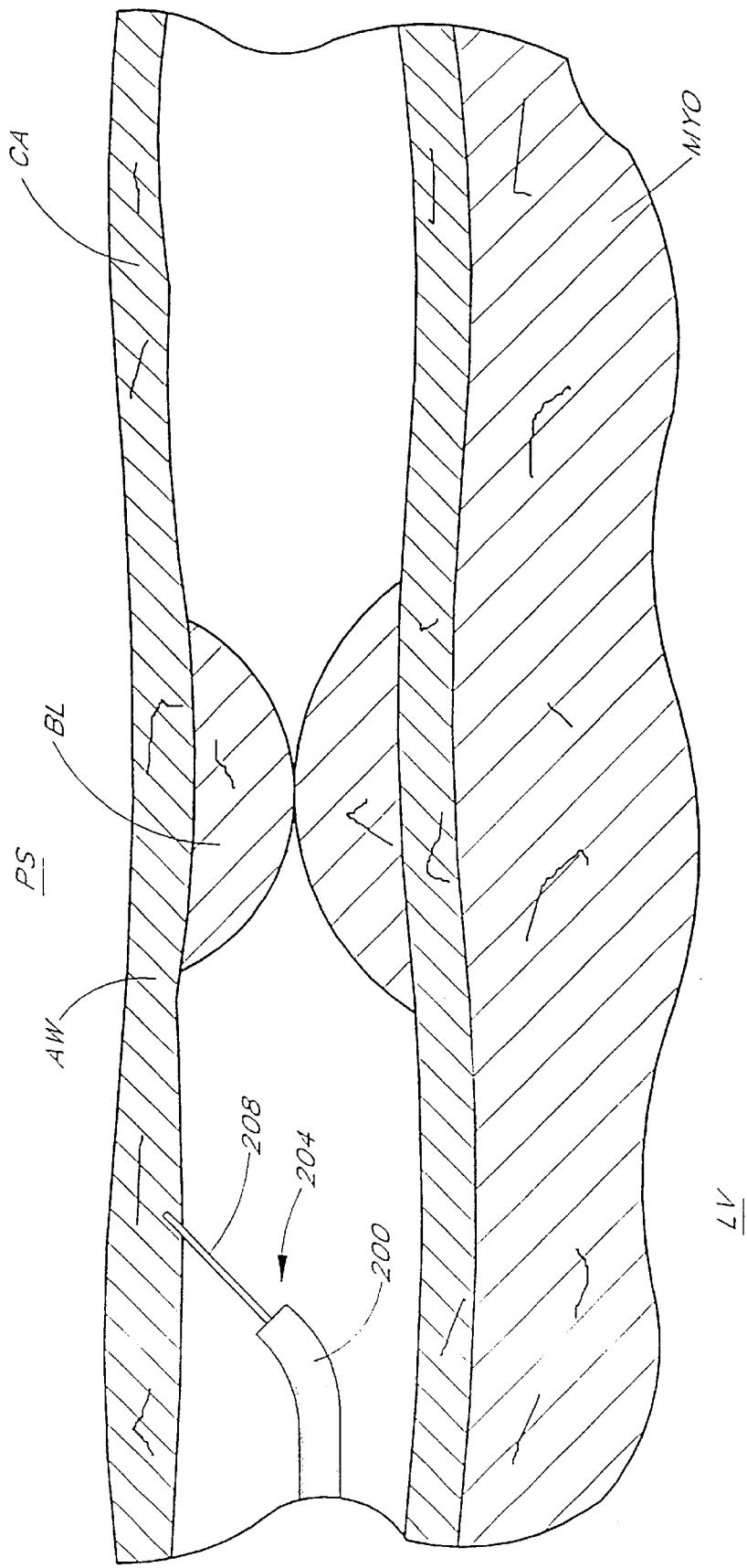

FIGS. 8A–8F depict another method wherein a bypass or access channel is formed through the pericardial space PS around a blockage BL. FIG. 8A illustrates a blockage in a coronary artery CA adjacent the myocardium MYO. A delivery catheter 200, such as described above, is advanced to a point proximal to the blockage in the coronary artery CA. The distal end 204 of the catheter 200 is turned toward the anterior wall AW of the coronary artery, as shown in FIG. 8A. A guidewire 208 extending through the lumen 206 (not shown) of the delivery catheter 200 is advanced out of the distal end 204 and punctures through the anterior wall.

Figure 8B:
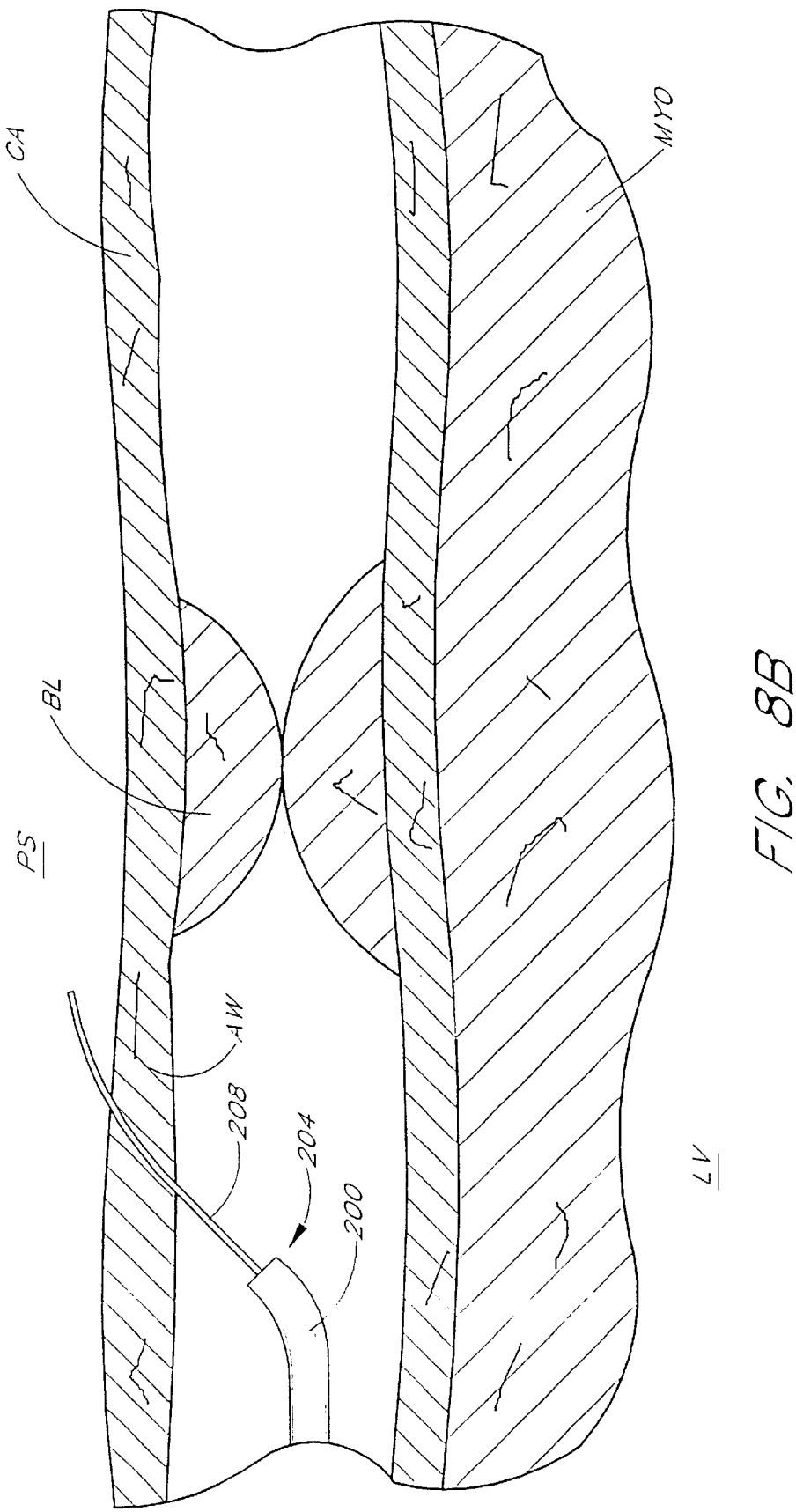
Figure 8C:
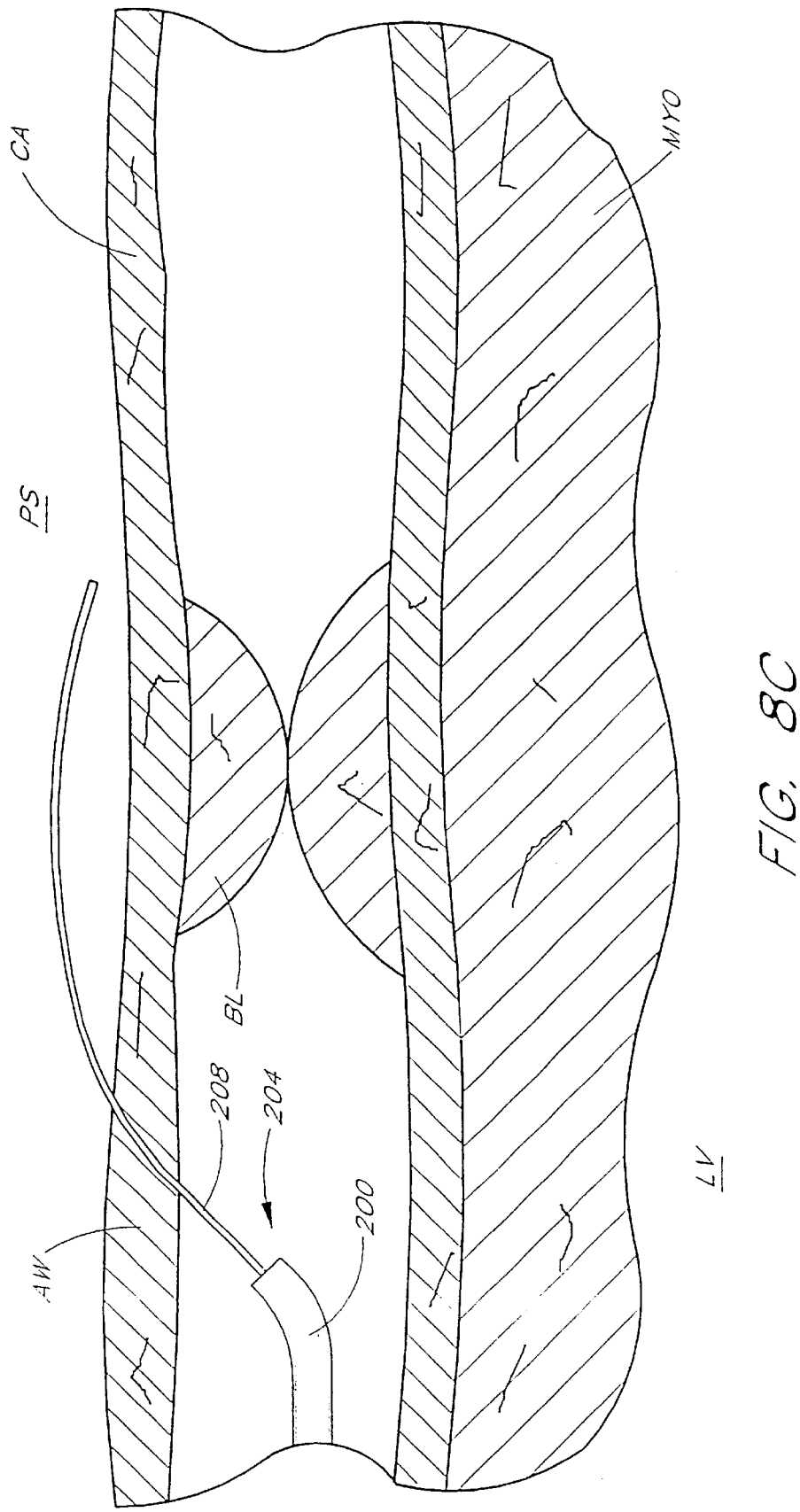

As shown in FIGS. 8B–8C, the guidewire 208 navigates through the pericardial space PS around the blockage BL. The guidewire 208 may be provided with a mini-endoscope to aid in navigation through the pericardial space PS. Turning of the guidewire around the blockage may be accomplished by using a guidewire 208 made of a shape memory alloy material, and providing the guidewire 208 with a preestablished curved shape that will turn the guidewire back into coronary artery CA distal to the blockage. The guidewire may also be turned by using forceps to move the guidewire in the pericardial space.

Figure 8D:
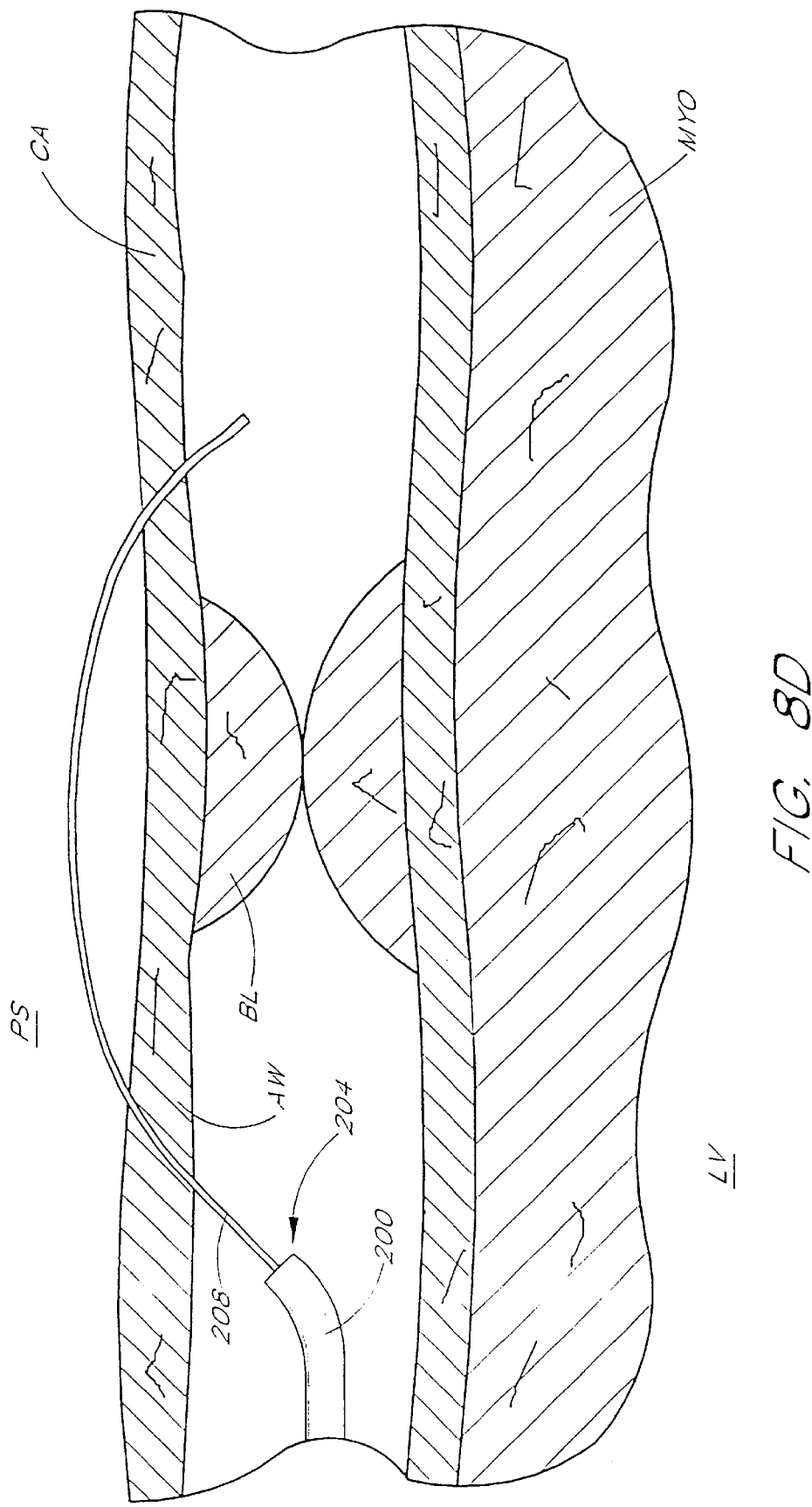
Figure 8E:
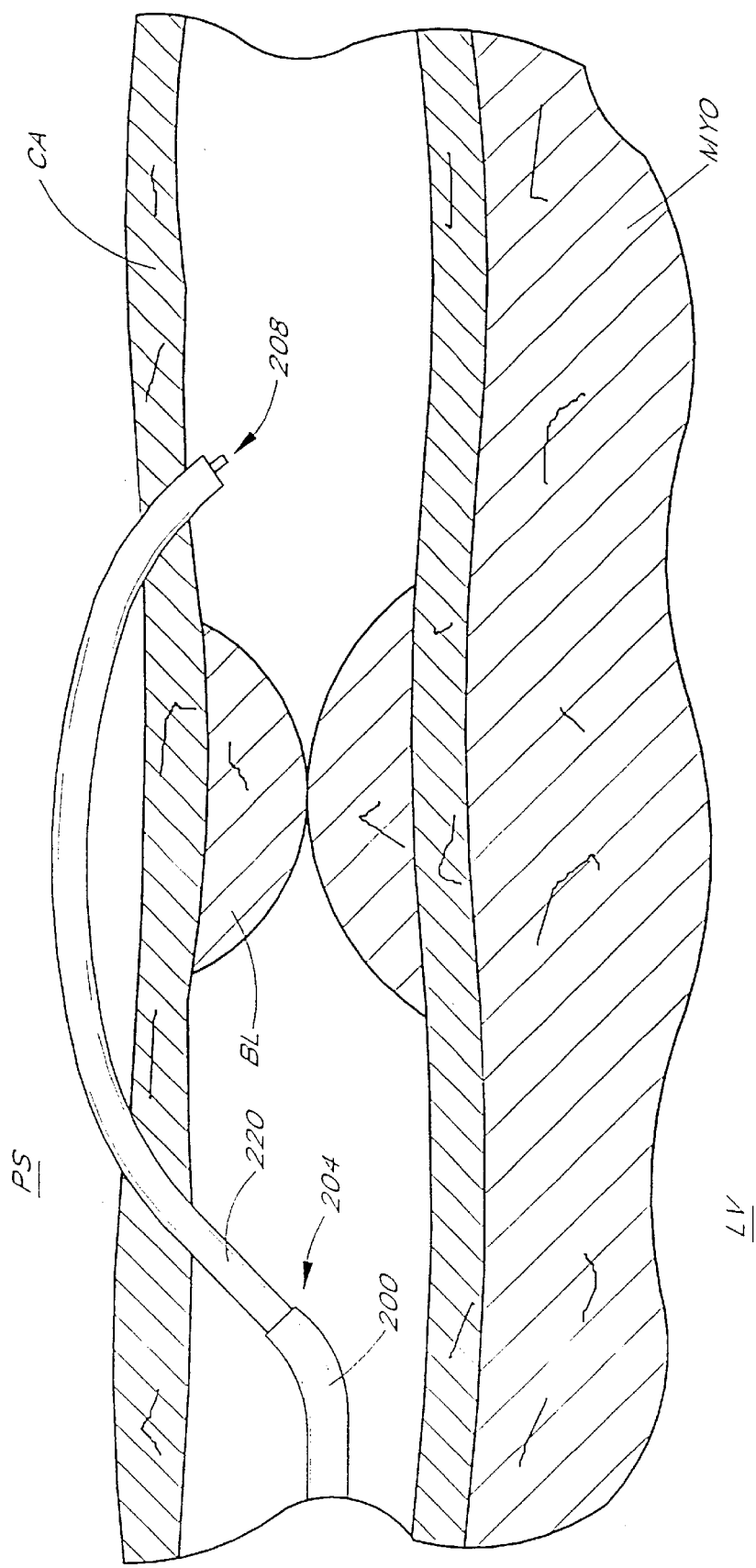

As shown in FIG. 8D, the guidewire 208 reenters the coronary artery CA distal to the blockage BL. A shunt 220, illustrated in FIG. 8E, is then delivered through the coronary artery proximal to the blockage BL, over the guidewire, into the pericardial space PS, and back into the coronary artery distal to the blockage. Once delivered, the shunt 220 has a proximal end 222 and a distal end 224 extending into the flow path of the coronary artery as shown in FIG. 8F. A lumen 226 (not shown) extends between the two ends that provides an access channel to deliver devices to a point distal the blockage in the coronary artery CA. This lumen 226 also may serve as a blood flow conduit to provide a bypass around the blockage.

Figure 9A:
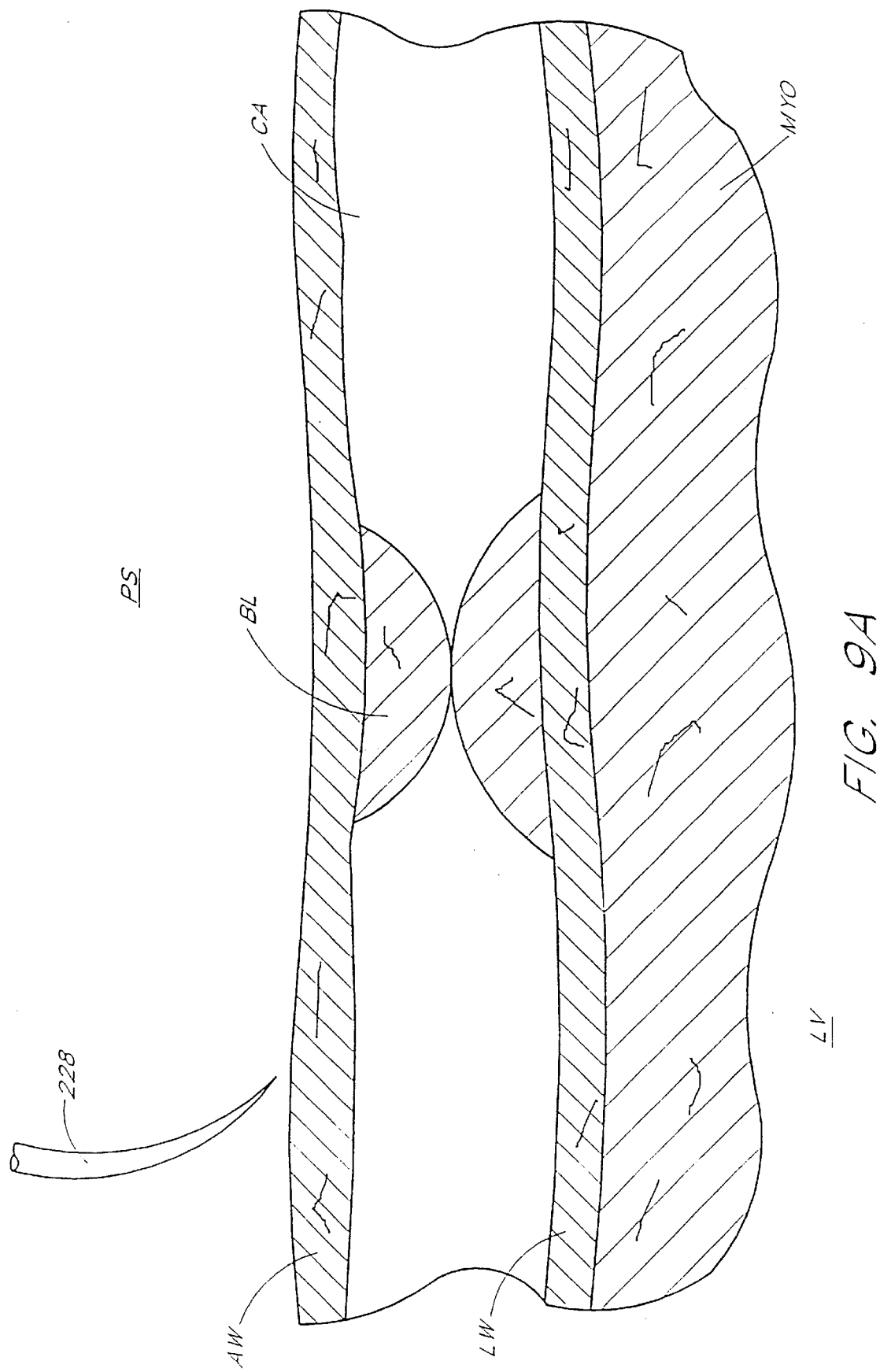
FIGS. 9A–9E are schematic, partial cross-sectional views of a coronary artery with a blockage therein, showing another method for forming a bypass or access channel around the blockage.
Figure 9B:
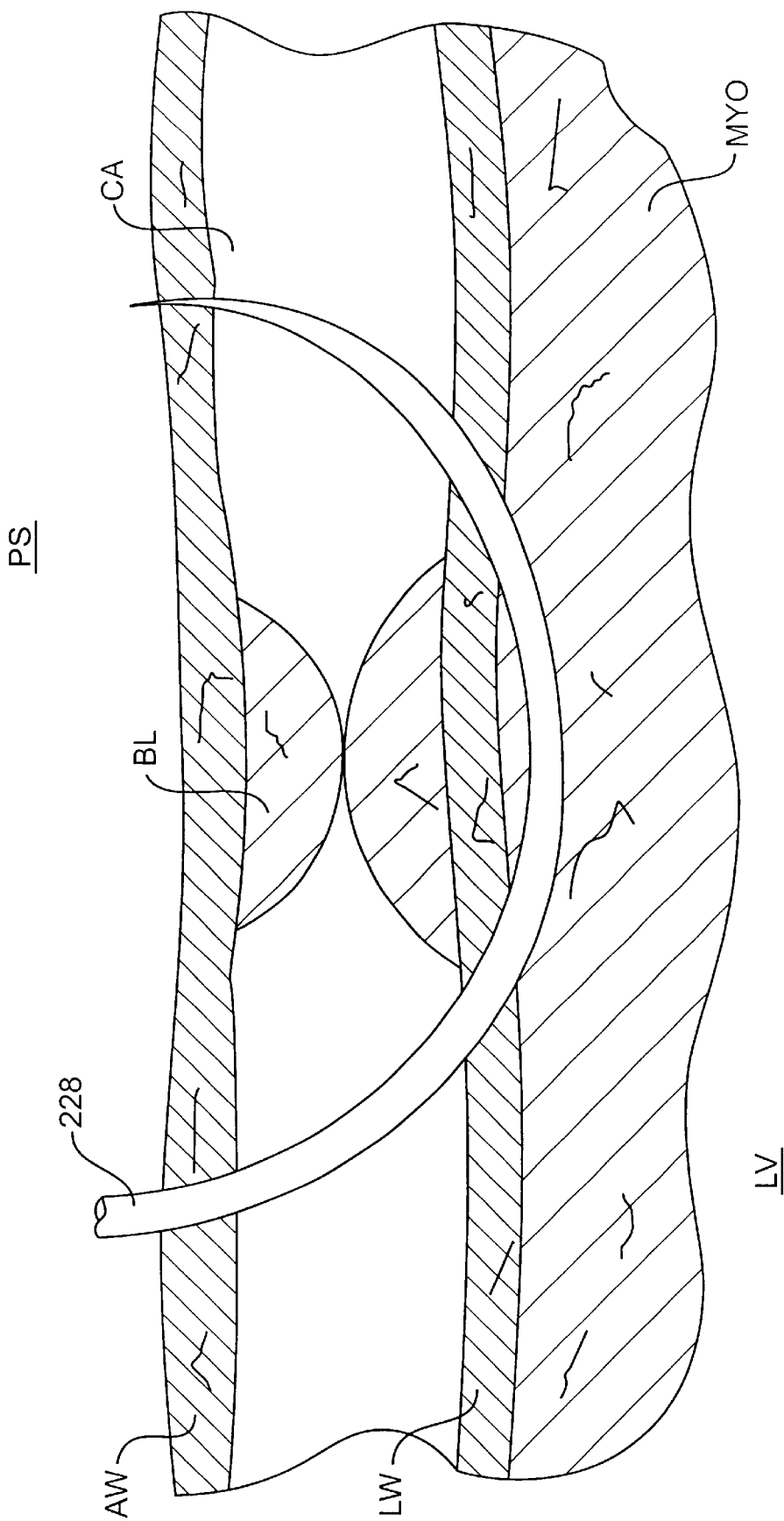
Figure 9C:
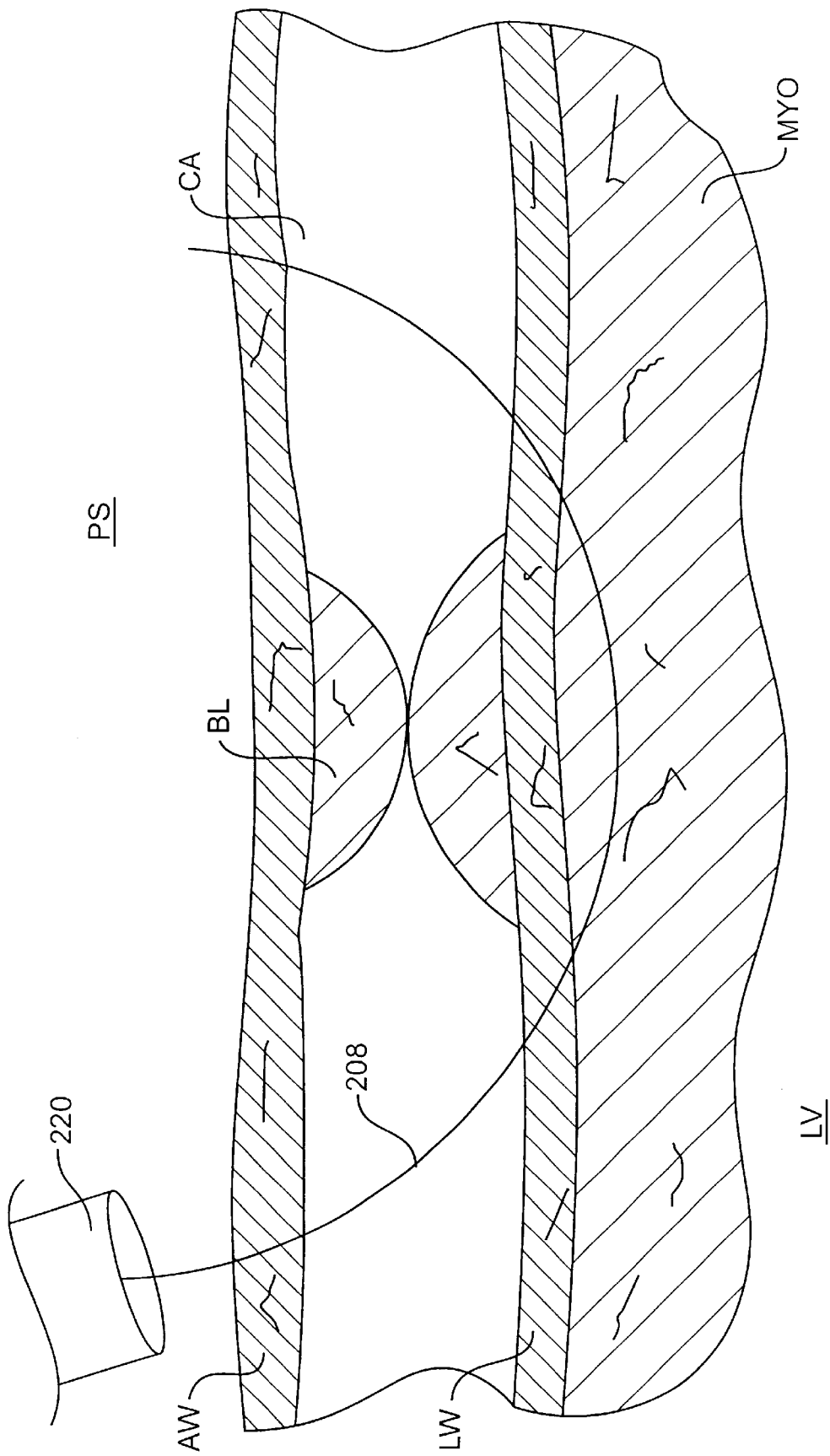
Figure 9D:
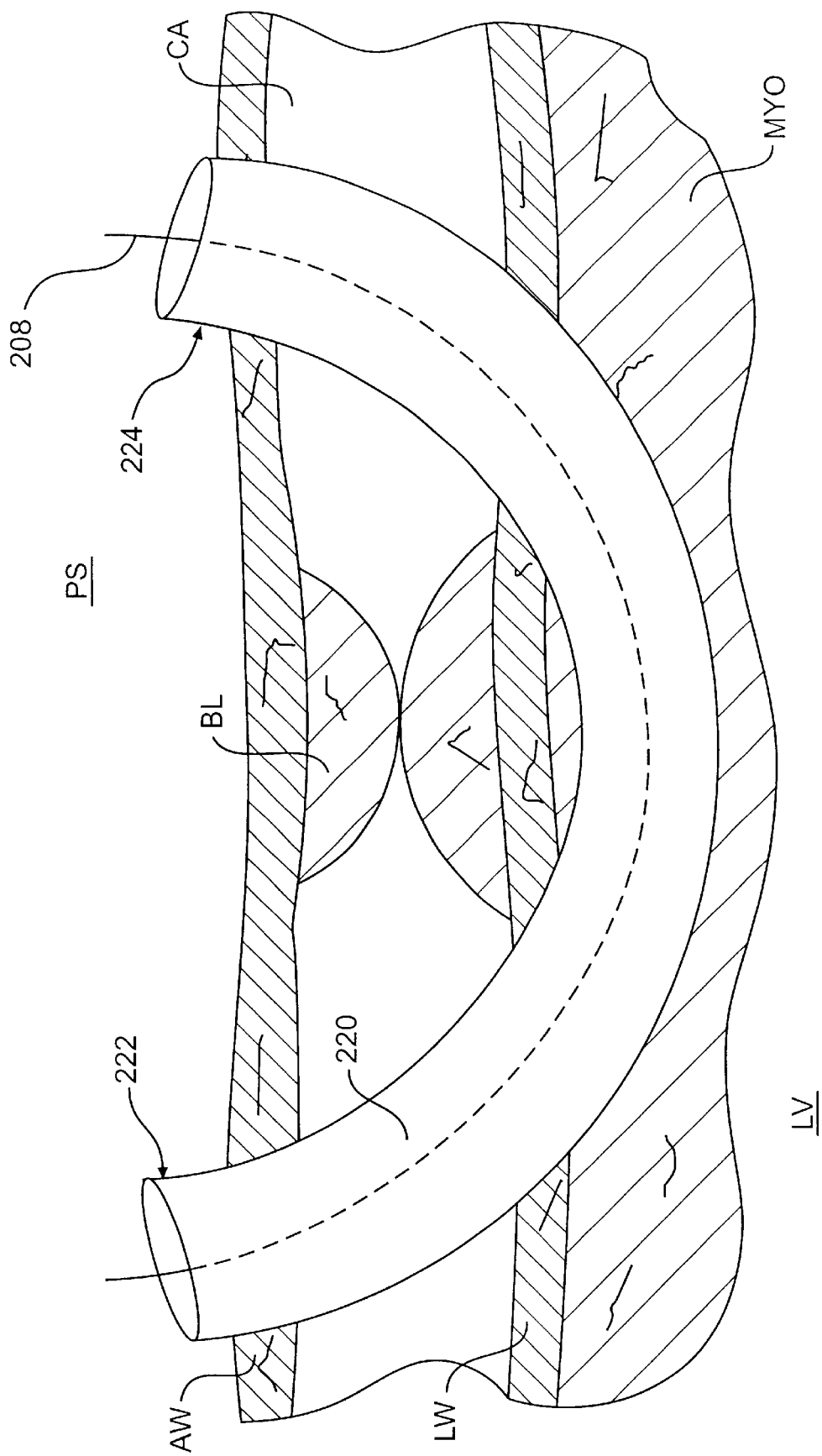
Figure 9E:
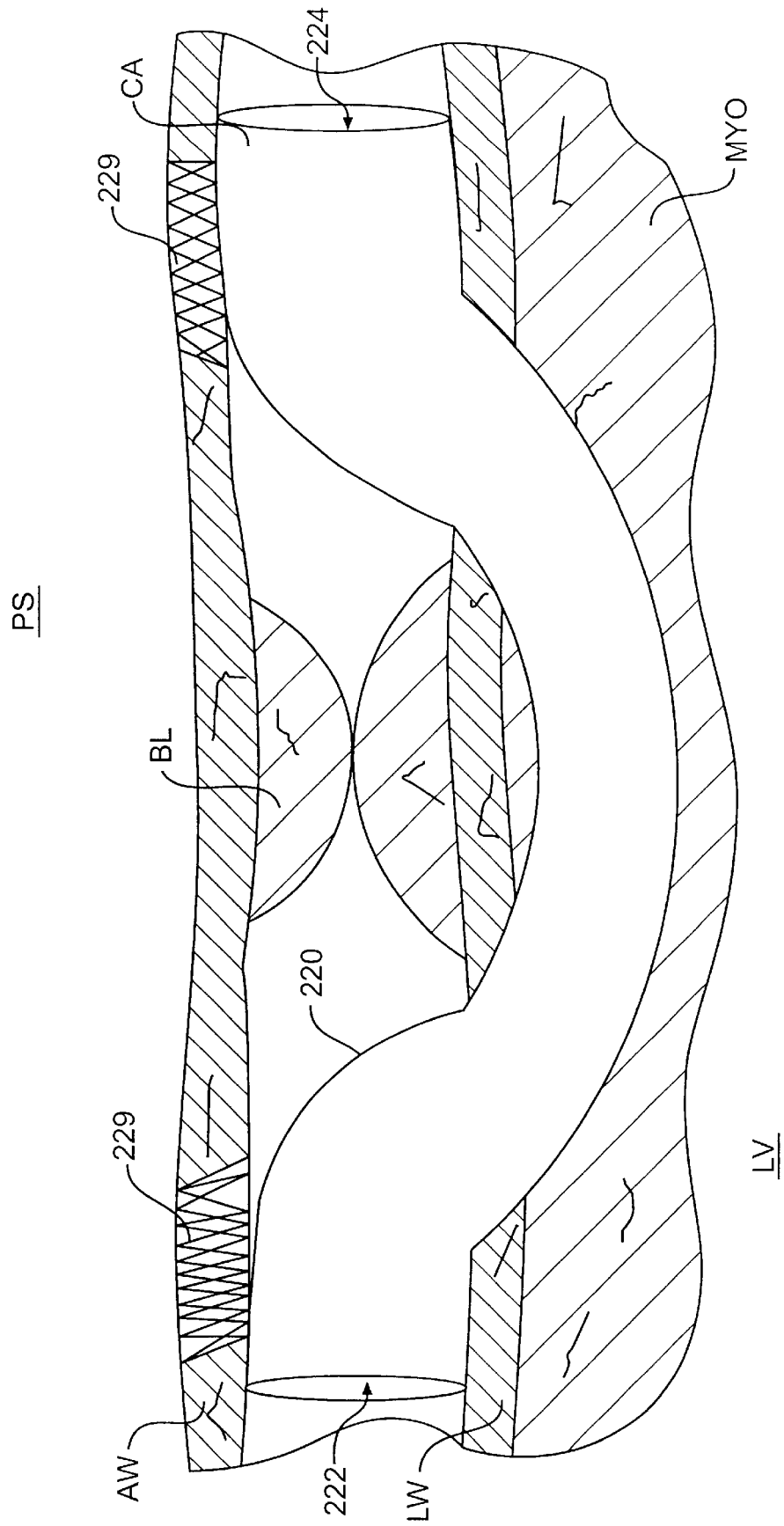

FIGS. 9A–9E illustrate another embodiment for delivering a shunt to create a bypass or access channel around a blockage BL. As shown in FIG. 9A, a needle 228 punctures the anterior wall AW of coronary artery CA from the pericardial space PS. The needle is preferably preshaped in a curved configuration such that when needle 228 is advanced, it punctures the lower wall LW facing myocardium MYO, advances underneath the blockage BL through the myocardium MYO, and curves back out of the myocardium MYO through lower wall LW. The needle 228 then preferably punctures through anterior wall AW into pericardial space PS, as shown in FIG. 9B. The needle 228 is preferably hollow, and allows a guidewire 208 to pass therethrough, as shown in FIG. 9C once the needle has been ignored. A shunt 220 is then advanced over the guidewire 208 until a proximal end 222 of the shunt is in the pericardial space PS proximal to the blockage, and a distal end 224 of the shunt is in the pericardial space PS distal to the blockage, as shown in FIG. 9D. The shunt 220 may be collapsible, and inserted through a delivery tube over the guidewire, or by other methods known to one of skill in the art. As shown in FIG. 9E, the guidewire 208 is removed, and the proximal and distal ends 222 and 224, respectively, of the shunt are moved into the coronary artery CA to complete the blood flow conduit around the block BL. The openings formed in the anterior wall due to puncturing by the shunt is preferably closed with sutures 229 or by other closure means.

Figure 10A:
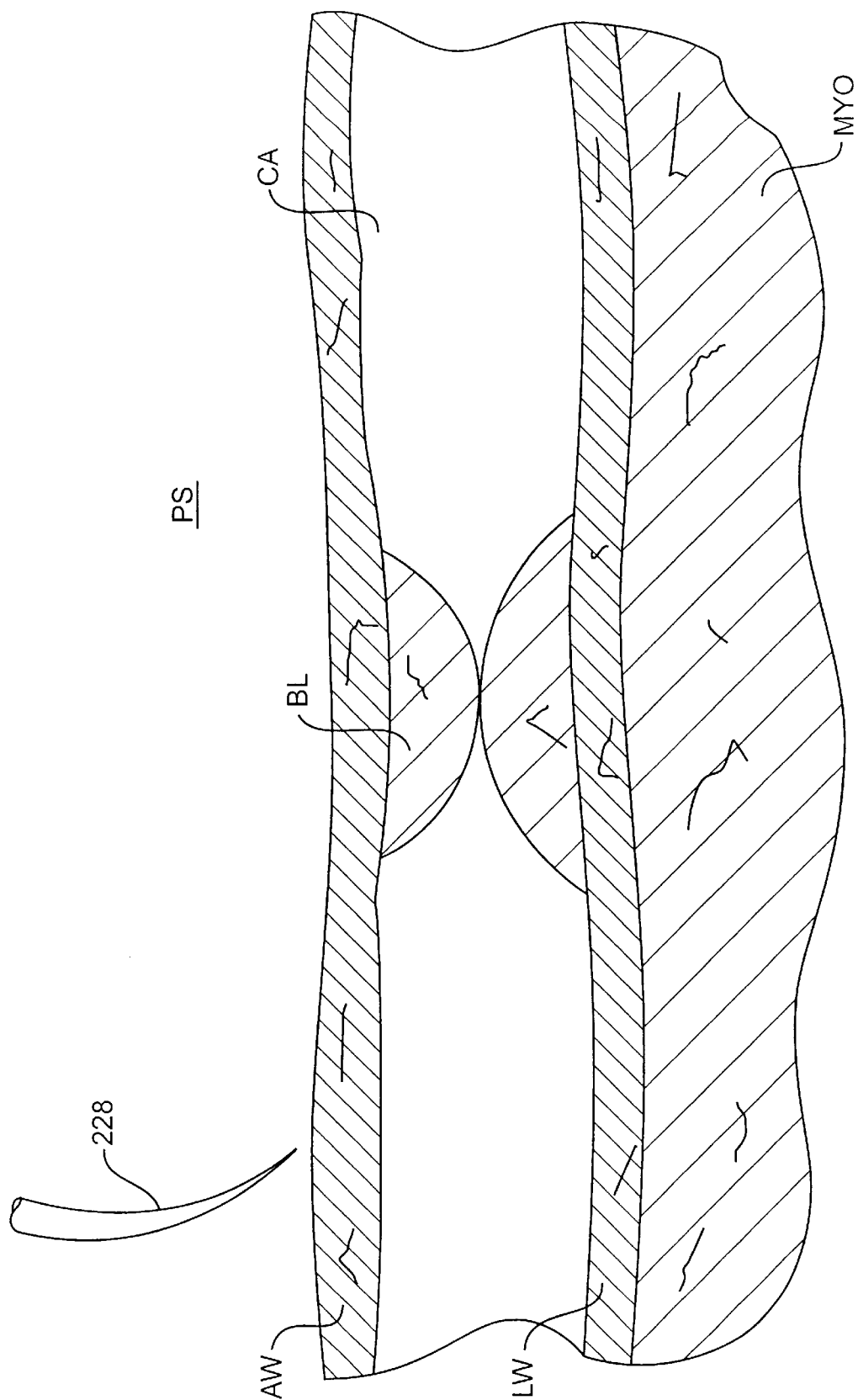
FIGS. 10A–10E are schematic, partial cross-sectional views of a coronary artery with a blockage therein, showing yet another method for forming a bypass or access channel around the blockage.
Figure 10B:
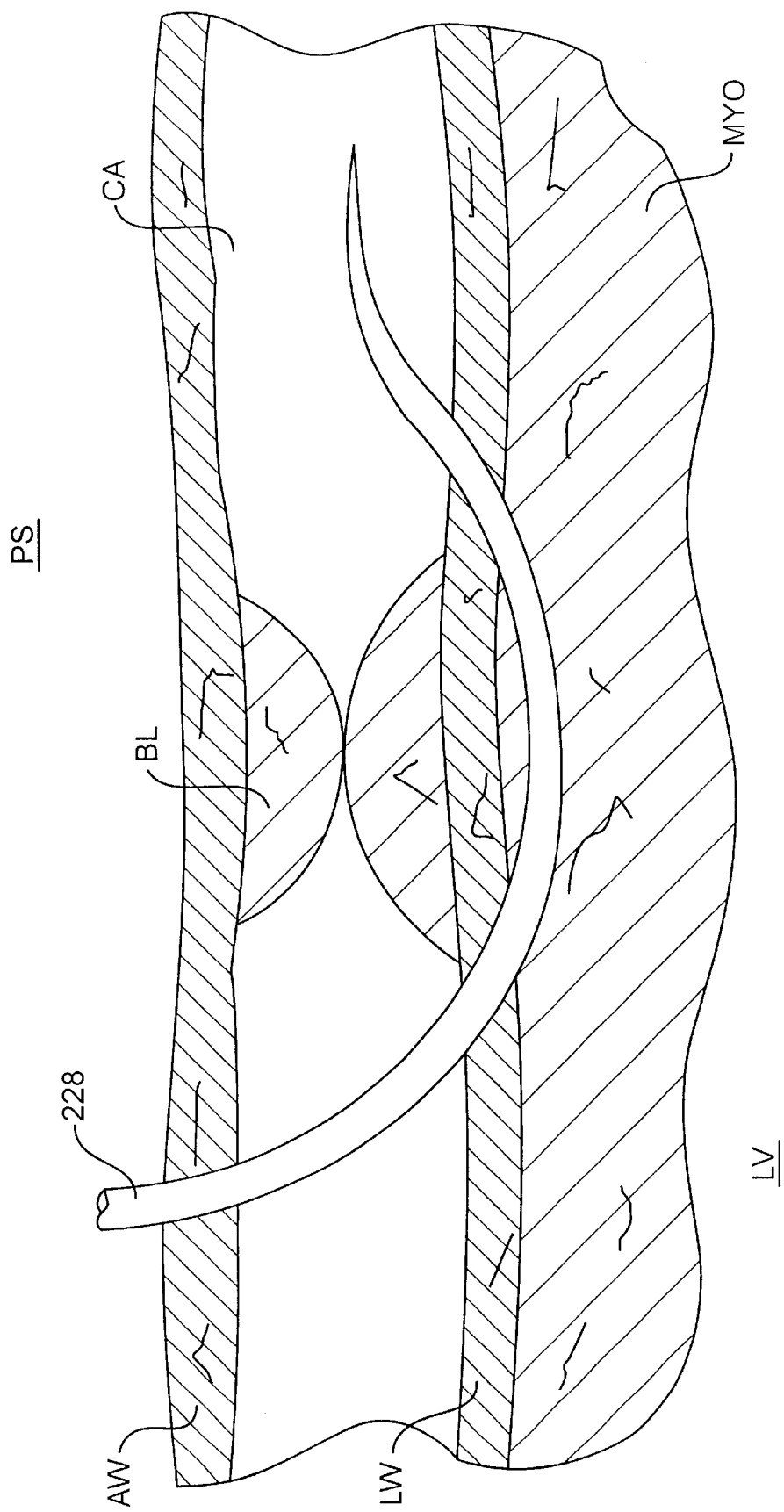
Figure 10C:
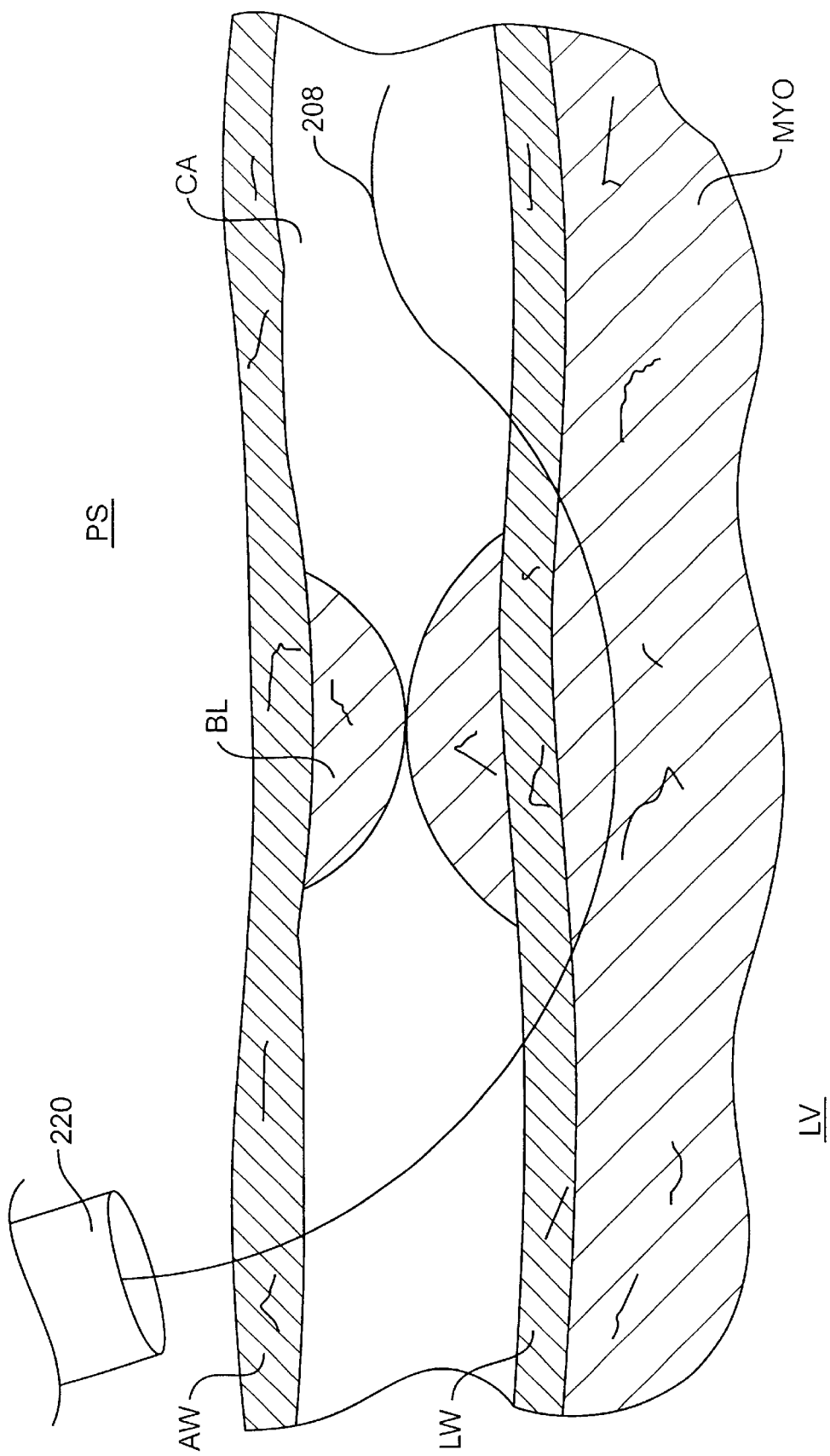
Figure 10D:
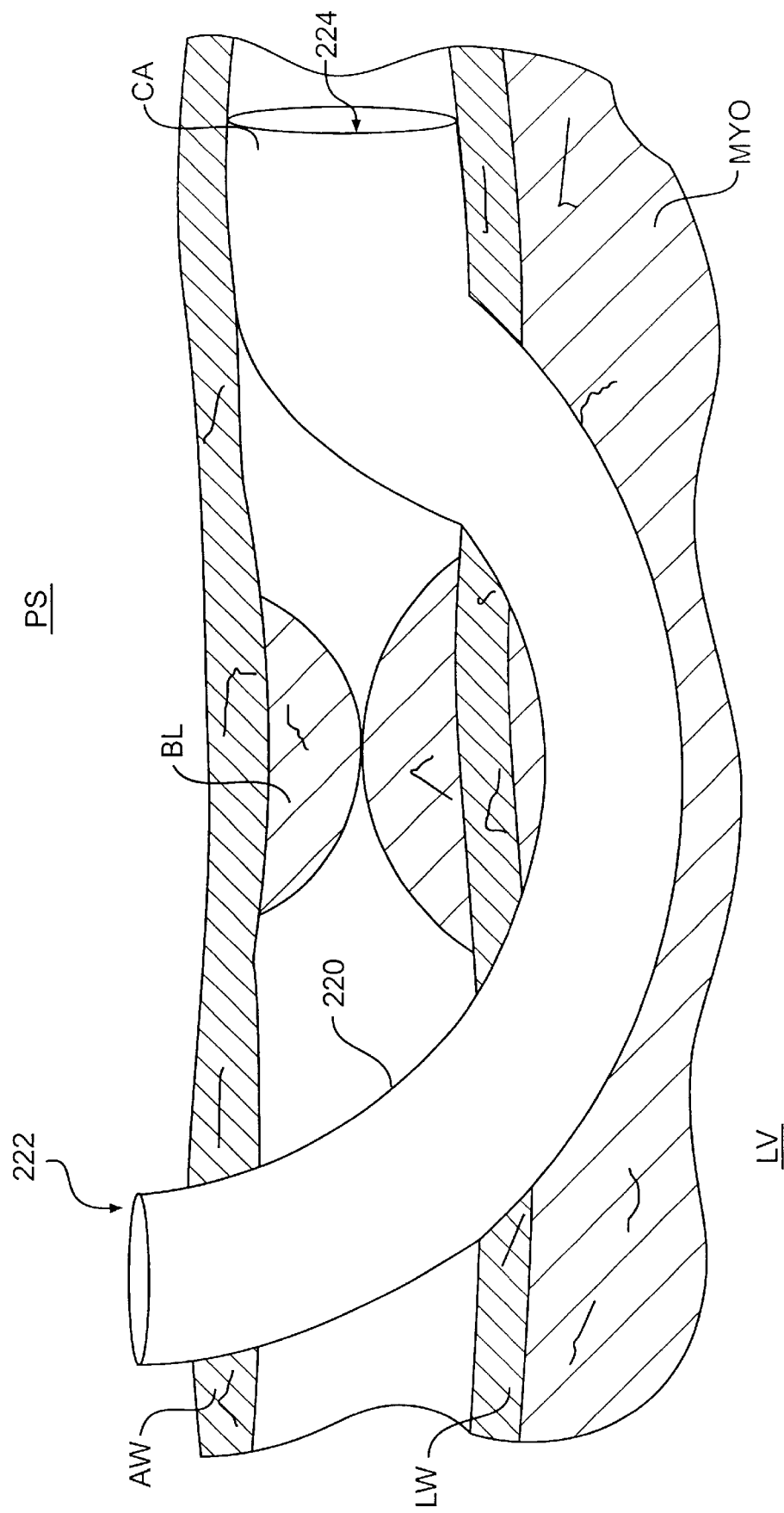
Figure 10E:
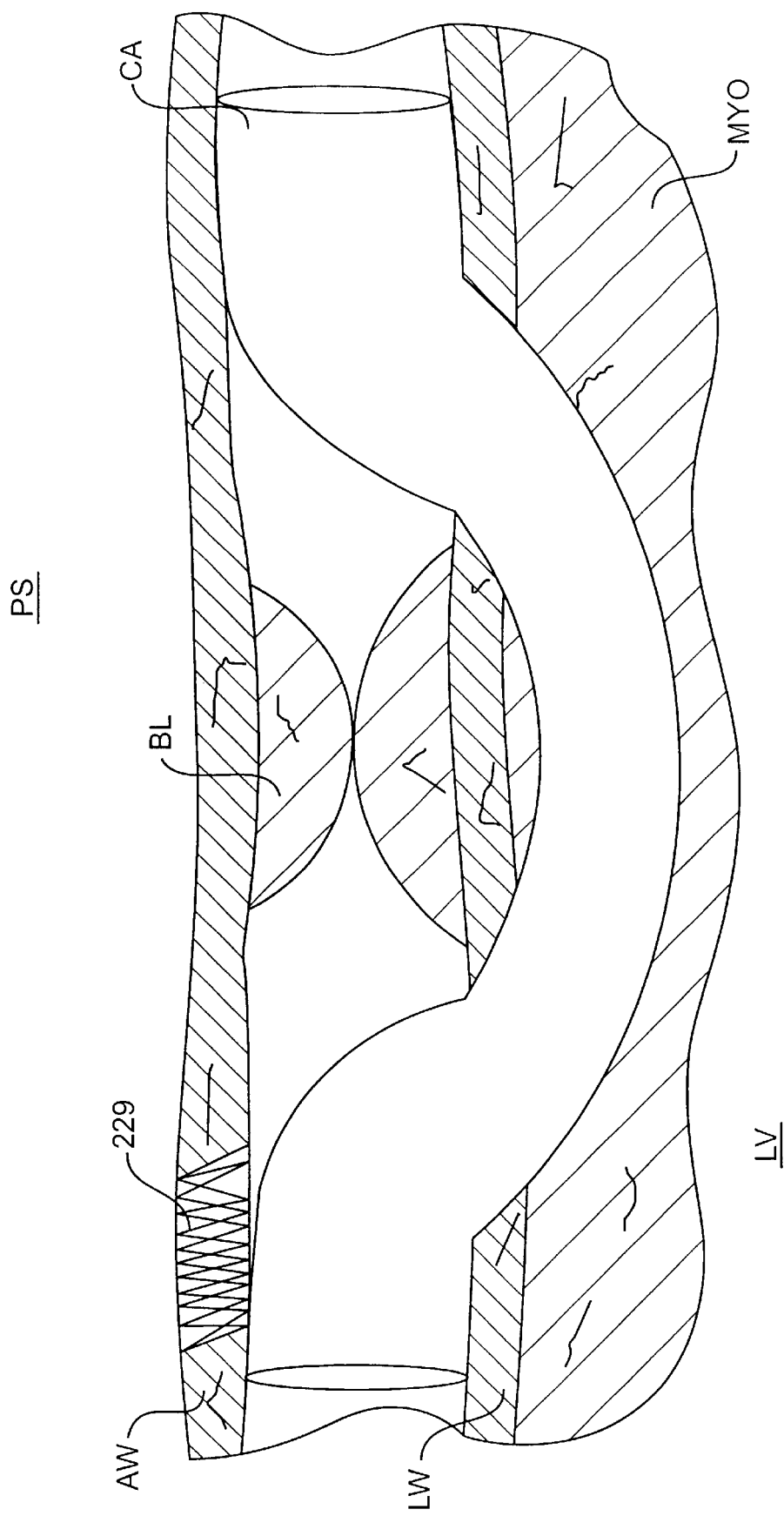

FIGS. 10A–10E illustrate a similar technique for creating a conduit around a blockage, except as shown in FIG. 10B, the needle 228 is advanced until its distal tip is in the coronary artery rather than out in the pericardial space PS. Then, after the guidewire 208 is advanced and the needle is removed (FIG. 10C), the shunt 220 is advanced such that distal end 224 is placed in the coronary artery CA. As shown in FIG. 10E, only proximal end 222 then need be moved out of the pericardial space PS into the coronary artery CA, with sutures 229 preferably closing the artery.

Figure 11A:
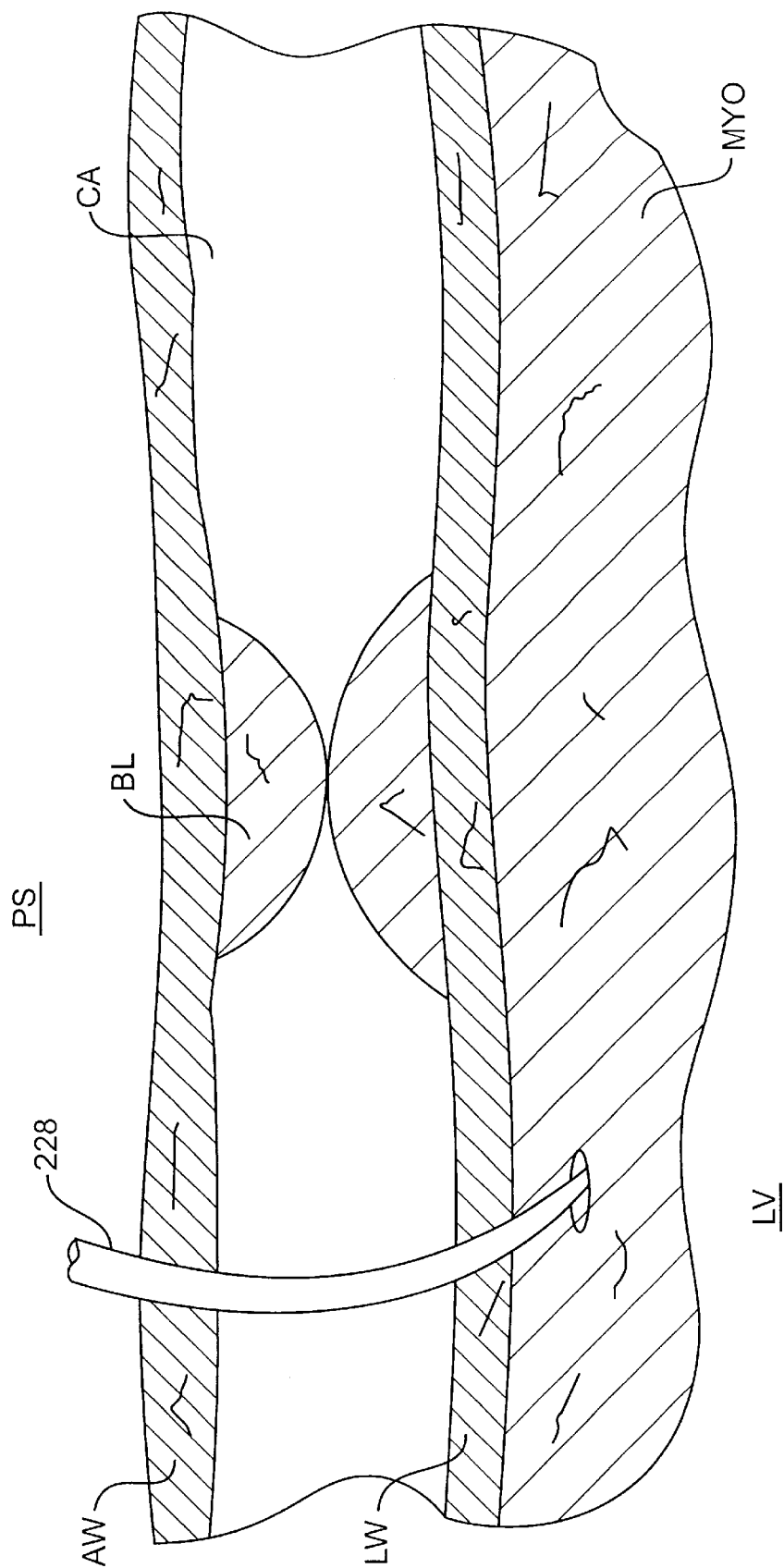
Figure 11B:
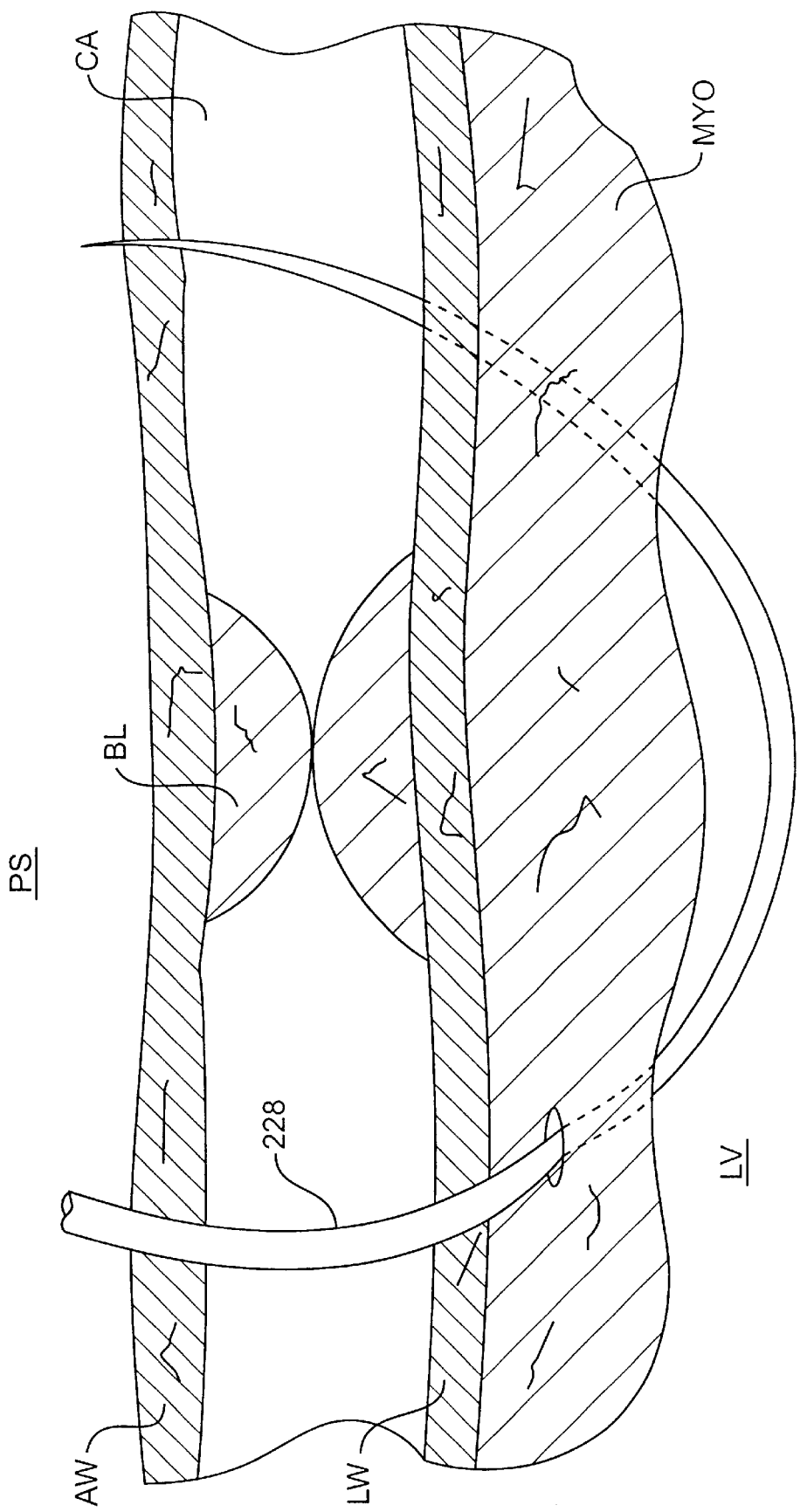
Figure 11C:
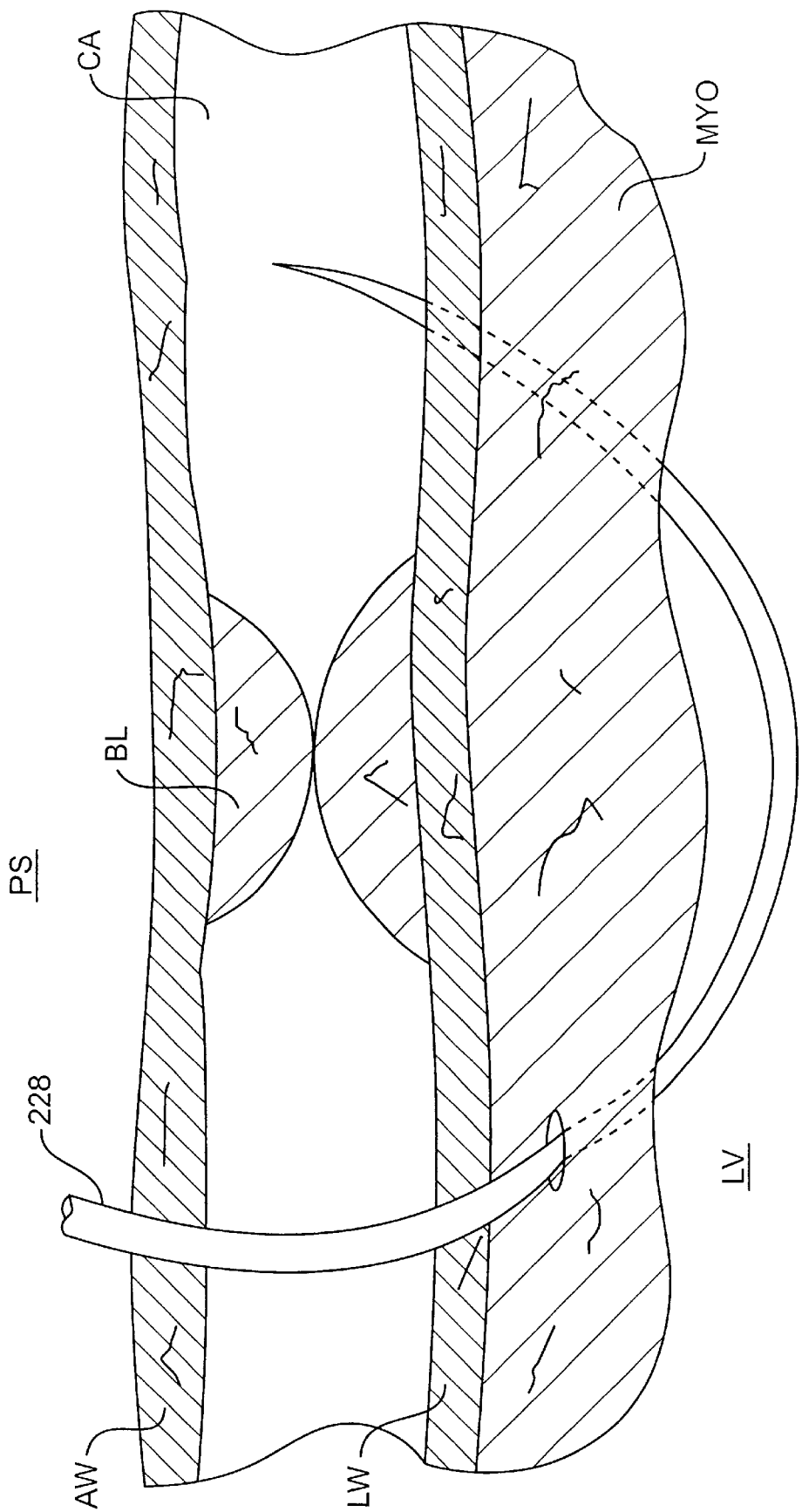

FIGS. 11A–11F illustrate a method and apparatus for delivering a shunt directly from the left ventricle to the coronary artery. As shown in FIG. 11A, a needle 228 is inserted into the myocardium MYO, preferably adjacent to the coronary artery CA, at a position generally proximal to a blockage BL in the coronary artery CA. As shown in FIG. 11B, the needle 228 is preferably curved in a manner that as it is advanced through the myocardium MYO, it enters the left ventricle LV, and then reenters the myocardium MYO toward the coronary artery CA. In one embodiment, shown in FIG. 11B, needle 228 enters the coronary artery CA and punctures the anterior wall into pericardial space PS. In another embodiment, shown in FIG. 11C, needle 228 only advances until it is within coronary artery CA.

Figure 11E:
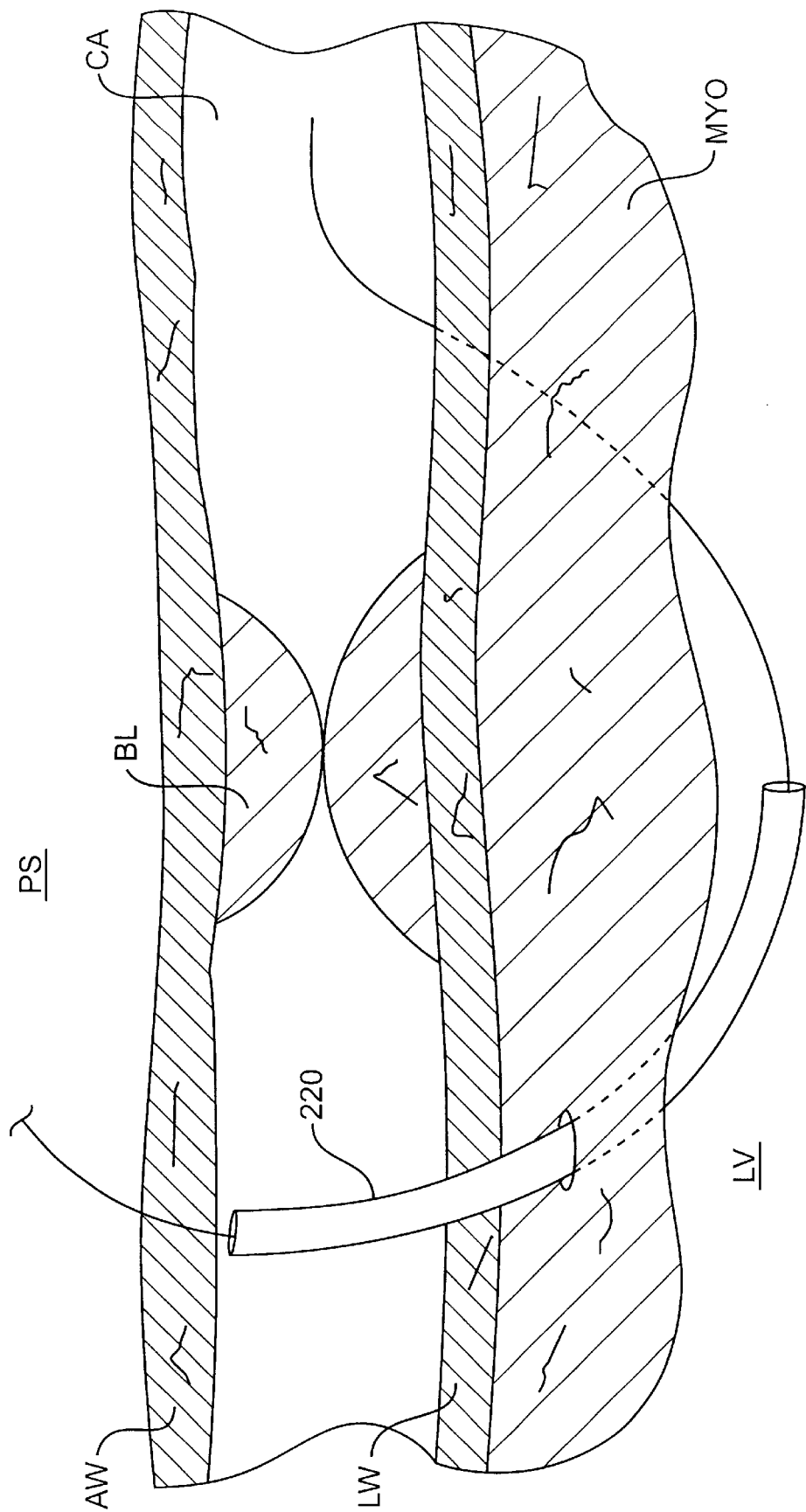

Needle 228 is preferably hollow to allow a guidewire 208 to pass therethrough. This guidewire 208 is shown in FIG. 11D after the needle 228 has been removed. It will be appreciated that although FIG. 11D illustrates the embodiment wherein the needle 228 does not puncture through anterior wall AW, the guidewire 208 may also be provided through the anterior wall into pericardial space PS through the needle of FIG. 11C. As shown in FIG. 11E, a shunt 220 is delivered over the guidewire, preferably using a pushing rod, delivery catheter, or other method known to one of skill in the art, such that its proximal end 222 opens into the left ventricle LV and its distal end 224 opens into the coronary artery CA, as shown in FIG. 11F. Once the guidewire 208 is removed, the shunt 220 provides a left ventricular conduit to the coronary artery CA. This shunt is preferably angled to provide downstream flow of blood from out of the conduit into the coronary artery CA.

Figure 12:
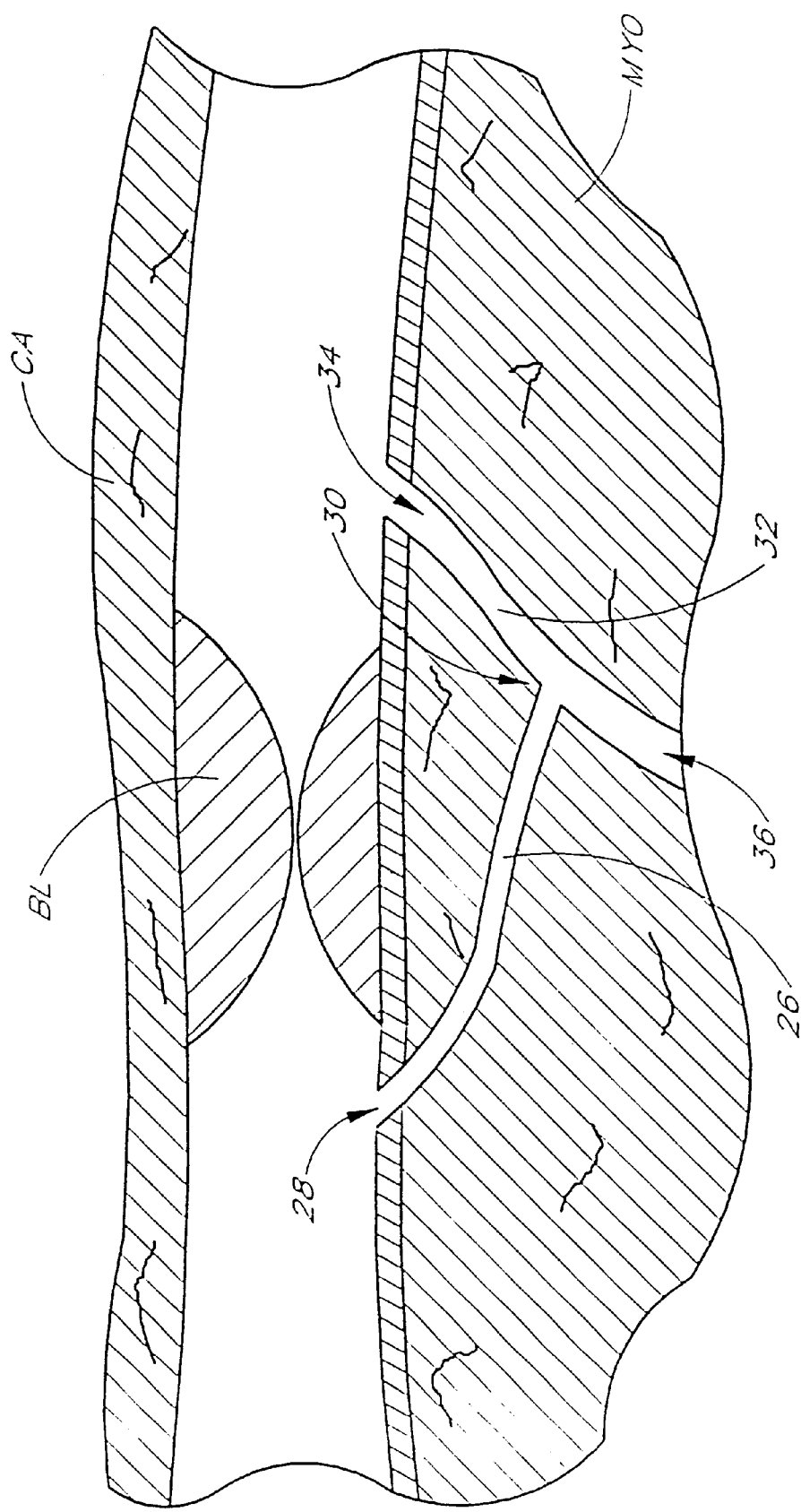
FIG. 12 is a schematic, partial cross-sectional view of a coronary artery adjacent the left ventricle, showing a Y-shaped tunnel formed through the myocardium to bypass a blockage in the coronary artery.

In another embodiment, a tunnel is created through the myocardium MYO from a point proximal to a blockage in the coronary artery into the left ventricle. As shown in FIG. 12, where a blockage BL substantially occludes a coronary artery CA, a first tunnel 26 is formed proximally of the blockage BL extending into the myocardium MYO beneath the blockage BL. The tunnel 26 has a proximal end 28 which opens into the coronary artery CA proximal to the blockage BL, and a distal end 30 within the myocardium MYO beneath the blockage BL. A second tunnel 32 extends from the distal end 30 of the first tunnel, with a first branch 34 opening a channel to the coronary artery CA past the location of the blockage BL. A second branch 36 of the second tunnel 32 extends downward from the distal end 30 and opens into the left ventricle LV. As illustrated in FIG. 12, a substantially Y-shaped passageway is thereby created through the myocardium MYO to bypass the blockage BL.

Figure 13:
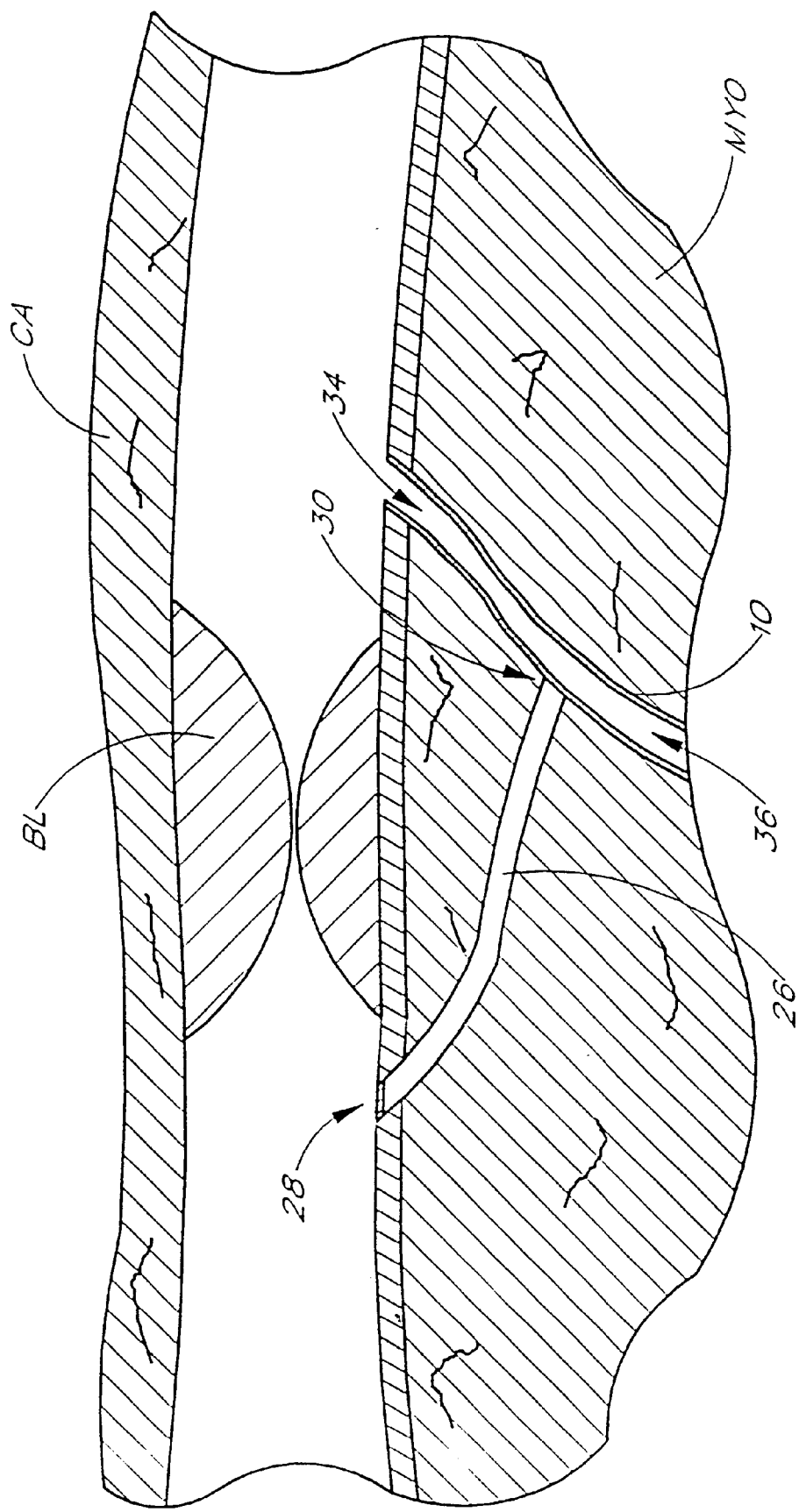
FIG. 13 is a partial cross-sectional view of the Y-shaped tunnel of FIG. 12, showing a stent provided therein.

As shown in FIG. 13, after formation of the Y-shaped passageway in the myocardium MYO, one or more stents 10 are provided in the second tunnel 32 extending between the left ventricle LV and the coronary artery CA. This stent 10 opens the myocardial passageway which provides the bypass past blockage BL. Positioning of stent 10 in the tunnel 32 is preferably accomplished by advancing a guidewire through the first tunnel 26 and into each branch 34 and 36 of the second tunnel 32, and then advancing the stent over the guidewire in the manner described below. After placement of the stent, the tunnel 26 between the coronary artery CA and stent 14 is preferably closed at least at distal end 30, and more preferably, also at proximal end 28. Closure of the tunnel may be accomplished by inserting plugs or other blocking means 38, or by sealing the tunnel with sutures or similar methods. Other suitable closure means include occlusion coils and balloons, adhesives such as cyanoacrylate, and plugs such as sold under the trade name GELFOAM. Alteratively, the tunnel may be closed due to the natural contraction of the openings 28 and 30 over time.

It will be appreciated that while the above embodiments describe forming a channels, either through the myocardium or through the pericardial space, the channel may also be formed by other pathways exiting the blood vessel proximal to a blockage and reentering the vessel distal to the blockage. With respect to the above described embodiments, it will be appreciated that prior to delivering the stent over the guidewire, the passageway may be dilated using the methods described below. Furthermore, the guidewire 208 may be anchored to the myocardium as described below.

II. The Delivery Catheter

Once access to the desired insertion site is achieved, an appropriate delivery system is brought to the site. The preferred embodiments described hereinbelow are directed to a delivery system for inserting stents and other medical devices into the myocardium at an angle relative to the axis of blood flow. It should be appreciated that the angle of insertion may be adjusted between 0 and 180 degrees depending on the desired application. Furthermore, while the delivery systems below describe insertion of devices into the myocardium, these systems also enable angled delivery of medical devices into and through other body lumens and tissues.

A. Dual Balloon Delivery System

Figure 14:
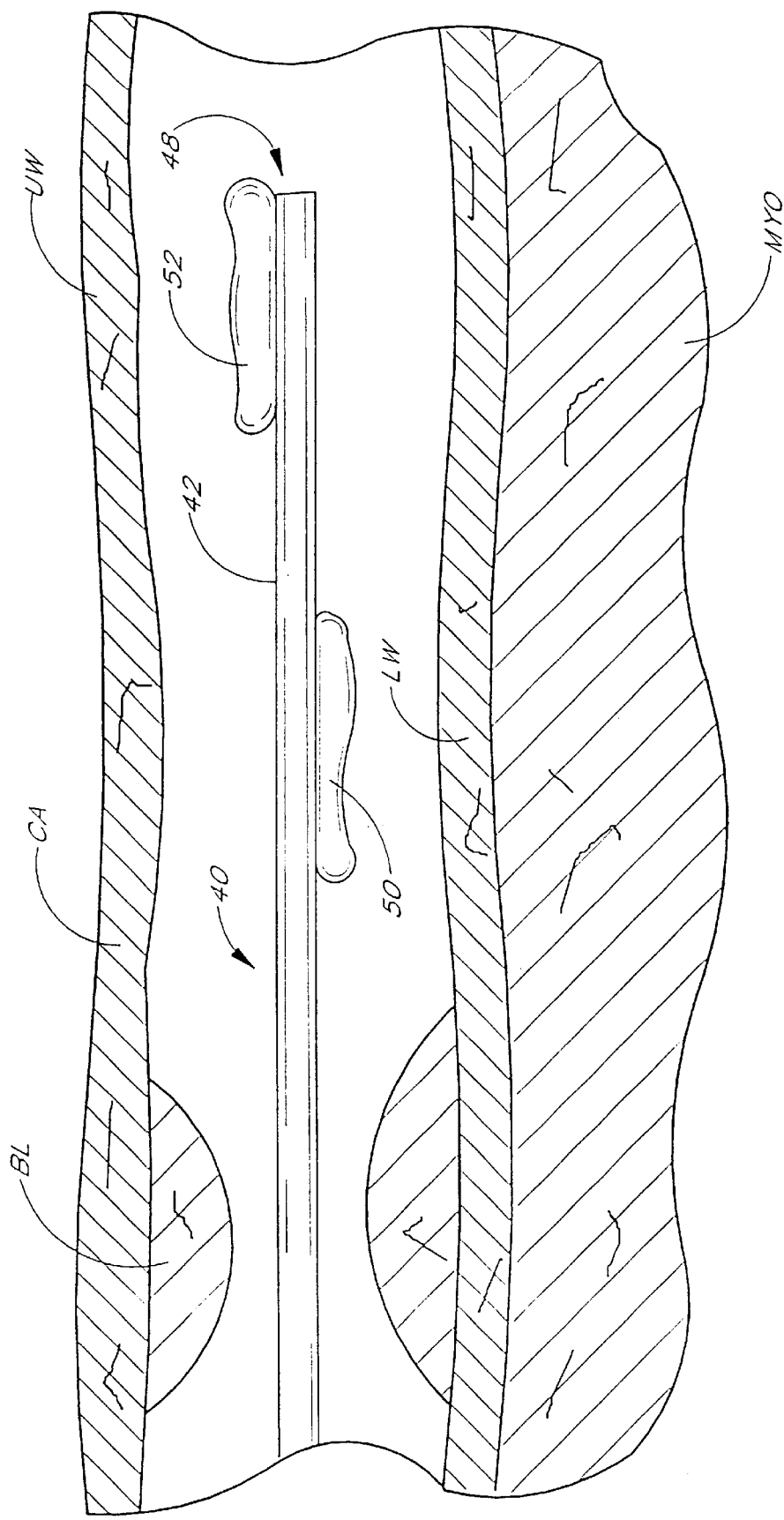
FIG. 14 is a side view of a delivery catheter carrying two uninflated steering balloons in a blocked coronary artery, with the artery shown partially cut away.

In one embodiment, the stent delivery system comprises a catheter which creates an angled bend for insertion of devices into the myocardium MYO. FIG. 14 illustrates a delivery catheter 40 which has been advanced into the coronary artery CA past the blockage BL. Catheter 40 is an elongate tubular body 42 having a lumen 44 (not shown) extending from a proximal end 46 (not shown) to a distal end 48. The catheter 40 is preferably formed from a flexible biocompatible material such as polymers, stainless steel or nitinol.

Mounted adjacent distal end 48 of catheter 40 are two steering guides, which are preferably expandable members such as inflatable balloons 50 and 52. As illustrated in FIG. 14, a steering member, such as balloon 52, is preferably located distally of an anchoring member, such as balloon 50, such that steering balloon 52 is disposed near or at the very distal tip 48 of the catheter 40. Balloons 50 and 52 are each preferably mounted on opposite sides of the catheter tubular body 42, such that anchoring balloon 50 is mounted facing lower wall LW adjacent the myocardium MYO, and steering balloon 52 is mounted facing upper wall UW opposite lower wall LW. Alternatively, the anchoring balloon 50 may be mounted concentrically around the tubular body 42 so that inflation of the balloon expands against both the upper and lower walls. It will be appreciated that other devices, such as filters, posts and other expandable members may be used for the anchoring and/or steering members.

Figure 15:
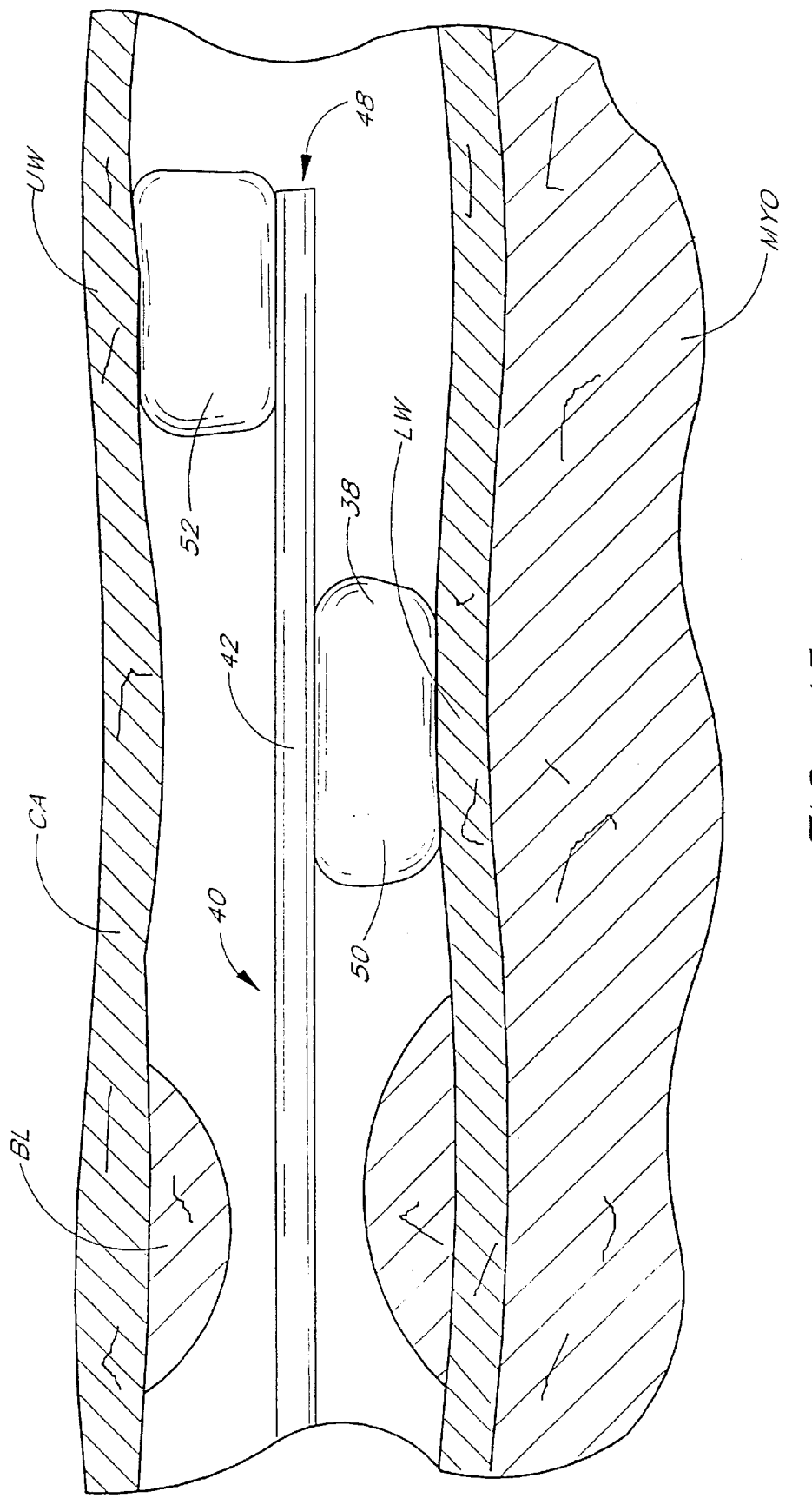
FIG. 15 is a side view of the delivery catheter of FIG. 14, showing the two balloons partially inflated.

As shown in FIG. 14, as the catheter 40 is advanced into position adjacent the myocardium MYO, the balloons 50 and 52 remain uninflated. As illustrated in FIG. 15, once the distal tip 48 of the catheter 40 is positioned adjacent the desired insertion site into the myocardium MYO, the balloons 50 and 52 are inflated. Inflation causes the balloons 50 and 52 to cooperate with the walls of the blood vessel to turn the distal end of the catheter. More particularly, in an intermediate state, anchoring balloon 50 inflates against the lower wall LW of the coronary artery CA, while steering balloon 40 presses against the upper wall UW.

Figure 16:
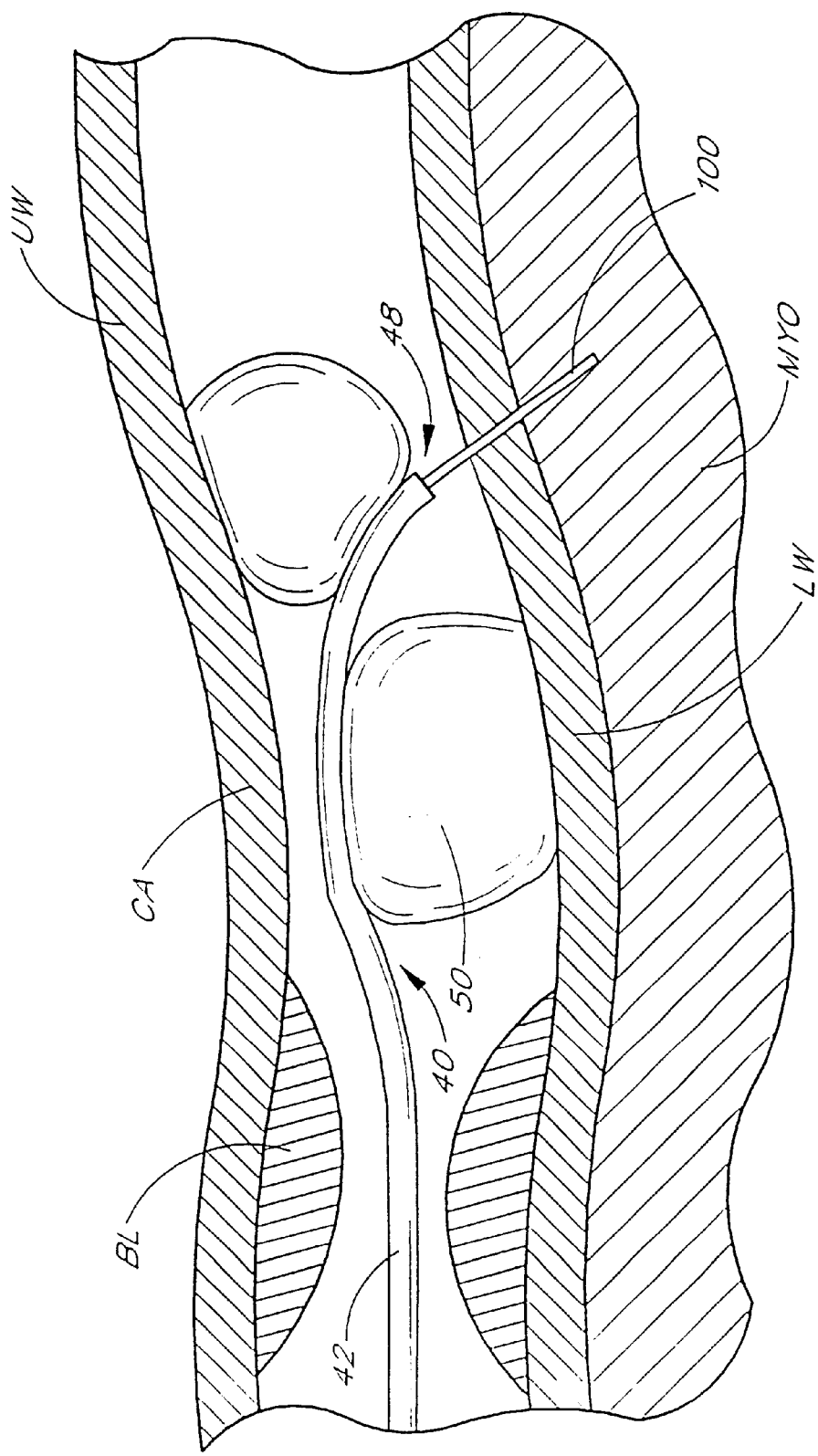
FIG. 16 is a side view of the delivery catheter of FIG. 14, showing the two balloons fully inflated and a guidewire extending from the distal end of the delivery catheter.

As illustrated in FIG. 16, anchoring balloon 50 acts to secure the tubular body 42 within the coronary artery CA. Inflation of balloon 50 also preferably causes the catheter 40 to displace in a direction opposite lower wall LW, thereby placing the catheter into a better position for transverse insertion of the distal end 48 into the myocardium MYO. Steering balloon 52 is further inflated, causing the distal tip 48 of the tubular body 32 to turn downward towards lower wall LW and myocardium MYO due to the resistance provided by upper wall UW against the balloon. FIG. 16 also illustrates the effect that the dual balloon inflation may have on the upper and lower walls of the coronary artery CA. When balloons 50 and 52 are fully inflated, forces created on the lower wall LW and upper wall UW, respectively, may cause the walls to shift at least slightly in the direction of balloon inflation. In particular, the lower wall LW may have a tendency to bend upwards distally of the balloon 50 toward the distal end 48 of delivery catheter 40 to assist in angling of the catheter.

Due to the turning action of catheter 40 caused by inflation of balloons 50 and 52, as well as the bending of lower wall LW toward distal end 48, once inflation of the balloons 50 and 52 is complete, the distal tip 48 of catheter 30 is positioned at a substantially transverse angle to the lower wall LW of the coronary artery CA and the myocardium MYO. From this position, the catheter 40 may serve as a guide for the delivery of devices used in creating a myocardial passageway. For example, as shown in FIG. 16 and described in further detail below, a puncture wire or guidewire 100 is advanced through the lumen 44 of tubular body 42, and then ejected out the distal tip 48 of the catheter 40 to puncture the lower wall LW into the myocardium MYO.

Figure 17:
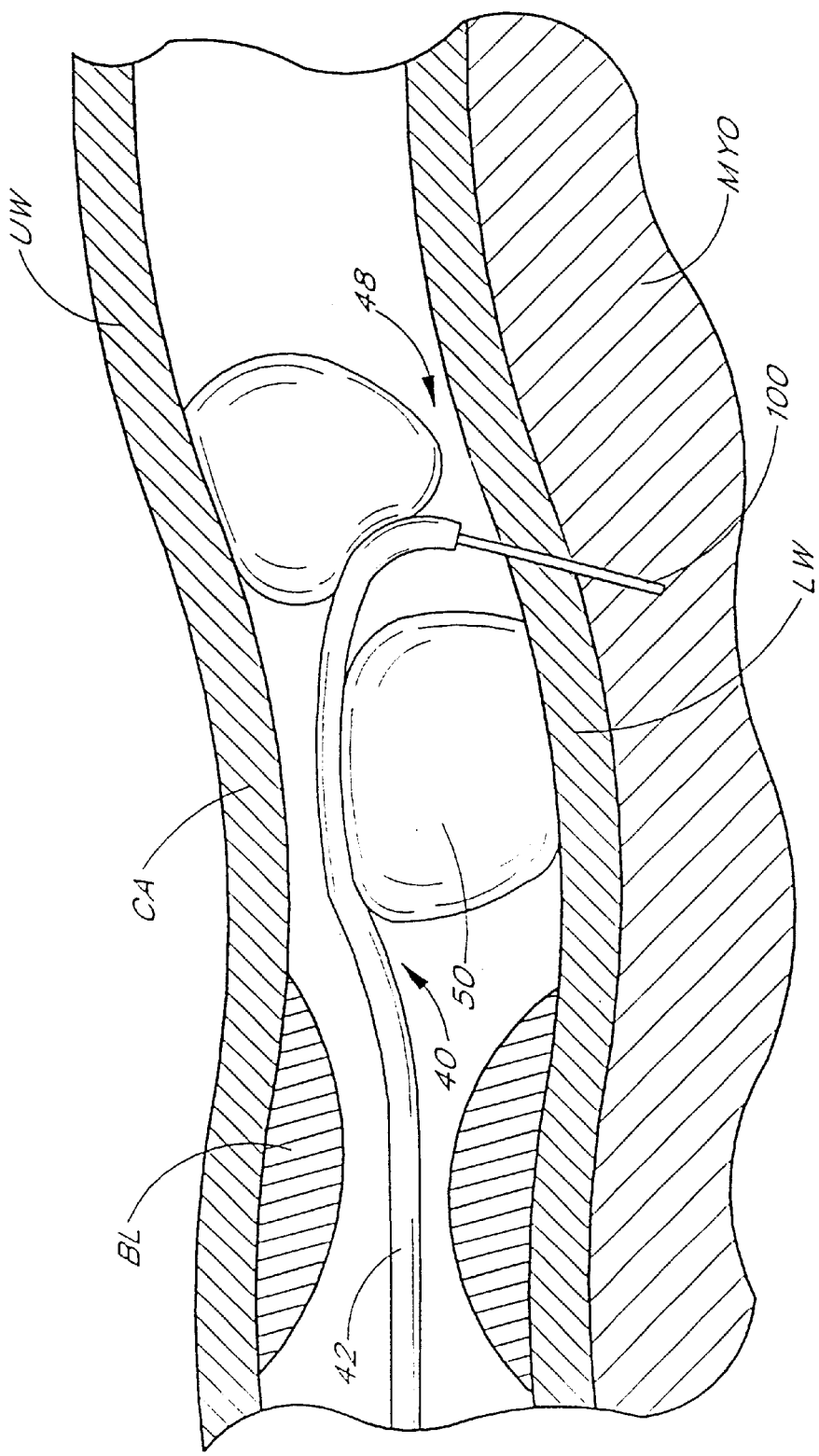
FIG. 17 is a side view of the delivery catheter of FIG. 14, showing the two balloons fully inflated and a guidewire extending from the distal end of the delivery catheter at a back angle.

The dual balloon delivery system described above is also advantageous in that it allows turning of the catheter 40 at angles greater than 90 degrees relative to the direction of blood flow through the coronary artery CA. Thus, as shown in FIG. 17, the balloons 50 and 52 may be inflated to angle the distal end 48 of the catheter 40 at a back angle toward the myocardium.

B. Pull Wire Actuator

Figure 18:
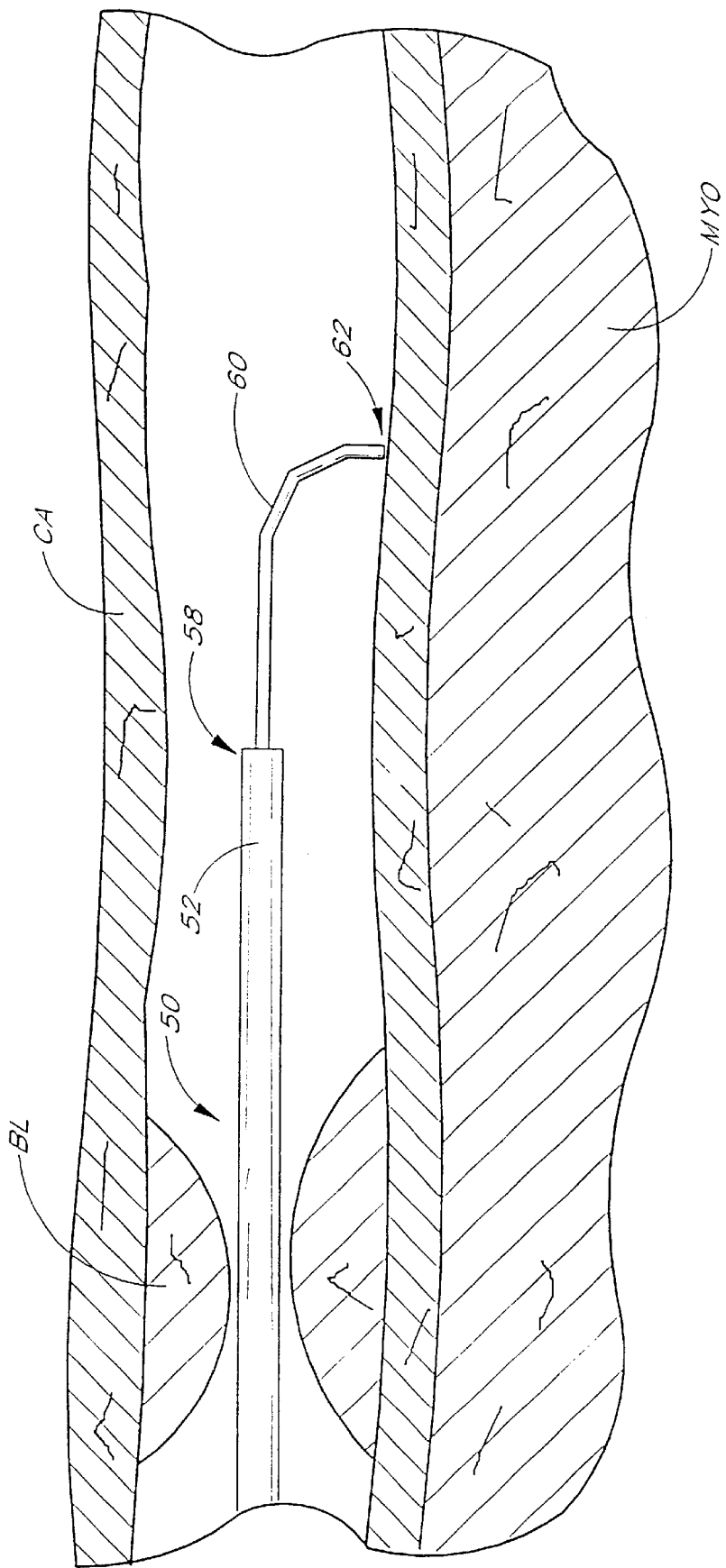
FIG. 18 is a side view of a delivery catheter with a tip deflecting wire in a blocked coronary artery, with the artery shown partially cut away.

FIG. 18 illustrates another embodiment for delivering devices transversely into the myocardium MYO of a patient's heart. A catheter 54 is shown extending through the coronary artery CA past a blockage BL. Catheter 54 comprises an elongate tubular body 56 with a lumen 58 (not shown) extending therethrough from a proximal end 60 (not shown) to a distal end 62. A tip-deflecting puncture wire or pull wire 64 extends from the distal end 62 of the catheter 54. The wire 64 is actuated at the proximal end (not shown) so that it deflects to form a near 90 degree angle relative to the catheter 54. It will be appreciated that the wire 64 may also be actuated to form angles of less than or greater than 90 degrees. The distal tip 66 of wire 64 is turned so that it is provided adjacent the myocardium MYO. This shape can be locked and the wire 64 is pushed forward through the coronary artery CA and into the wall of the myocardium MYO. As described in further detail below, with the wire 64 in place medical devices are delivered over the wire into the myocardium.

C. Side Port

Figure 19A:
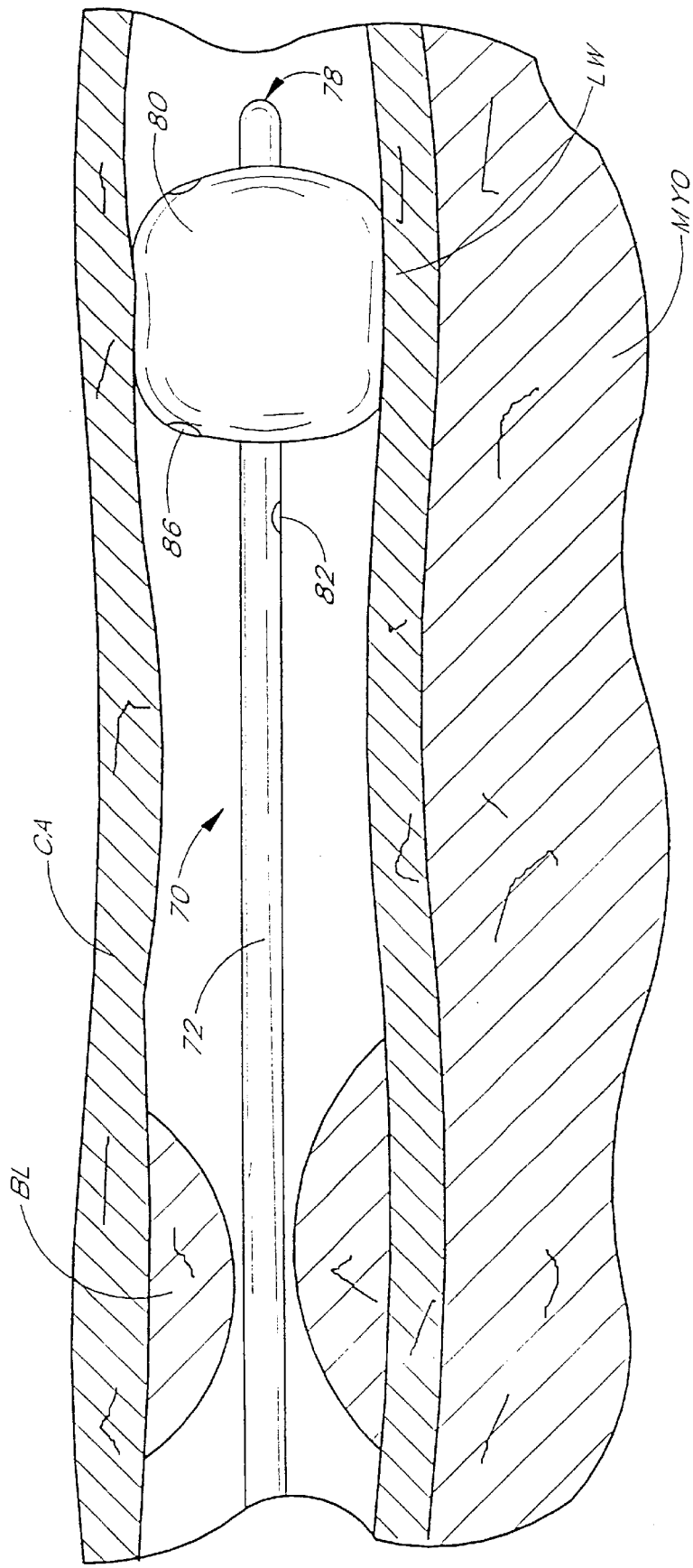
FIG. 19A is a side view of a delivery catheter having a side port proximal to an inflatable balloon in a blocked coronary artery, with the artery shown partially cut away.
Figure 20A:
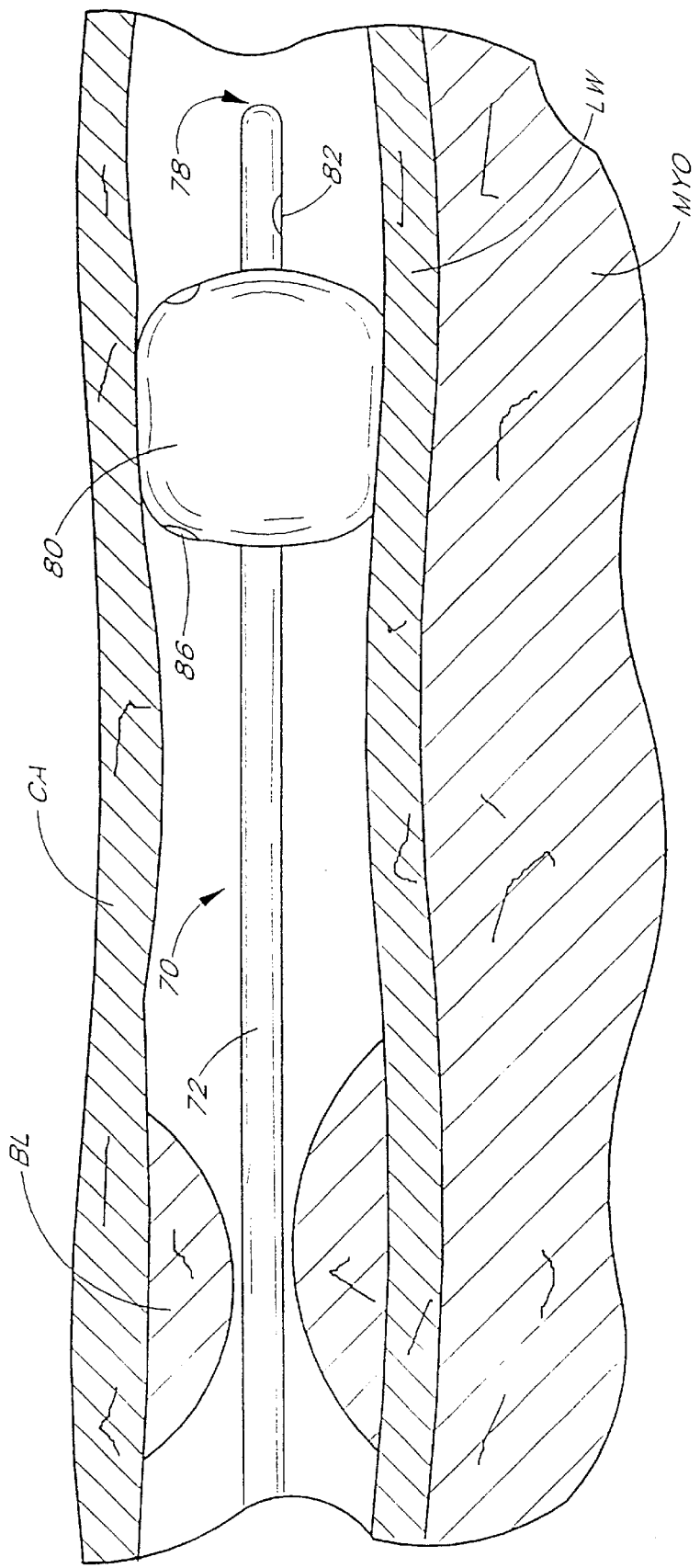
FIG. 20A is a side view of a delivery catheter having a side port distal to an inflatable balloon in a blocked coronary artery, with the artery shown partially cut away.

In another embodiment, a delivery catheter is provided with a side port which allows a puncture wire to exit therethrough. As shown in FIGS. 19A and 20A, delivery catheter 70 comprises an elongate tubular body 72 having a proximal end 76 (not shown) and a distal end 78 and a lumen 74 (not shown) extending at least partially therethrough. Preferably, mounted on distal end 78 is an expandable or anchoring member such as inflatable balloon 80, which is inflated to maintain the position of the catheter 70 within the artery. The balloon 80 is preferably a perfusion type balloon having a channel 86 to allow blood flow through the artery during the procedure. Alternatively, filters or other devices which allow blood flow through the artery while anchoring the catheter 70 may also be utilized. Perfusion may also be provided through a lumen in the tubular body 72. A distal opening or side port exit 82 is provided rough the wall of tubular body 72 near the distal end of the catheter extending from lumen 74. The side port 82 may be located either proximal to the balloon 80, as in FIG. 19A, or distal to the balloon 80, as in FIG. 20A. Catheter 70 is delivered through the vasculature until the side port exit 82 is past the location of the blockage BL. Prior to balloon inflation, the catheter 70 is turned about its longitudinal axis so that the opening 82 faces the myocardium.

Figure 19B:
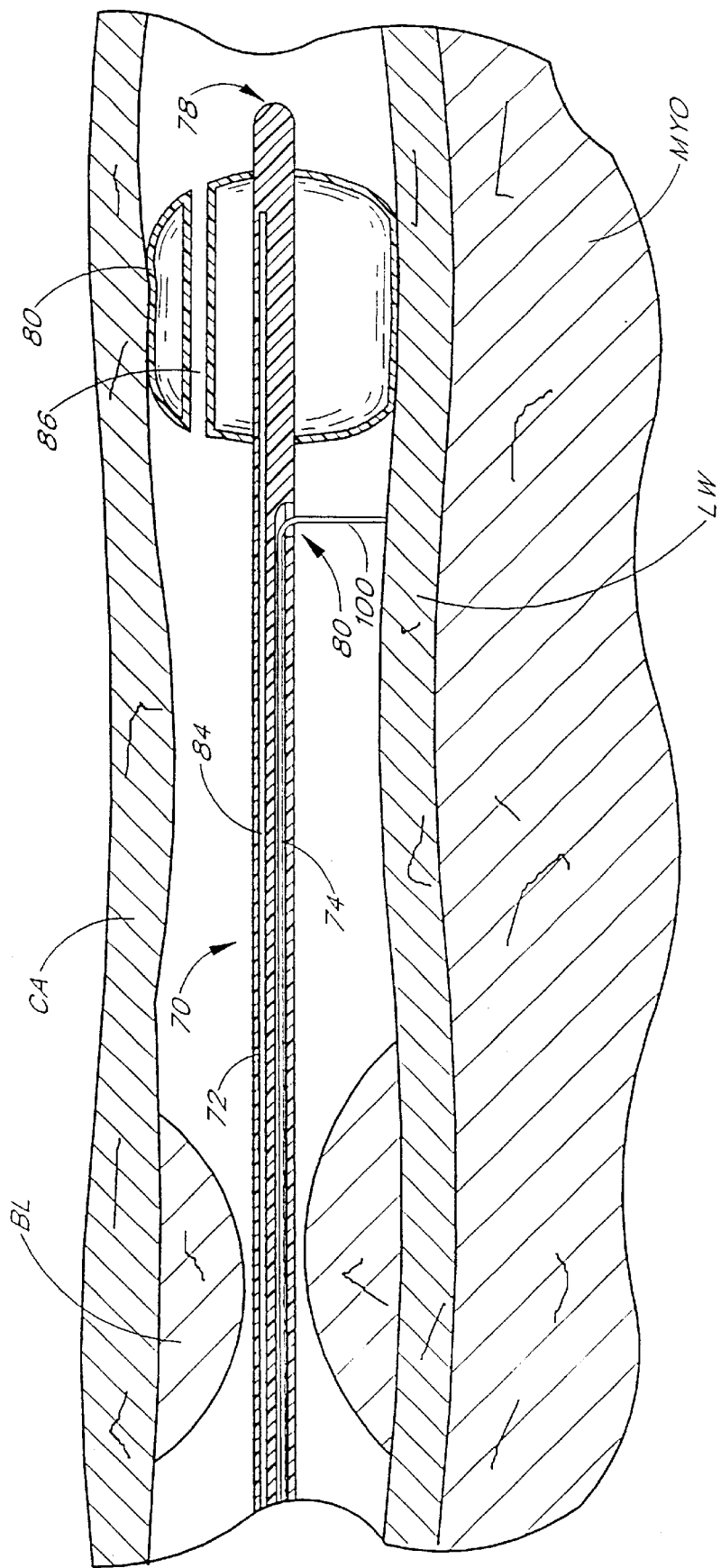
FIG. 19B is a cross-sectional view of the delivery catheter of FIG. 19A, further showing a guidewire extending therethrough.
Figure 20B:
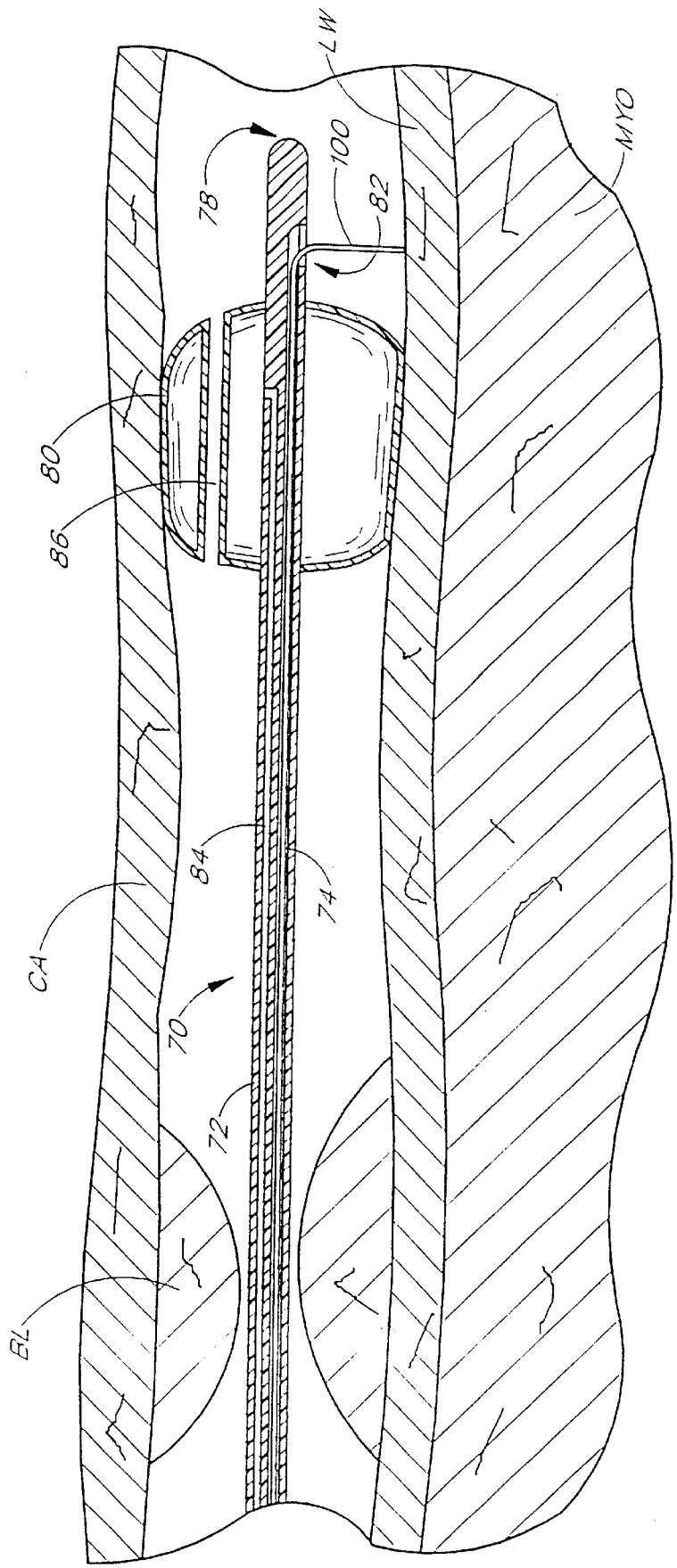
FIG. 20B is a cross-sectional view of the delivery catheter of FIG. 20A, further showing a guidewire extending therethrough.

FIGS. 19B and 20B illustrate the pathway for a guidewire 100 to pass through the lumen 74 of catheter 70. In FIG. 19B, guidewire 100 extends through the lumen 74 toward the distal end 78 of the catheter. Proximal to balloon 80, the lumen 74 turns downward toward side port exit 82. Thus, before guidewire 100 reaches the proximal end of balloon 80, the guidewire 100 is directed out of the side port 82 toward the lower wall LW of the coronary artery CA. A second lumen 84 is also provided within catheter 70 to direct inflation fluid to balloon 80.

FIG. 20B shows substantially the same configuration except that the lumen 74 extends through the balloon 80 such that the side port exit 82 is located distal to the balloon 80. Guidewire 100 therefore extends through lumen 74 and out side port exit 82 toward the lower wall LW. As with FIG. 19B, a second lumen 84 is provided through tubular body 72 to direct inflation fluid into the balloon 80.

Figure 21A:
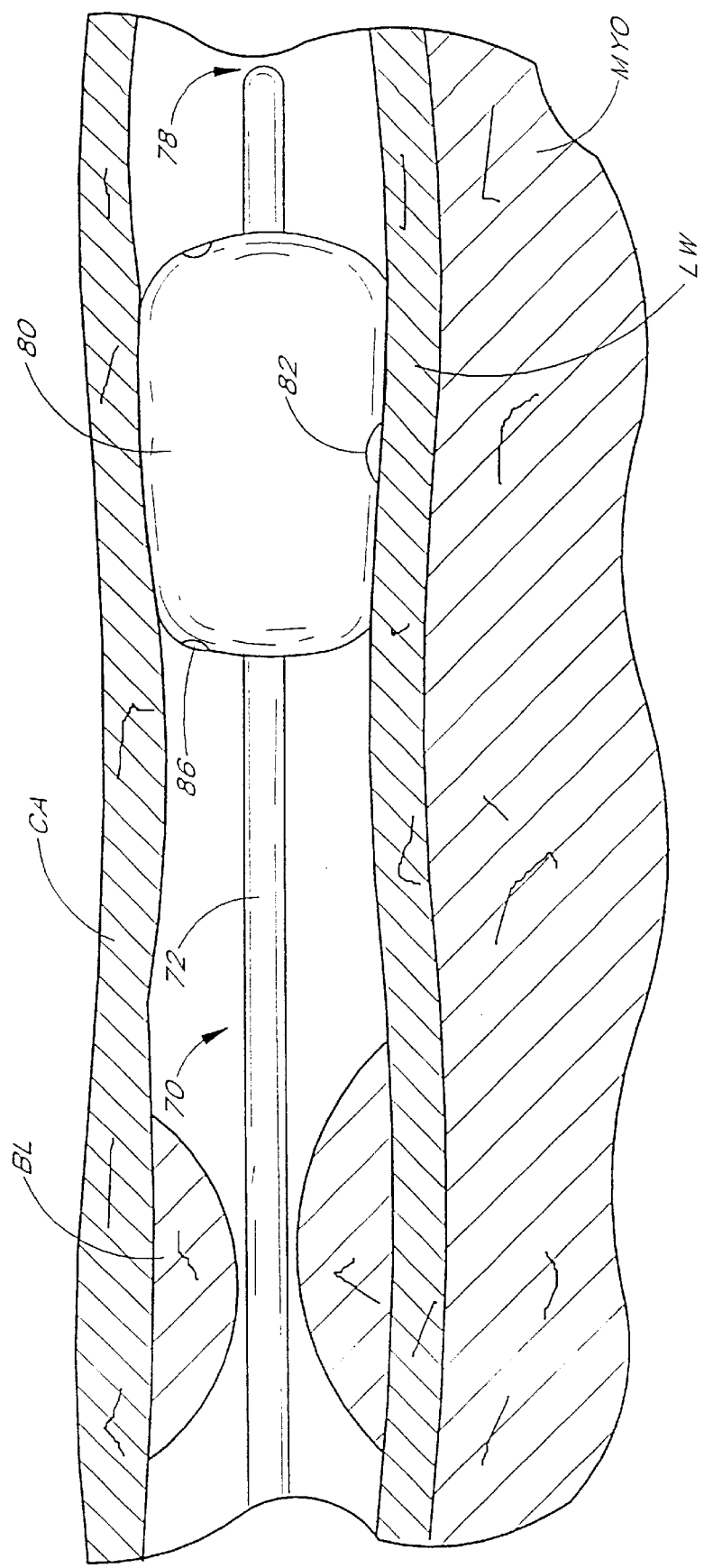
FIG. 21A is a side view of a delivery catheter having a side port within an inflatable balloon in a blocked coronary artery, with the artery shown partially cut away.
Figure 21B:
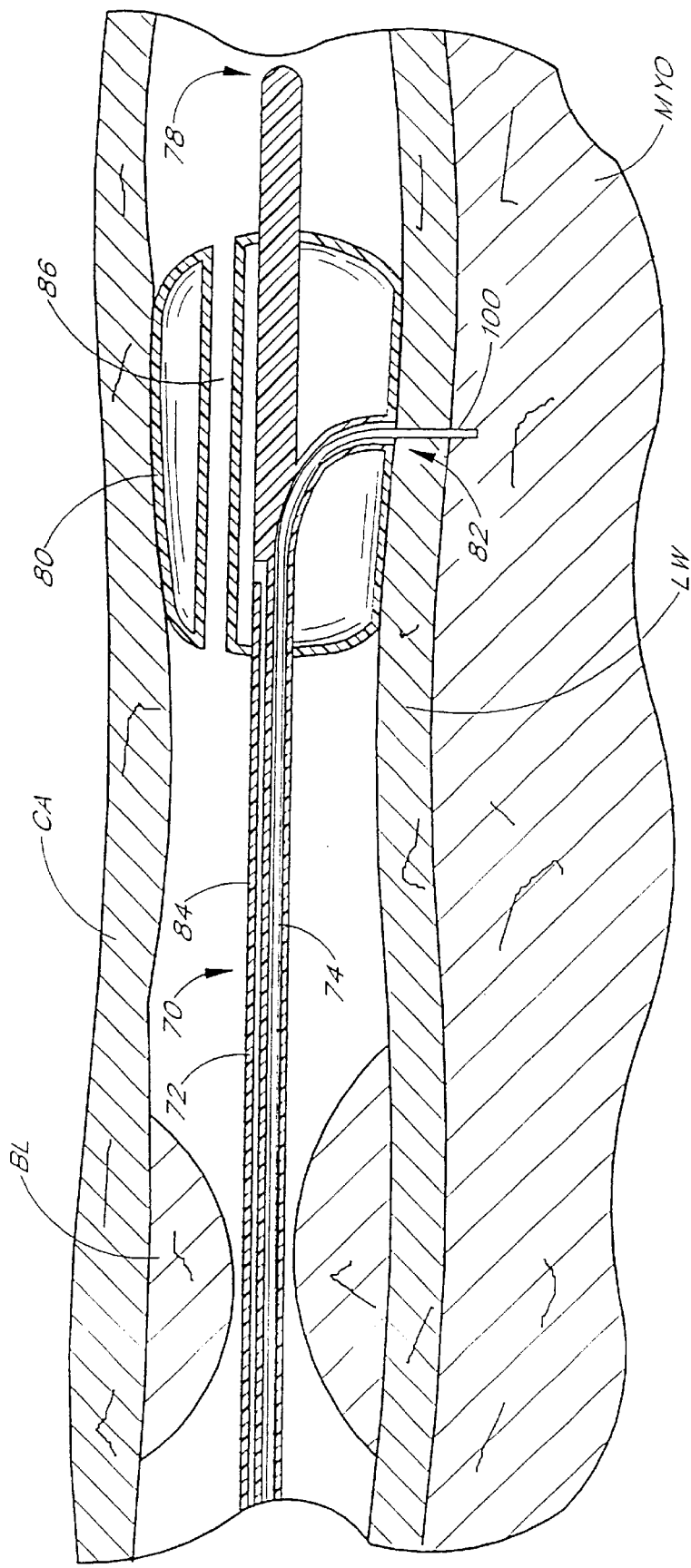
FIG. 21B is a cross-sectional view of the delivery catheter of FIG. 21A, further showing a guidewire extending through the balloon.

In another embodiment, as shown in FIG. 21A, the side port 82 is located on an exterior surface of the balloon 80. After the catheter 70 is delivered to a location past the blockage BL, balloon 80 is inflated. As shown in the cross-sectional view of FIG. 21B, balloon 80 preferably comprises a perfusion channel 86 extending from the proximal end to the distal end of the balloon 80 to allow blood to flow through the vessel. A lumen 74 is provided through the catheter 70 which extends into balloon 80 and turns downward into side port exit 82. The catheter 70 also has a lumen 84 for inflation of balloon 80.

Guidewire 100 is advanced through lumen 74 and out side port exit 82 into the myocardium MYO.

Figure 21C:
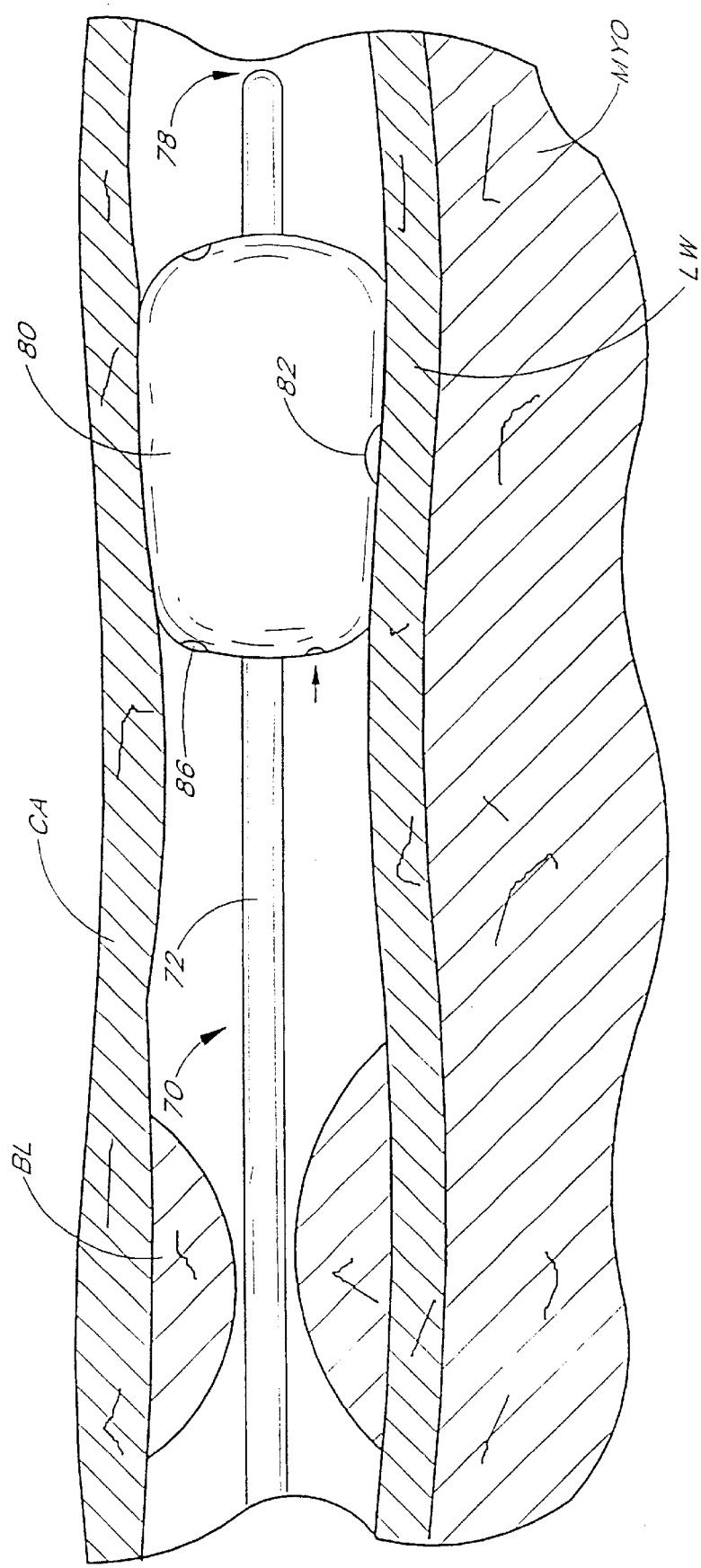
FIG. 21C is a side view of an alternative embodiment of a delivery catheter having a side port within an inflatable balloon in a blocked coronary artery, with the artery shown partially cut away.
Figure 21D:
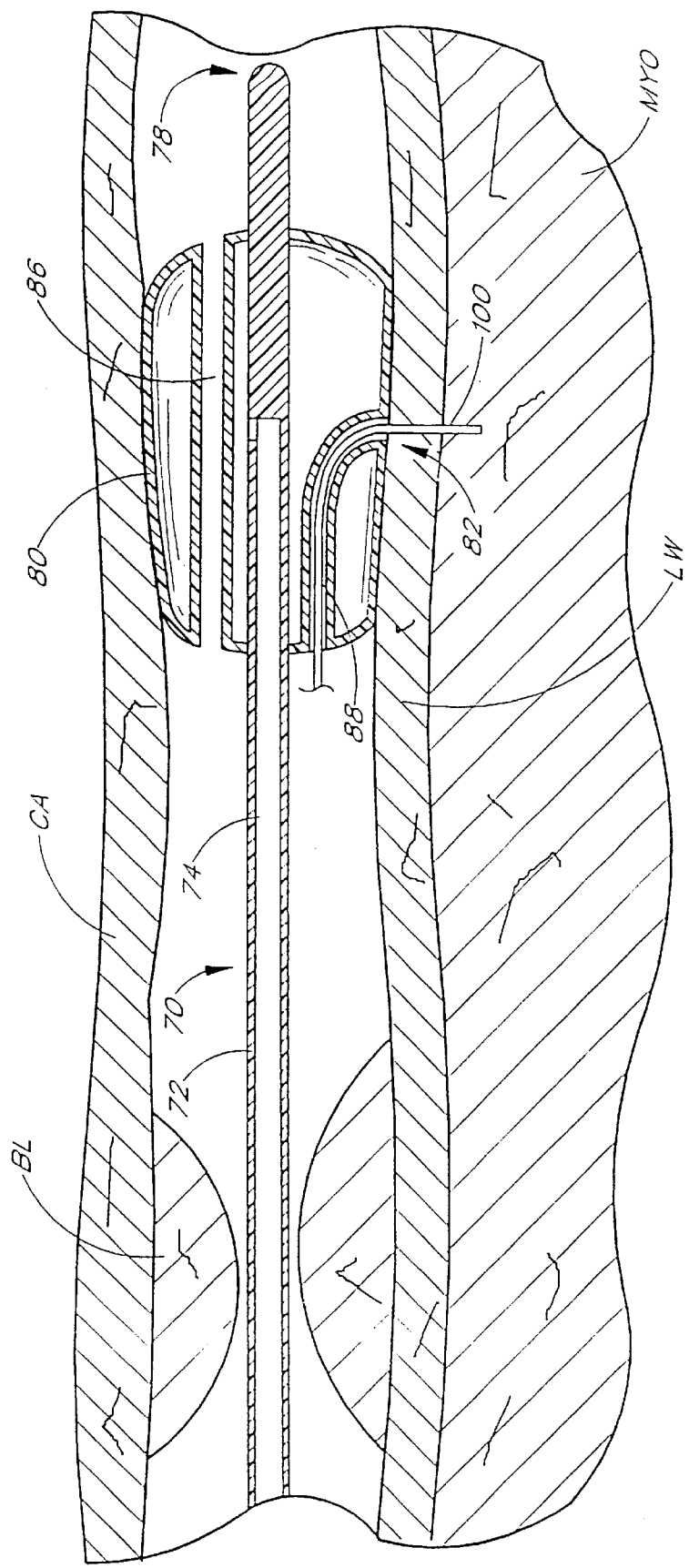
FIG. 21D is a cross-sectional view of the delivery catheter of FIG. 21C, further showing a guidewire extending through the balloon.

FIGS. 21C and 21D illustrate yet another embodiment of a delivery catheter with a side port exit. The catheter 70 comprises an elongate tubular body 72 having a lumen 74 extending from a proximal end 76 (not shown) to distal end 78. This lumen 74 is in fluid communication with balloon 80 to provide inflation of the balloon. When inflated, balloon 80 has a perfusion lumen 86 which allows blood to perfuse therethrough. The balloon 80 also has a guide lumen 88 extending therethrough which, when inflated, extends from a proximal end of the balloon to the lower wall LW. A guidewire 100 may then be inserted through the guide lumen 88 and out side port exit 82 into the myocardium MYO.

Although the side port exit 82 as illustrated in FIGS. 19A–21D is shown to cause the guidewire 100 to exit at an approximately 90 degree angle, it will be appreciated that the side port exit 82 can cause the guidewire 100 to exit at angles less than or greater than 90 degrees as well. This may be accomplished by creating a turn within the lumen 74 near the exit 82 to direct the guidewire in the desired direction. A lumen 74 creating this desired angle is shown in FIG. 20C. More particularly, because of the path formed by the lumen 74 at the side port exit 82, guidewire 100 may exit at an obtuse angle relative to the insertion direction of the catheter 70. It will be appreciated that the lumens 74 in FIGS. 19B and 21B and the lumen 88 in FIG. 21D may be turned to vary the angle the guidewire 100 exits the side port 82 anywhere from about 0 to 180 degrees.

Figure 22A:
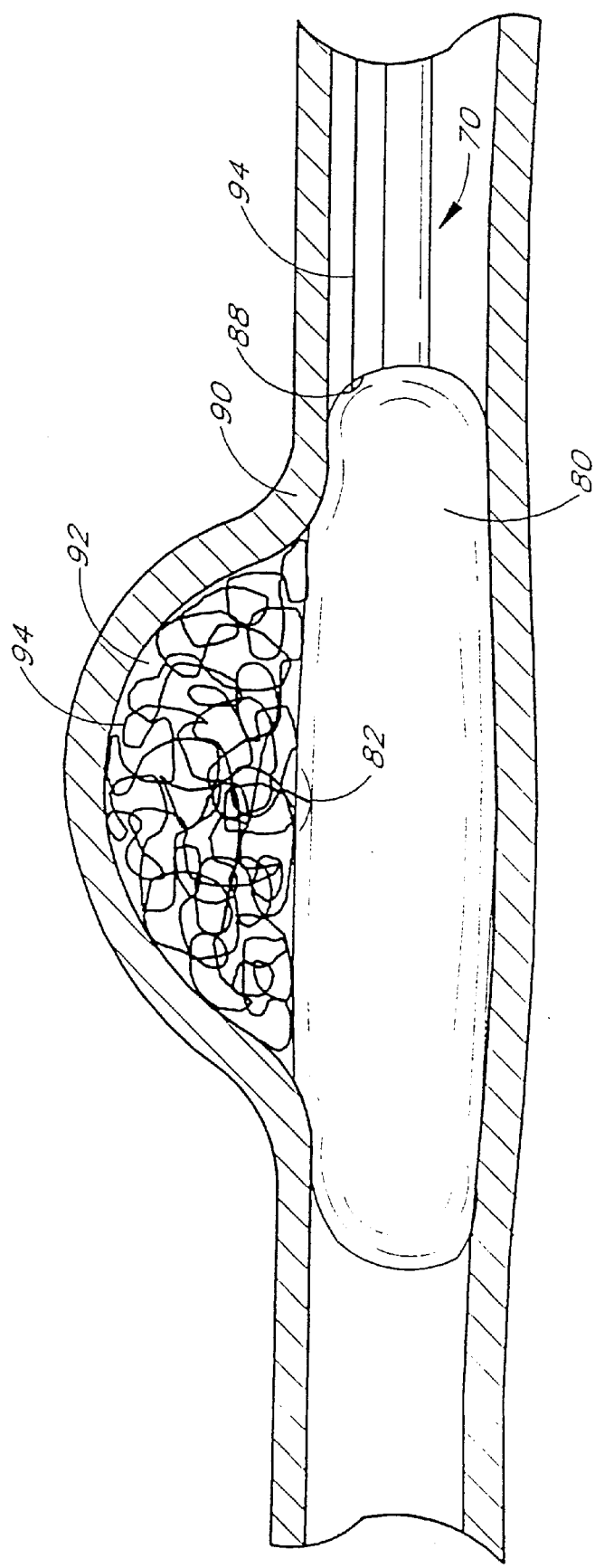
FIG. 22A is a side view of a delivery catheter having a side port within an inflatable balloon used for treating an aneurysm in a blood vessel, with the vessel shown partially cut away.

The delivery catheters described and shown in FIG. 21A–21D are useful not only for disposing a stent into the myocardium but also for the treatment of aneurysms. Aneurysms are typically treated by introducing embolic elements to fill the aneurysm. When the aneurysm opens substantially into the blood vessel, it becomes difficult to retain the embolic elements within the aneurysm while the aneurysm is being filled. FIG. 22A illustrates a method for solving this problem using the delivery catheter 70 described above with respect to FIGS. 21C and 21D. In a blood vessel 90 with an aneurysm 92, a catheter 70 carrying inflatable balloon 80 is advanced such that the balloon 80 is adjacent the aneurysm 92. The balloon 80 is inflated to substantially enclose the aneurysm 92. A wire 94 or other embolic element is advanced through the guide lumen 88 of balloon 80 and out side port 82. The wire 94 fills up the aneurysm 92, and is maintained in the aneurysm due to the fact that the balloon 80 encloses the aneurysm to prevent wire 94 from extending into the vessel. It should be appreciated that the wire 94 or other embolic element may also be delivered through a lumen 74, as shown with respect to the embodiment in FIG. 21B. After the aneurysm 92 is filled with wire 94, the wire 94 is cut, the balloon 80 is deflated, and the catheter 70 is removed from the vessel.

Figure 22B:
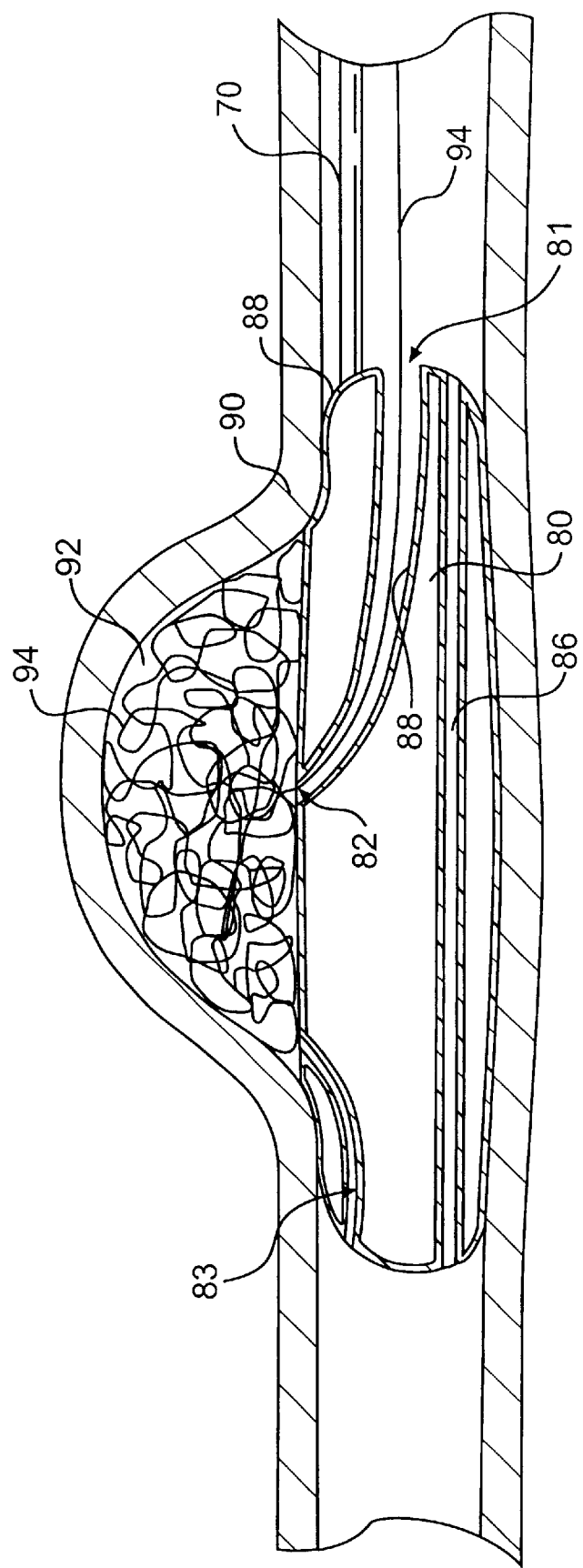
FIG. 22B is a partial cross-sectional view of a delivery catheter having a side port within an inflatable balloon used for treating an aneurysm in a blood vessel, with the vessel shown partially cut away.

FIG. 22B illustrates another embodiment of the balloon 80 as described above for treating an aneurysm 92. The balloon 80 is mounted on catheter 70 which has an inflation lumen (not shown) extending therethrough for inflating the balloon. Perfusion lumen 86 extends through the balloon 80 as shown when the balloon is inflated, to allow blood to flow from proximal of the balloon to distal of the balloon. Guide lumen 88 extends from the proximal end of the balloon to the side of the balloon facing the aneurysm, terminating in an exit port 82. The guide lumen 88 is preferably funnel-shaped or tapered, having an opening 81 at the proximal end of the balloon that is larger than the opening of the side port exit 82. This enables wire 94 to more easily be directed through the balloon 80 into the aneurysm 92. Because blood may also flow into the guide lumen 88 into the aneurysm, an outflow lumen 83 is provided in the balloon 80, creating fluid communication between the aneurysm and the distal end of the balloon to allow blood to flow out of the aneurysm 92.

It will be appreciated that insertion of the embolic element need not be through the balloon 80. For instance, a separate catheter may be used to deliver wire or other embolic elements into the aneurysm, while a balloon 80 such as described above encloses the aneurysm. In one embodiment, a catheter delivering a wire may be inserted into the aneurysm prior to inflating a balloon 80 such as described above. The balloon is then inflated, and the aneurysm is filled with wire exiting from the catheter. It will also be appreciated that devices other than balloons may be used to enclose the aneurysm while embolic elements are delivered into the aneurysm.

D. Delivery Catheter Turning Guide

Figure 24A:
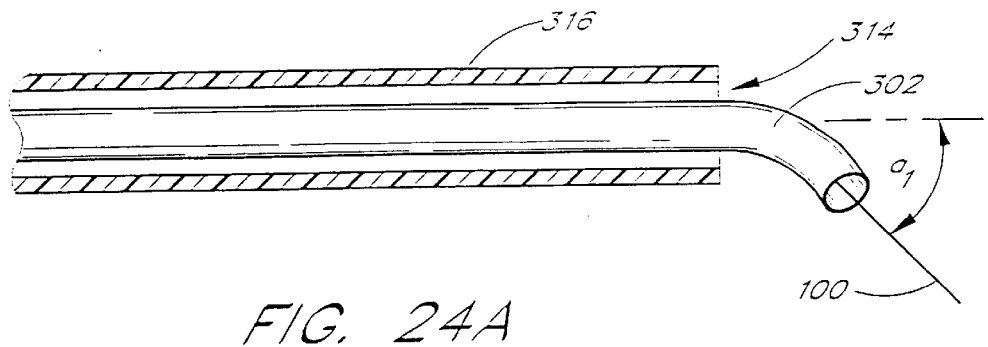
FIGS. 24A–24C are partial side views of the device of FIG. 23, illustrating the increasing emergence of the delivery catheter from the distal end of a channel.
Figure 24B:
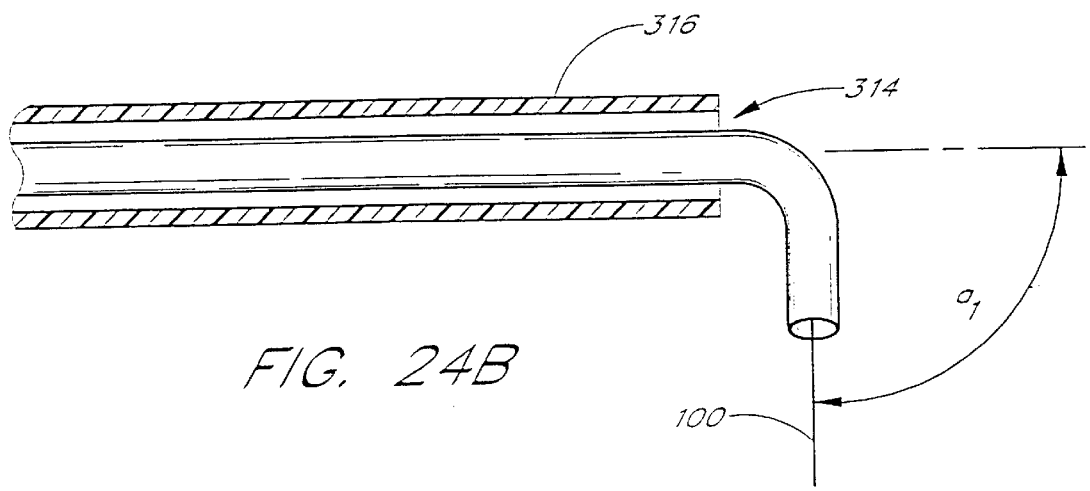
Figure 24C:
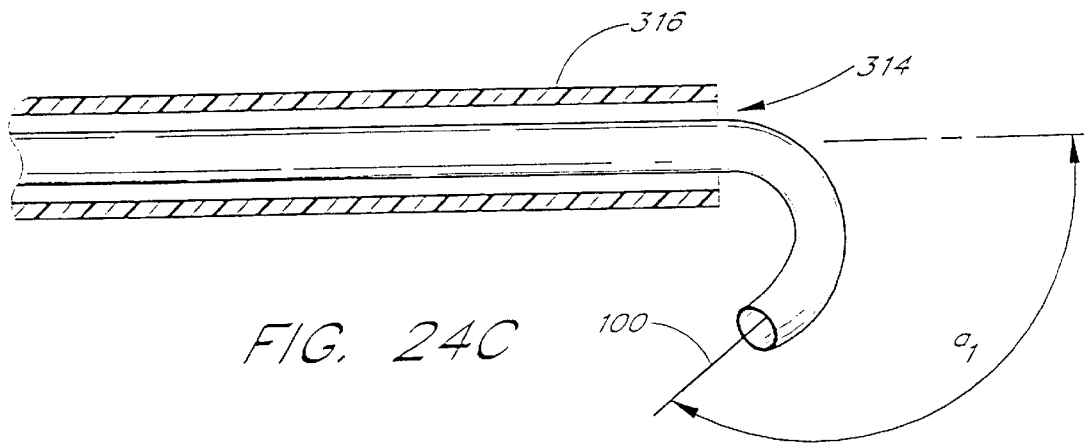

FIGS. 23–24C illustrate another method for delivering a guidewire at an angle into the myocardium. As illustrated in FIG. 23, a delivery catheter 300 comprises a tubular member 302 having a proximal end 304 and a distal end 306 and a lumen 308 extending therethrough. A distal portion 310 is provided with a spring bias or memory tending to form the distal end portion into an arcuate configuration, e.g., a substantially U-shaped configuration. At proximal end 304, tubular member 302 is preferably provided with a flange or other hand grip 312 for facilitating use of the device as described in detail hereinafter.

As illustrated in FIGS. 24A–24C, tubular member 302 is insertable through a delivery channel 314 of an insertion tube or catheter 316. Tubular member 302 is longitudinally slidable in channel 314. Accordingly, distal end portion 310 of tubular member 302 may be maintained in a relatively straightened configuration in a distal end section of channel 314 during insertion and removal of tube 316 from a patient. Upon the arrival of the distal end of insertion tube 316 at a desired insertion site, tubular member 302 is shifted in the distal direction through channel 314 until a part of distal end portion 310 emerges from the channel and bends under the action of the internal spring force built into tubular member 302.

As illustrated in FIGS. 24A–24C, the degree of bending of distal end portion 310 of tubular member 302 is determined by controlling the degree of ejection of distal end portion 310 from channel 314. The more tubular member 302 is pushed in the distal direction, the greater the angle $a_1$ that a tip 306 of tubular member 302 bears with respect to a longitudinal axis of channel 314. The angle $a_1$ may thus be adjusted anywhere from about 0 to 180 degrees.

Figure 25A:
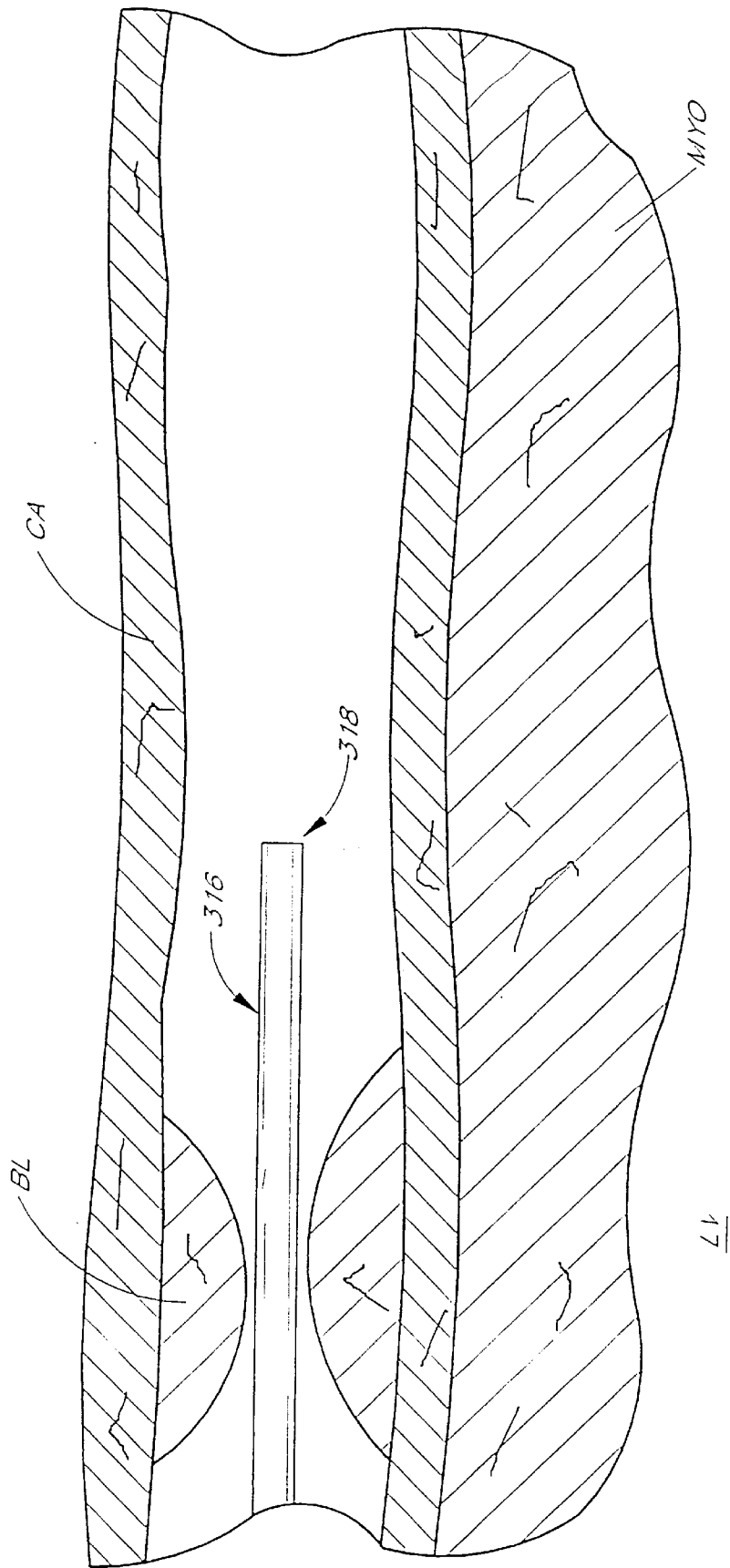
FIGS. 25A–25C are side views showing delivery of the device of FIG. 23 in a coronary artery adjacent the myocardium, with the artery and myocardium shown partially cut away.
Figure 25B:
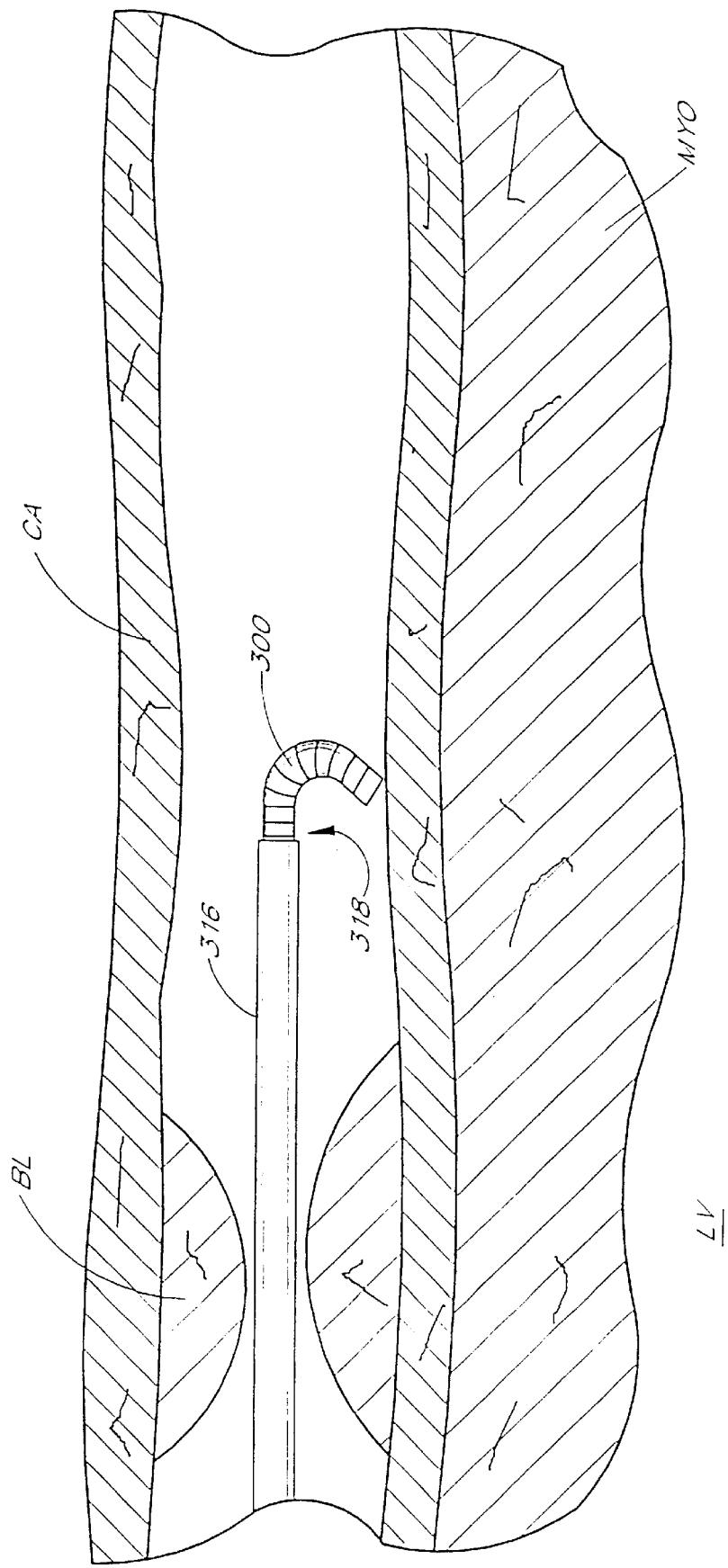
Figure 25C:
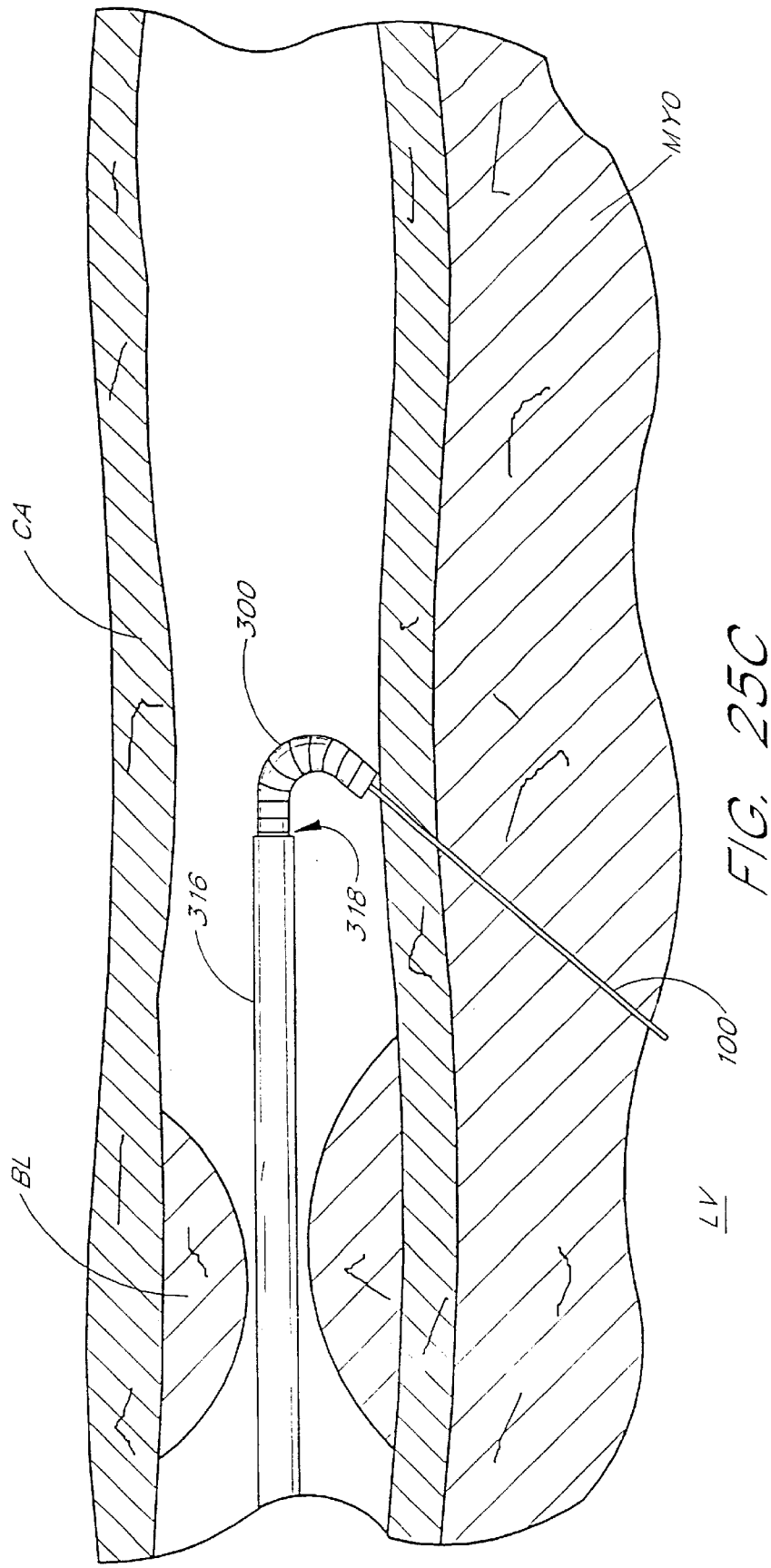

As illustrated in FIG. 25A, to deliver the delivery catheter 300 to a location adjacent the myocardium, the insertion tube 316 may be advanced percutaneously using any of the methods described above until its distal end 318 is adjacent to the insertion site. The delivery catheter 300, as shown in FIG. 25B, is ejected from the distal end 318 until the desired angle is attained relative to the myocardium MYO. As shown in FIG. 25C, a guidewire 100 is then inserted through the lumen in the delivery catheter into the myocardium MYO at the desired angle.

Further details regarding this method are disclosed in U.S. Pat. No. 5,386,818, the entirety of which is hereby incorporated by reference.

E. Reverse Guidewire

Figure 26A:
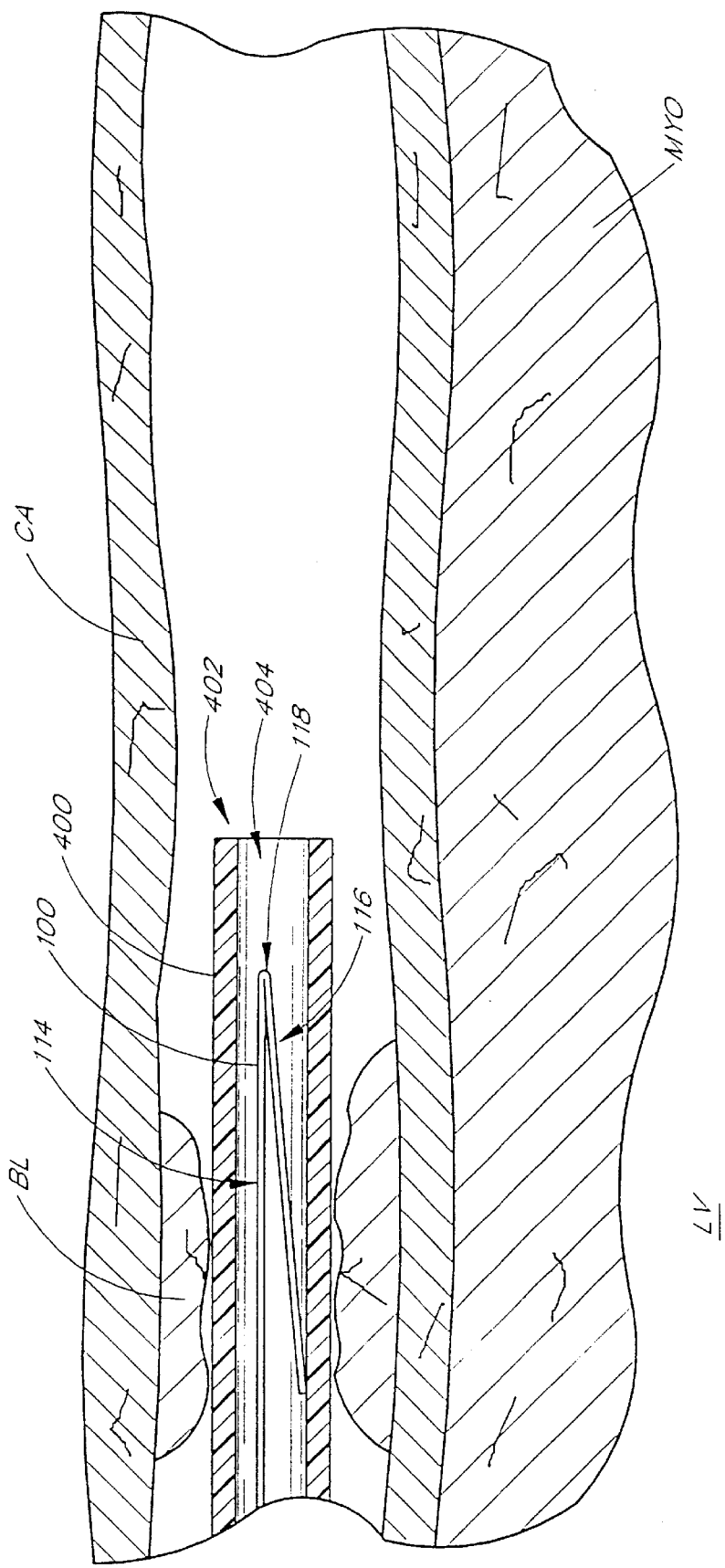
Figure 26B:
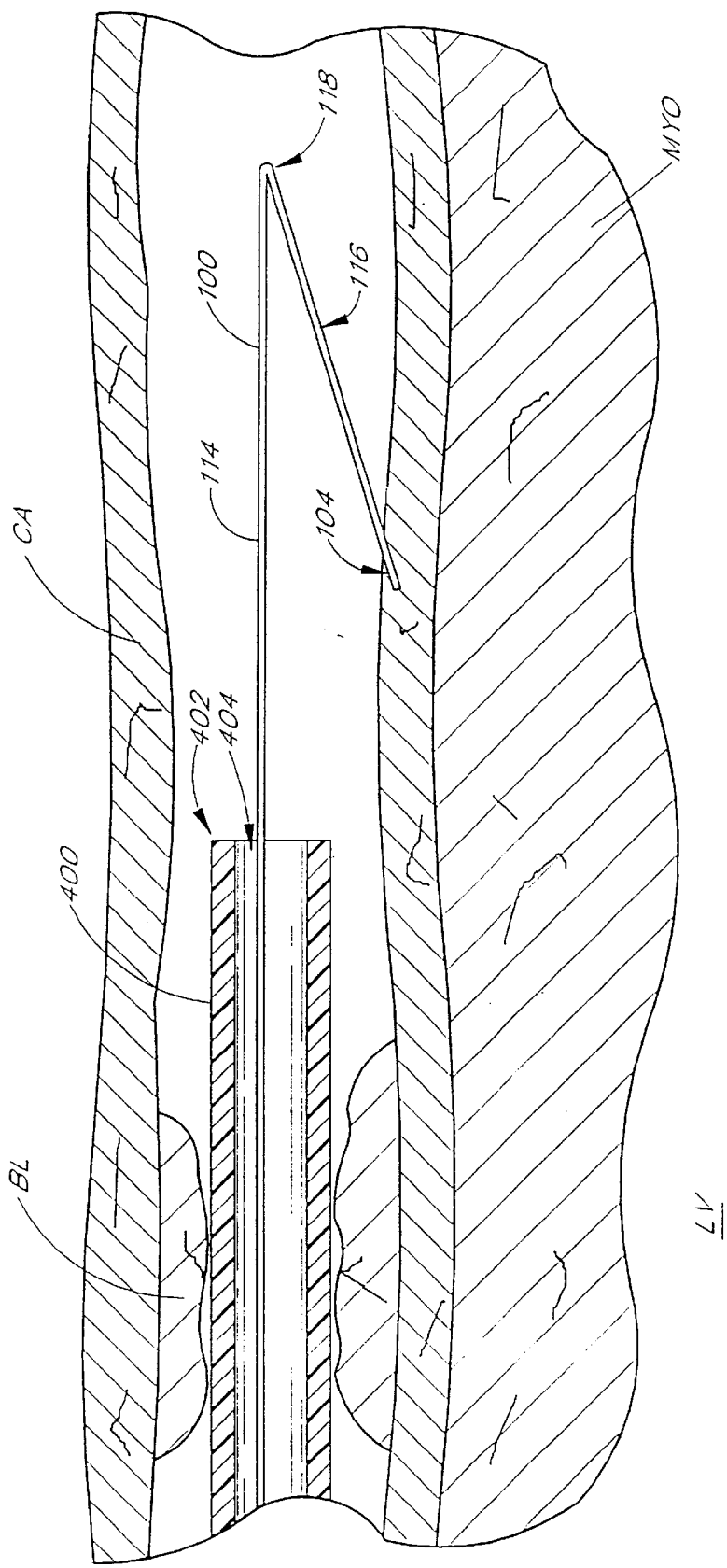

FIGS. 26A–26C illustrate another method for delivering a guidewire at a back angle into the myocardium. As shown in FIG. 26A, a delivery tube 400 is advanced into the coronary artery CA adjacent the myocardium MYO using any of the methods described above. A guidewire 100 is delivered through the lumen 404 of the delivery tube toward the distal end 402 of the delivery tube. Preferably, before insertion of the guidewire 100 into the lumen 404, the guidewire is folded such that it has a distal section 116 that folds back over the proximal section 114. The length of the distal section 116 from the fold 118 to the distal end 104 of guidewire 100 is preferably selected to be greater than the length that the guidewire is to be inserted through the myocardium MYO. The guidewire once located inside the lumen 404 at the distal end 402 of the delivery tube 400 is preferably turned so that the distal section 116 is closest to the myocardium MYO.

In one embodiment, the guidewire 100 is made of a shape memory alloy material such as nitinol. In this embodiment, the shape of the folded guidewire may be set by a memory imparting heat treatment, as would be known to one skilled in the art. More particularly, the angle of the fold may be set before insertion of the guidewire into the lumen 404 to correspond with the desired angle of insertion of the guidewire into the myocardium relative to the axis of the delivery tube. Then, when the guidewire 100 is inserted into the lumen 404, the angle of the fold decreases to accommodate insertion, but not to such an extent as to cause permanent deformation of the guidewire.

As shown in FIG. 26B, the guidewire 100 is ejected from the distal end 402 of the delivery tube 400 such that the distal section 116 is completely outside of the lumen 404. Once outside the lumen 404, the distal section 116 still remains folded relative to the proximal section 114, though preferably, the angle of the fold returns to its original shape-set configuration. As shown in FIG. 26C, after the distal section 116 is outside of the lumen 404, the guidewire can be pulled back proximally, causing the distal tip 104 of the guidewire to puncture into the myocardium MYO at a desired insertion point. The guidewire 100 continues to be pulled back proximally until the distal tip 104 has punctured through the myocardium MYO into the left ventricle LV. After placement of the guidewire 100, a stent may be delivered into the myocardium as described below.

F. Reverse Catheter

Figure 27:
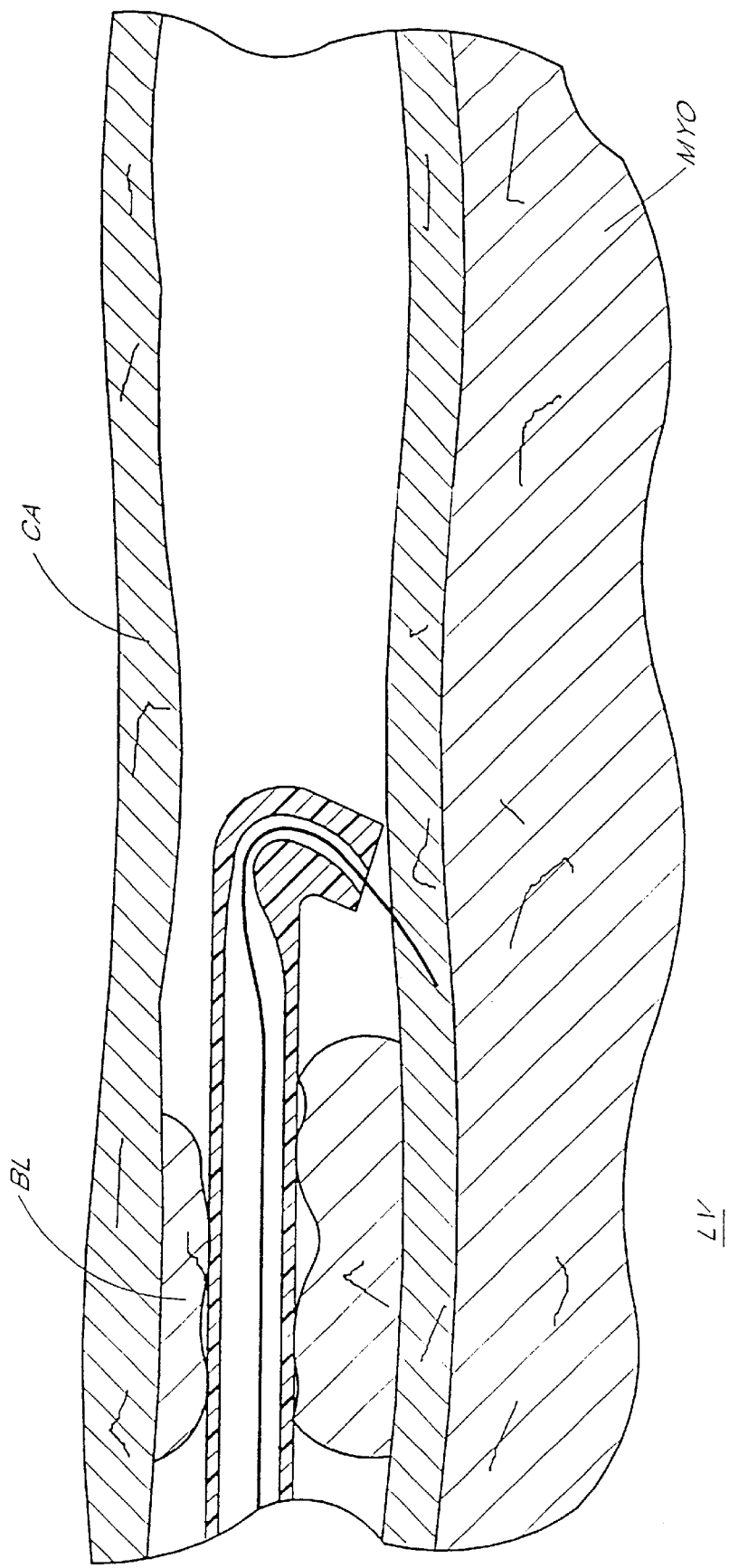
FIG. 27 is a schematic, partial cross-sectional view of a coronary artery adjacent a left ventricle, showing delivery of a guidewire through a delivery catheter at a back angle.

FIG. 27 illustrates another embodiment for delivering a guidewire at a back angle into the myocardium. In this embodiment a delivery catheter 500 is preferably delivered to an insertion site adjacent the myocardium MYO and turned toward the myocardium using any of the methods described above. The delivery catheter is specially constructed to have a lumen 506 that tapers inwardly toward the distal end 504. In other words, the walls of the catheter 500 increase in thickness toward distal end 504 to provide a narrowing passageway 508. A guidewire 100 is inserted through the lumen 506 at the proximal end 502 (not shown) of the delivery catheter and is guided through the narrowing passageway 508 and out of the distal end 504 in a desired direction at the insertion site. As illustrated in FIG. 27, by the combination of turning the distal end of the delivery catheter and providing the narrowing passageway 506, the guidewire 100 preferably exits the delivery catheter at a back angle into the myocardium.

III. Anchoring Guidewire

The embodiments described above are directed primarily to providing a guidewire 100 into the patient's myocardium. As described in further detail below, this guidewire is used for delivering medical devices into the myocardium. However, it should be appreciated that many of the embodiments described above may also be used in conjunction with other methods for creating a passageway through the myocardium. For instance, a delivery catheter, such as described above, may be used for delivering a surgical drill or other tissue penetrating device ejected from the distal end thereof. This approach would be useful, for instance, in creating a tunnel through the myocardium as described above. Alternatively, a Seldinger wire may be ejected from the distal end of the delivery catheter. Further details are described in the above-referenced U.S. Pat. No. 5,429,144.

Figure 28:
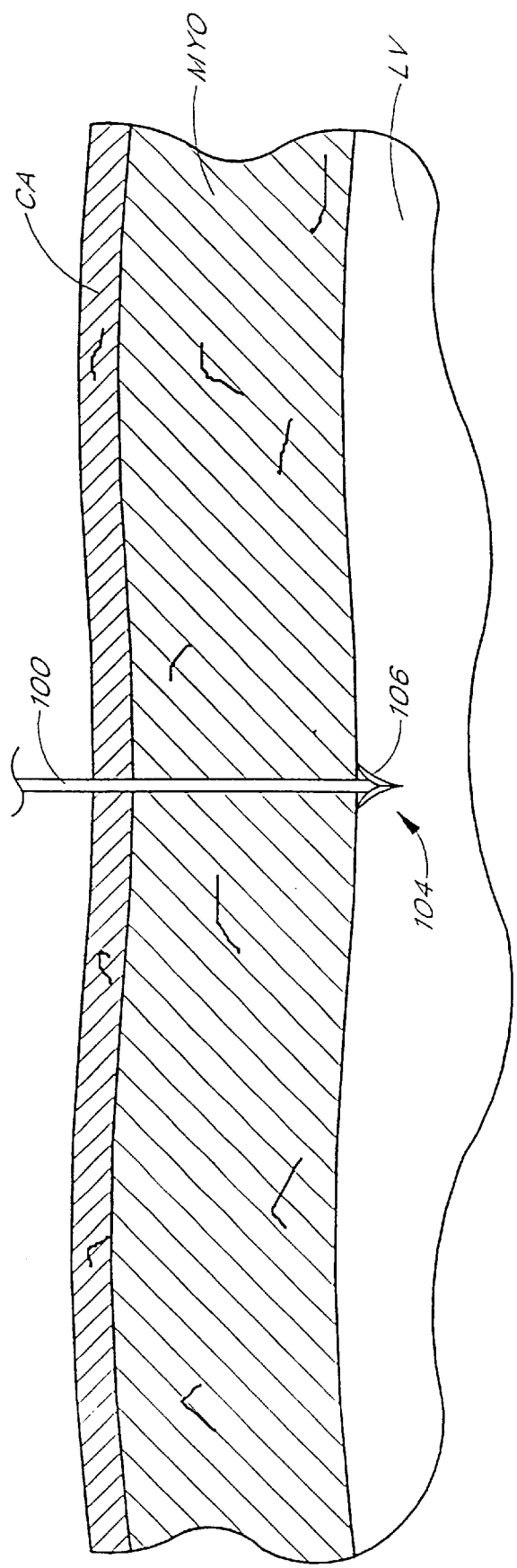
FIG. 28 is a side view of an anchoring guidewire extending through the myocardium, with the myocardium shown partially cut away.

As shown in FIG. 28, a puncture device such as guidewire 100 is directed into the myocardium 100 using any of the preferred methods described above. Guidewire 100 preferably has a proximal end 102 (not shown) which remains outside the patient's body, and a distal end 104 which is inserted through a delivery catheter as described above.

Where the delivery catheter is provided through the coronary artery, the guidewire is advanced in one embodiment until the distal end 104 of the guidewire enters the left ventricle. Alternatively, where it is desired that a stent or other device extend only partially into the myocardium, the guidewire 100 need not extend all the way through to the left ventricle. The distal tip 104 of the guidewire 100 is preferably made of a radiopaque material that can be visualized by the physician by an available method, such as fluoroscopy.

The distal end of the guidewire 100 is preferably formed such that it is easily advanced but is difficult to pull back through the tissue. As shown in FIG. 28, one embodiment of the distal tip 104 comprises one or more barbs 106 extending from the tip in a type of "multi-winged arrowhead" configuration These barbs allow the guidewire to be advanced distally into the myocardium but require more force to pull the guidewire 100 proximally out of the myocardium, thus creating an effective anchor.

Figure 29A:
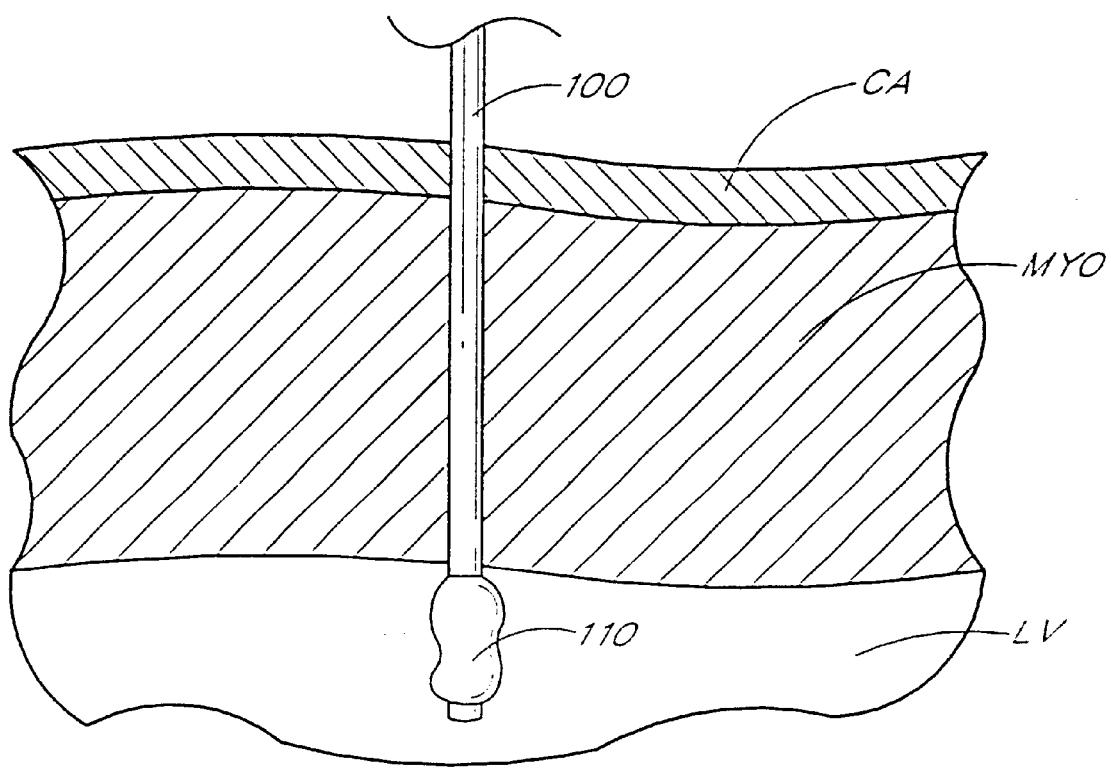
FIG. 29A is a side view of a guidewire carrying an inflatable balloon on its distal end extending through the myocardium, with the myocardium shown partially cut away.
Figure 29B:
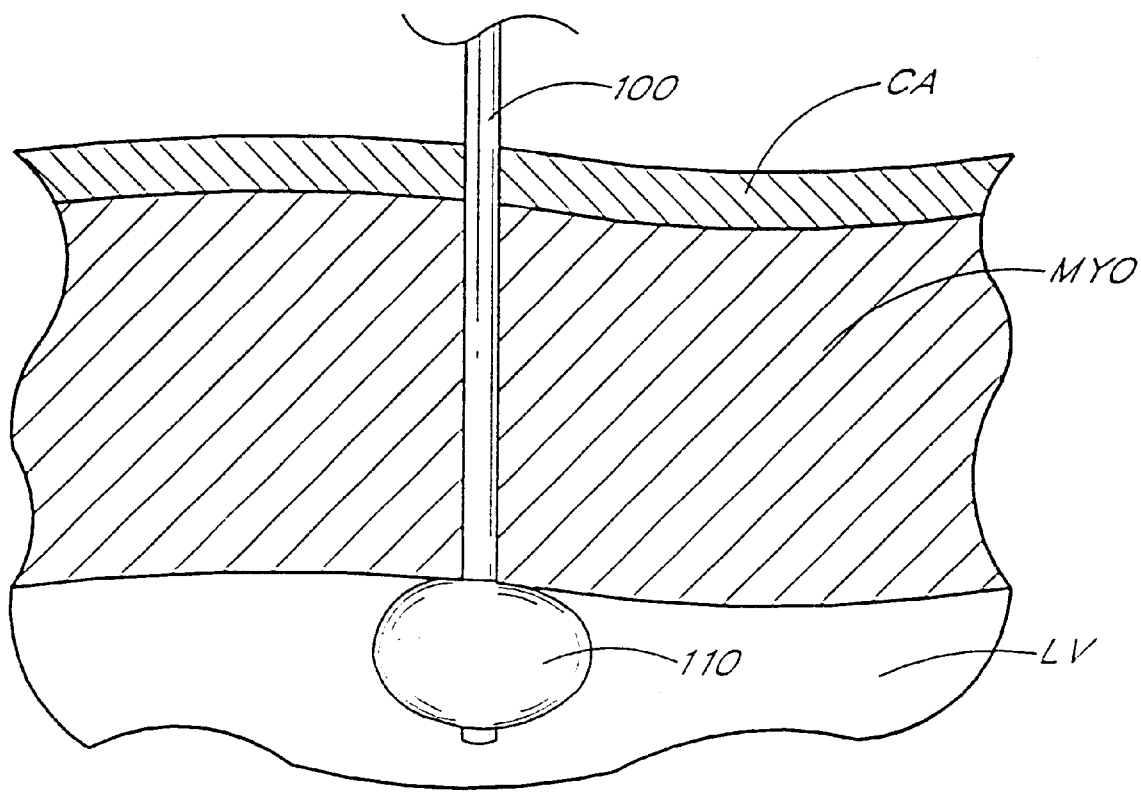
FIG. 29B is a side view of the guidewire of FIG. 29A, showing the balloon inflated to anchor the guidewire against the myocardium.

FIG. 29A shows another embodiment wherein a guidewire 100 carries an expandable member such as balloon 110 on its distal end. Use of an expandable member reduces damage to the myocardium during subsequent retraction of the wire 100. As illustrated in FIG. 29B, once the balloon 110 reaches the left ventricle LV, the balloon 110 is inflated. The balloon is then preferably pulled proximally back to the ventricle wall to anchor and secure the guidewire 100 in place.

Figure 30A:
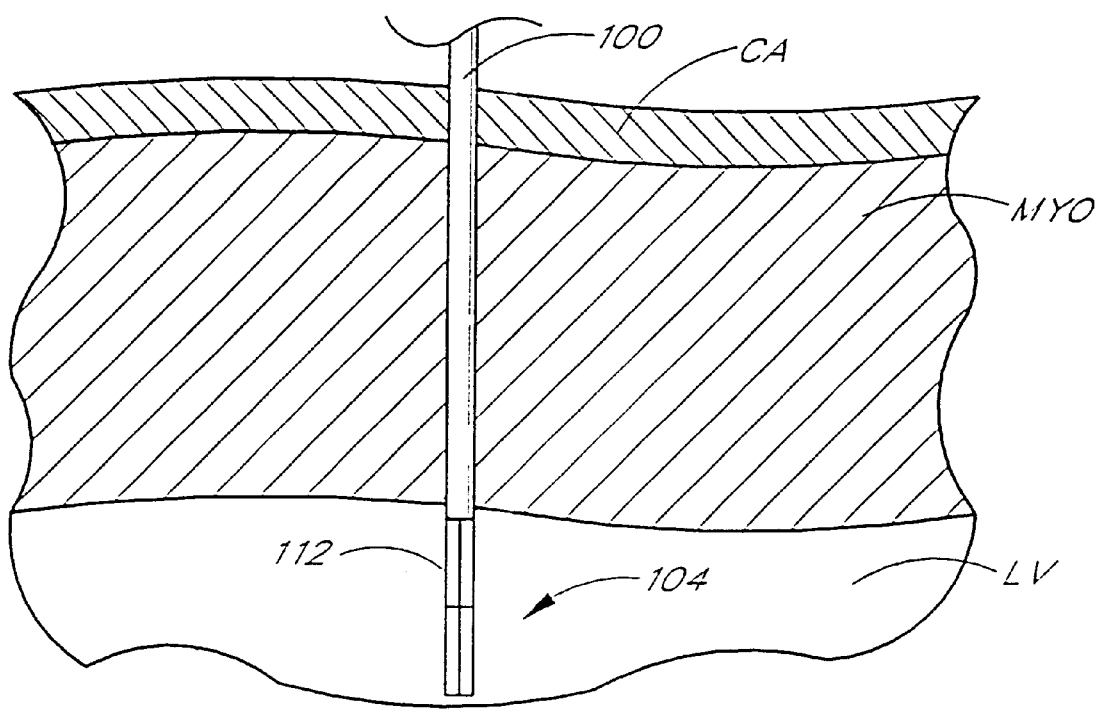
FIGS. 30A–30C are side views of an alternative embodiment of a guidewire anchored to the inner wall of the myocardium, with the myocardium shown partially cut away.
Figure 30B:
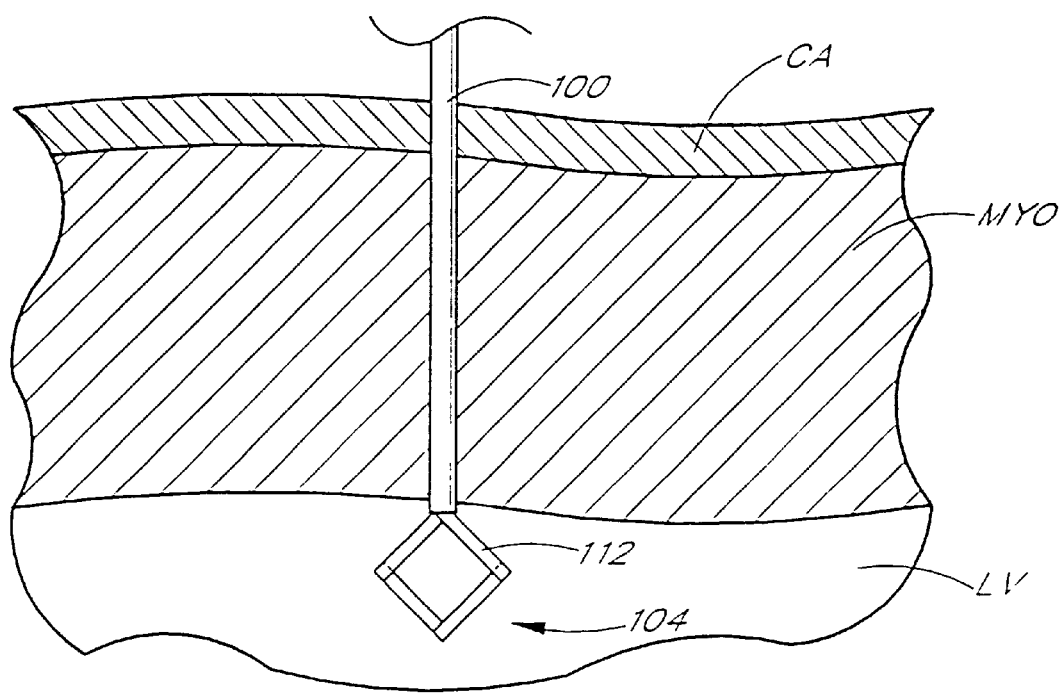
Figure 30C:
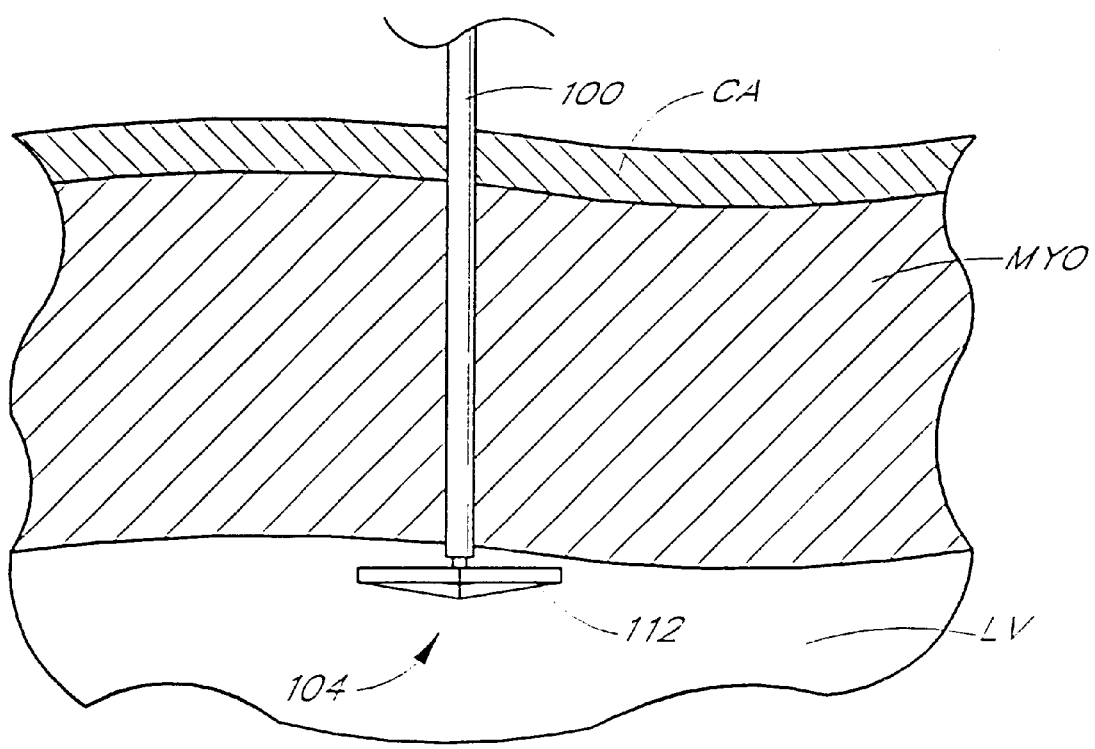

Alternatively, FIGS. 30A–30C show an expandable guidewire 100 extending through and actuated to anchor the guidewire within the myocardium MYO. In FIG. 30A, a guidewire 100 is shown advanced through the myocardium MYO. Guidewire 100 is provided with an expandable device 112 on distal end 104 which may be actuated by an operator at the proximal end of the guidewire outside of the patient. Actuating of the device may be accomplished by using a shape memory material such as nitinol and heating the material above its transformation temperature. Alternatively, the guidewire may be mechanically actuated to assume the desired shape. FIG. 30B shows the guidewire 100 partially actuated at its distal end 104 to expand the device 112 into an anchorable shape. FIG. 30C shows the expandable device 112 fully actuated to anchor the guidewire 100 against the ventricle wall. Other types of anchoring and expandable members may also be used to secure the guidewire 100.

Figure 31:
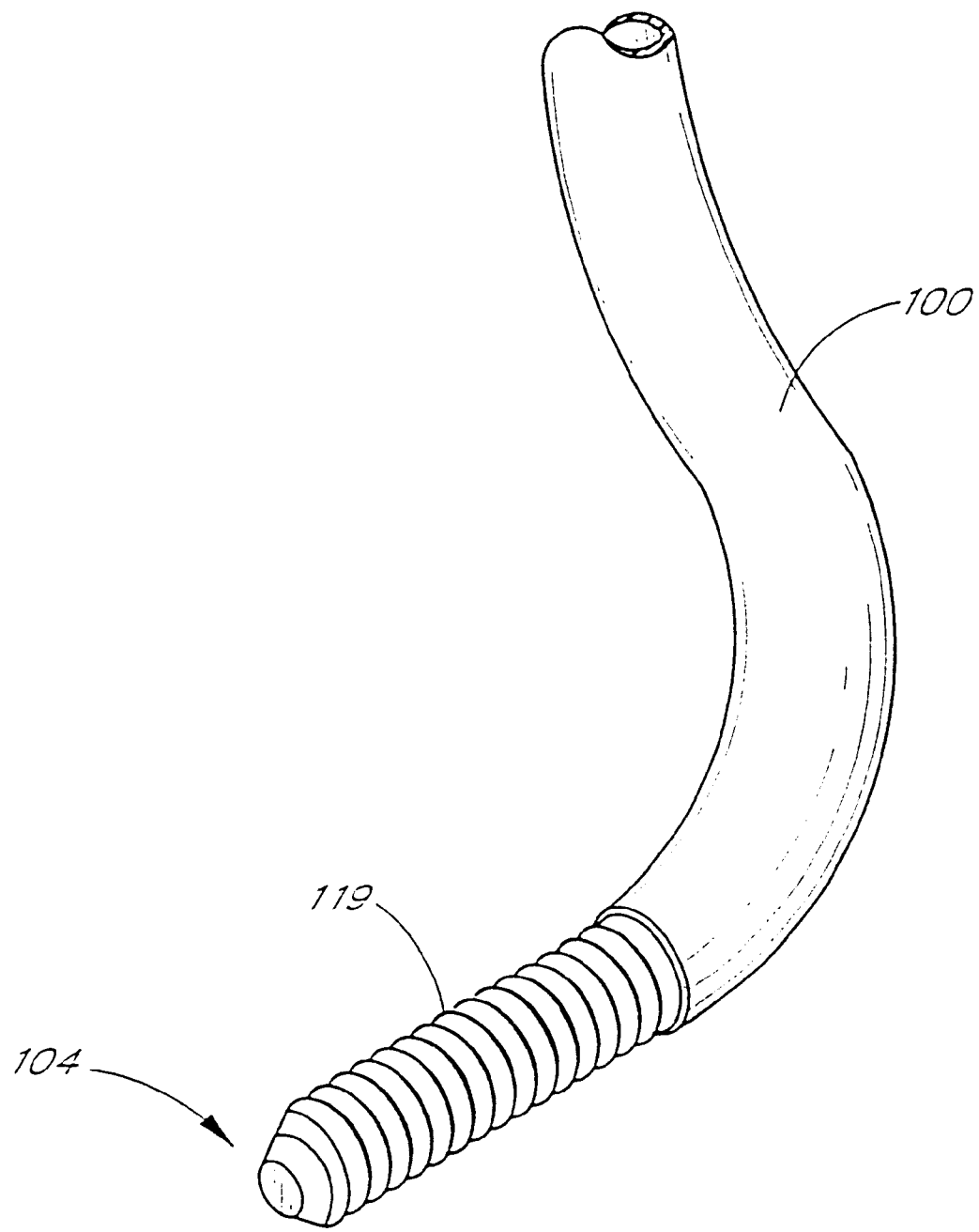
FIG. 31 is a perspective view of a guidewire with a screw tip.

FIG. 31 illustrates a specially constructed guidewire 100 having a screw tip 119. More particularly, the distal end 104 of the guidewire 100 is shaped in a screw configuration to assist in puncturing through the myocardium.

Once the guidewire 100 is anchored in place, the delivery catheter may be removed without displacing the guidewire inserted through the myocardium. Then, with the guidewire 100 anchored in place, catheters used in creating and stenting the passageway or other medical devices may be provided into the myocardium. Alternatively, the delivery catheter may remain within the blood vessel and other catheters or medical devices may be advanced over the guidewire and through the delivery catheter. Furthermore, an expandable member such as a balloon may be provided on the delivery catheter or on the guidewire 100 to anchor the catheter or guidewire to the wall of the blood vessel to provide for more secure deployment of medical devices into the myocardium.

IV. Delivery Over the Guidewire

The anchoring of the guidewire 100 within or to the myocardium MYO allows for the delivery of devices into the myocardium for creation of a myocardial passageway. In particular, the anchoring of the guidewire 100 facilitates advancement of over-the-wire catheters such as introducer catheters into the myocardium by employing a push-pull mechanism. When it is desired to push a catheter over the guidewire 100, the guidewire 100 may be pulled proximally by an operator from outside of the body. The anchoring member at the distal end of the guidewire, whether a balloon, barb, or other member, prevents the guidewire 100 from exiting the myocardium MYO. Meanwhile, a delivery catheter or other over-the-wire device may be pushed into the myocardium MYO, assisted by the pulling force of the anchoring member toward the catheter. The anchoring member also assists in placement of an over-the-wire catheter in the myocardium by preventing the catheter from extending beyond the location of the anchoring member.

Figure 32:
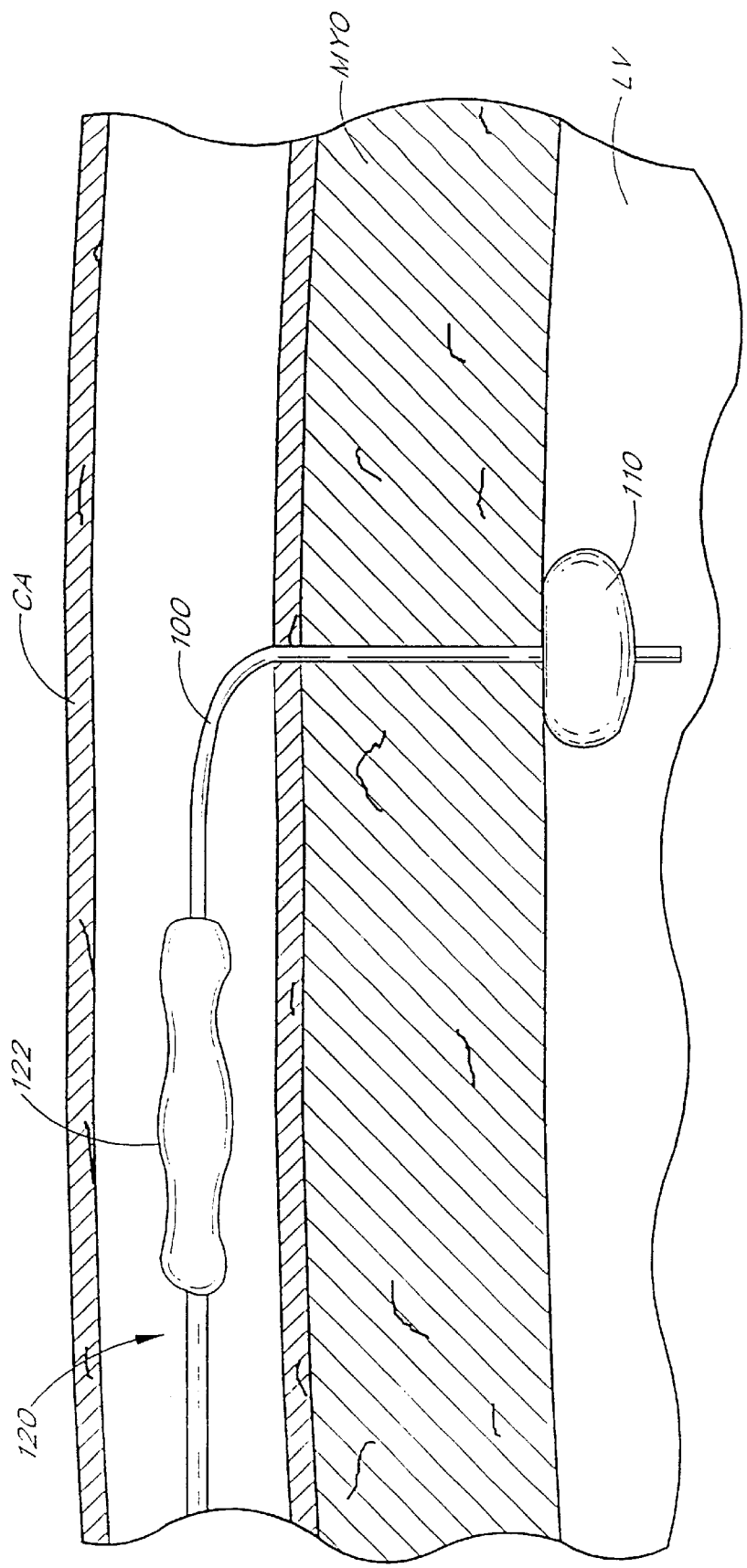
FIG. 32 is a side view of a dilation catheter in a coronary artery advanced over a guidewire extending into the myocardium, with the artery and the myocardium shown partially cut away.
Figure 33:
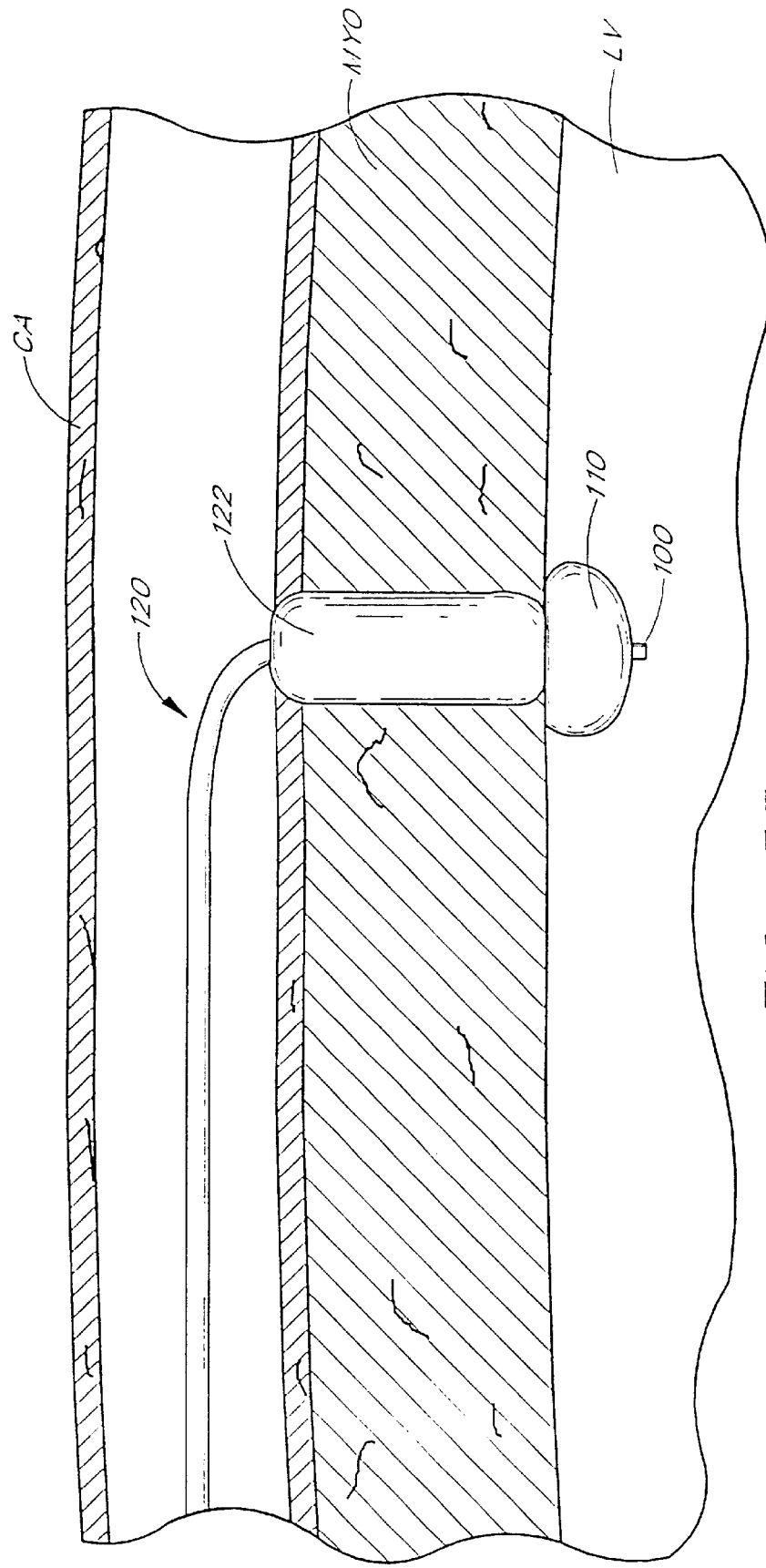
FIG. 33 is a side view of the dilation catheter of FIG. 32 advanced into the myocardium.

As illustrated in FIG. 32, to create a myocardial passageway, a catheter 120 having a dilation balloon 122 is advanced over guidewire 100, into the myocardium MYO, as shown in FIG. 33. The anchored balloon 110 acts as a barrier to advancement of balloon 122, which is subsequently inflated within myocardium MYO to expand a myocardial passageway. The balloon 122 is then deflated and the catheter 120 removed. The process may be repeated with successively larger dilation balloons to form a passageway of desired size.

Figure 34:
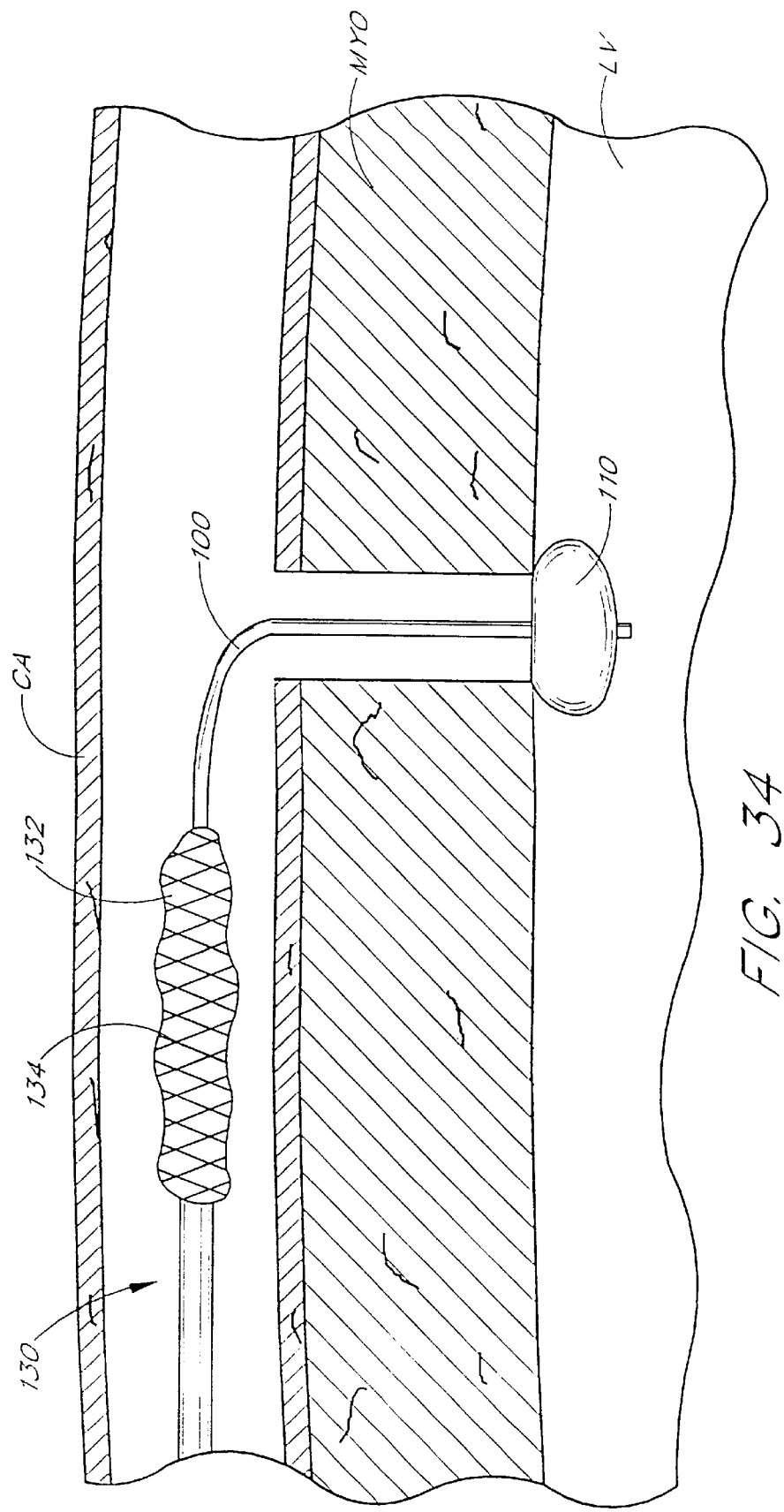
FIG. 34 is a side view of a stent introducer catheter in a coronary artery advanced over a guidewire extending into the myocardium, with the artery and myocardium shown partially cut away.
Figure 35:
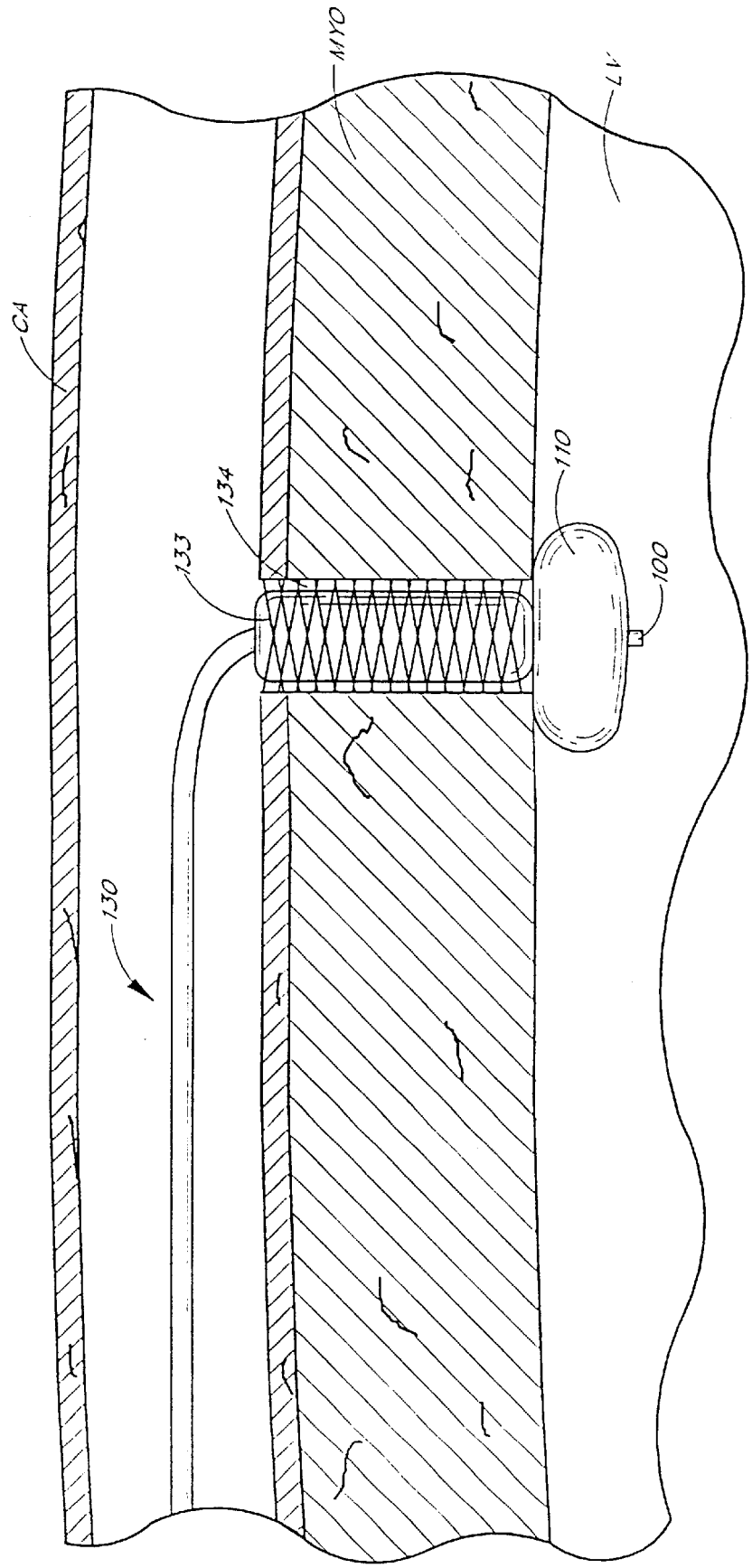
FIG. 35 is a side view of the stent introducer catheter of FIG. 34 advanced into the myocardium.

After inflation of the largest desired dilation balloon, the catheter 120 is withdrawn and a stent introducer catheter 130 is advanced over wire 100, as shown in FIG. 34. The catheter 130 has an inflatable balloon 132 mounted on its distal end for deploying a stent 134 carried by balloon 132. Upon the positioning of balloon 132 inside the myocardium MYO, balloon 132 is inflated, as shown in FIG. 35, to assist in an initial expansion of stent 134 in opposition to the compressive forces of the heart muscle. Upon the desired disposition of stent 134, balloon 132 is deflated and catheter 130 and wire 100 are withdrawn, leaving stent 134 in place to provide a coronary bypass between ventricle LV and artery CA.

It will be appreciated that the stent 134 can be delivered by other methods, such as described in the above-referenced application entitled STENT DESIGNS [Attorney Docket No. PERCAR.013A]. It will also be appreciated that the anchoring of the guidewire may also be used in other applications, such as delivering a shunt between two locations in the body as described above.

V. Drug Delivery

Figure 36:
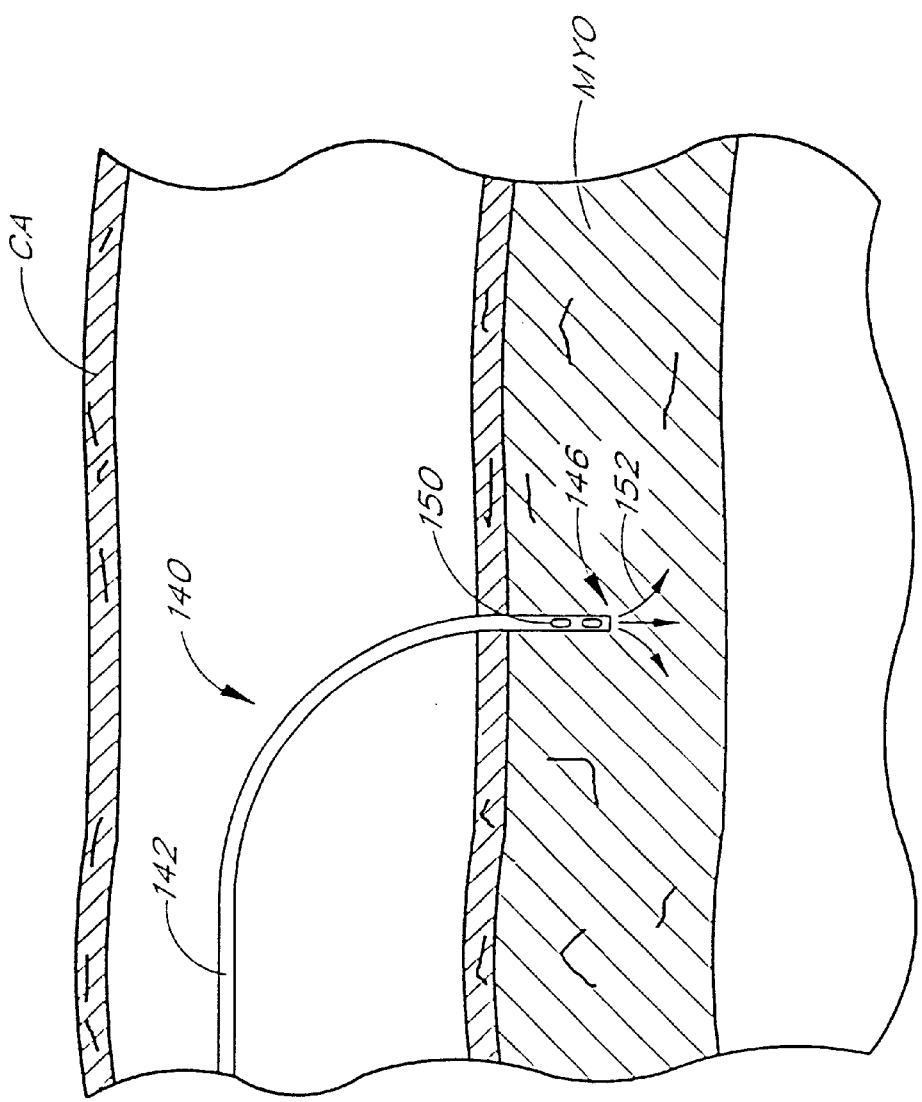
FIG. 36 is a side view of a drug delivery wire advanced through a coronary artery into the myocardium, with the artery and the myocardium shown partially cut away.

The guidewire such as described above delivered into the myocardium MYO may also be used for delivering drugs into the myocardium. As shown in FIG. 36, a guidewire 140 is advanced partially into the myocardium using any of the methods described above. The guidewire 140 comprises a tubular body 142 having a lumen 148 (not shown) extending from a proximal end 144 (not shown) to a distal end 146. The guidewire may be angled using the turning methods described above to provide the distal end of the guidewire at a desired position within the myocardium for drug delivery. Drug delivery fluids 150 are ejected from the distal and 146 into the myocardium. Although the guidewire 140 shown in FIG. 36 is not anchored to the myocardium MYO, anchoring means as described above may be provided. Furthermore, the guidewire 140 may contain a plurality of ports 152 along the tubular body 142 near the distal end 146.

The embodiments illustrated and described above are provided merely as examples of certain preferred embodiments of the present invention. Other changes and modifications can be made from the embodiments presented herein by those skilled in the art without departure from the spirit and scope of the invention, as defined by the appended claims.

What is claimed is:

1. An assembly for delivering a medical device into a heart wall of a patient, comprising:
   an insertion tube having a proximal end and a distal end and a delivery channel extending therethrough;
   a tubular member having a proximal end and a distal end and a lumen extending therethrough, the tubular member having a distal portion provided with an internal spring bias tending to form said distal portion into an arcuate configuration in the absence of an external straightening force on said distal portion, the tubular member being longitudinally slidable in said delivery channel, and wherein said distal portion may be alternately maintained in a relatively straightened configuration in the distal end of said channel and moved outside of said channel to assume said arcuate configuration; and
   a guidewire longitudinally slidable within the lumen of the tubular member.

2. The device of claim 1, wherein the guidewire extends toward the proximal end of the tubular member when a distal end of the guidewire is advanced out of the lumen of the tubular member and the tubular member is in an arcuate configuration.

3. The device of claim 1, wherein the arcuate configuration of the tubular member places the guidewire at an acute angle relative to a longitudinal axis of the proximal end of the tubular member when said guidewire is extended out of the lumen of the tubular member.

4. A device for delivering a guidewire to a heart wall, comprising:
   a delivery tube configured to be inserted within vascular structure of a patient such that the delivery tube extends adjacent to a portion of the heart wall to which the guidewire is to be delivered; and
   a guidewire having a proximal section, a distal section, and a distal tip, said guidewire being configured to be inserted into the delivery tube and through the vascular structure of the patient such that the distal section is folded back on the proximal section when inserted into the delivery tube and said distal tip extends in a direction toward the proximal section when said distal section is ejected from said delivery tube.

5. The device of claim 4, wherein the distal section forms an angle with a longitudinal axis of the delivery tube when said distal section is ejected from the delivery tube.

6. The device of claim 5, wherein the angle formed between the distal section and the longitudinal axis is acute.

7. The device of claim 4, wherein the distal section is at an angle relative to the proximal section.

8. The device of claim 4, wherein the distal section has a length such that the distal section can extend through the heart wall into a heart chamber.

9. The device of claim 4, wherein the guidewire is made of a shape memory material.

10. The device of claim 9, wherein the guidewire is made of nitinol.

11. The device of claim 4, wherein the distal tip is configured to puncture the heart wall and the distal section is configured to extend through the heart wall at an angle.

12. A device for delivering a guidewire to a heart wall, comprising:
   a delivery tube configured to be inserted into a patient such that the delivery tube extends adjacent to a portion of the heart wall to which the guidewire is to be delivered; and
   a guidewire being configured to be inserted into the delivery tube, said guidewire having a proximal section, a distal section, and a distal tip, wherein said distal section forms a first angle with the proximal section such that the distal tip extends in a direction toward the proximal section when the distal section is inserted in the delivery tube, and wherein said distal section forms a second angle with the proximal section such that the distal tip extends in a direction toward the proximal section when the distal section is ejected from the delivery tube, said first angle being less than said second angle.

13. A method for delivering a guidewire at an angle into a desired insertion site in the body, the method comprising:
   delivering an insertion tube into the vasculature of a patient, the insertion tube having a delivery channel extending therethrough and once delivered having a proximal end located outside of the patient and a distal end located adjacent a desired insertion site;
   delivering a delivery catheter through the delivery channel, the delivery catheter having a guidewire lumen extending therethrough, the delivery catheter once delivered having a proximal end outside of the patient and a distal end within the delivery channel;
   ejecting the distal end of the delivery catheter out of the delivery channel at the distal end of the insertion tube, the ejection of the delivery catheter from the delivery channel causing the distal end of the delivery catheter to turn toward the insertion site; and
   advancing a guidewire through the guidewire lumen into the insertion site.

14. The method of claim 13, wherein the delivery catheter comprises a tubular member having a distal portion provided with an internal spring bias tending to form said distal portion into an arcuate configuration in the absence of an external straightening force on said distal portion.

15. The method of claim 13, wherein advancing the guidewire into the insertion site includes advancing the guidewire at an angle to the insertion site.

16. A method for delivering a guidewire into the heart wall, comprising:
   inserting a guidewire into a lumen of a delivery catheter, the guidewire having a proximal section and a distal section, the distal section of the guidewire being folded back over the proximal section while inside the delivery catheter lumen;
   delivering the delivery catheter into a patient, the delivery catheter once delivered having a proximal end outside of the patient and a distal end adjacent a desired insertion site in the heart wall;
   ejecting the distal section of the guidewire out of the lumen of the delivery catheter at its distal end; and
   pulling proximally on the guidewire such that the distal section punctures into the heart wall at an obtuse angle relative to the direction that the guidewire is ejected out of the lumen of the delivery catheter at its distal end.

17. The method of claim 16, further comprising, prior to pulling proximally on the guidewire, turning the guidewire so that the distal section faces the heart wall.

18. The method of claim 16, wherein the distal section is at an angle relative to the proximal section when the distal section is ejected from the catheter.

19. The method of claim 16, wherein prior to ejecting the distal section from the catheter, the guidewire is turned so that the distal section is closer to the heart wall than the proximal section.

20. The method of claim 16, wherein pulling proximally on the guidewire includes extending at least the distal section of the guidewire through the heart wall and into a heart chamber.

21. The method of claim 20, wherein extending the distal section of the guidewire through the heart wall includes extending the distal section at the obtuse angle relative to the direction that the guidewire is ejected out of the lumen of the delivery catheter at its distal end.

22. A method for delivering a guidewire into an insertion site in the body, comprising:

advancing a delivery catheter having a proximal end and a distal end and a lumen extending therethrough into the body, the distal end of the delivery catheter once advanced being located adjacent the insertion site;

turning the distal end of the delivery catheter toward the insertion site; and advancing a guidewire through the lumen in the delivery catheter from the proximal end toward the distal end; and guiding the guidewire out the distal end and into the insertion site through a narrowing passageway formed in the lumen.

23. A method for delivering a guidewire into a heart wall, comprising:

inserting a delivery tube into a patient such that said delivery tube is adjacent a portion of the heart wall to which the guidewire is to be delivered;

advancing the guidewire through the delivery tube, the guidewire having a proximal section, a distal section at an angle relative to the proximal section, and a distal tip;

ejecting the distal section of the guidewire from the delivery tube such that the distal tip extends from the delivery tube toward a proximal section of the guidewire; and inserting the guidewire into the heart wall such that the distal section of the guidewire remains angled to the proximal section of the guidewire.

24. The method of claim 23, wherein the guidewire extends through the heart wall at an angle.

25. The method of claim 23, wherein advancing the guidewire through the delivery tube includes inserting the guidewire in a folded configuration such that the distal section of the guidewire folds back over the proximal section.

26. The method of claim 25, wherein prior to ejecting the distal section from the delivery tube, the guidewire is turned so that the distal section is closer to the heart wall than the proximal section.

27. The method of claim 23, wherein the guidewire is made of a shape memory material.

28. The method of claim 23, wherein the inserting step includes pulling on a proximal end of the guidewire.

29. The method of claim 23, wherein inserting the delivery tube includes inserting the delivery tube such that the delivery tube is substantially parallel to the portion of the heart wall to which the guidewire is to be delivered.

* * * * *